United States Patent
Leeflang et al.

(10) Patent No.: US 12,246,143 B2
(45) Date of Patent: Mar. 11, 2025

(54) SYSTEMS, APPARATUSES, AND METHODS FOR GUIDE WIRE DELIVERY

(71) Applicant: Boston Scientific Scimed, Inc., Maple Grove, MN (US)

(72) Inventors: Stephen A. Leeflang, Sunnyvale, CA (US); Christian S. Eversull, Palo Alto, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 488 days.

(21) Appl. No.: 16/712,774

(22) Filed: Dec. 12, 2019

(65) Prior Publication Data

US 2020/0114121 A1    Apr. 16, 2020

Related U.S. Application Data

(60) Division of application No. 15/672,916, filed on Aug. 9, 2017, now Pat. No. 10,507,302, which is a (Continued)

(51) Int. Cl.
*A61M 25/00* (2006.01)
*A61M 25/01* (2006.01)
(Continued)

(52) U.S. Cl.
CPC .... *A61M 25/0127* (2013.01); *A61M 25/0026* (2013.01); *A61M 25/01* (2013.01); (Continued)

(58) Field of Classification Search
CPC ...... A61M 2025/0004; A61M 25/0113; A61M 25/0127; A61M 25/0133; A61M 25/0147; A61M 2025/015; A61M 25/0158
See application file for complete search history.

(56) References Cited

U.S. PATENT DOCUMENTS 4,200,104 A    4/1980  Harris
4,470,407 A    9/1984  Hussein
(Continued)

FOREIGN PATENT DOCUMENTS

EP    1042990 A1    10/2000
EP    1009303 B1    6/2009
(Continued)

OTHER PUBLICATIONS

Du Pre, B.C. et al., "Minimal coronary artery damage by myocardial electroporation ablation," Europace, 15(1):144-149 (2013).
(Continued)

*Primary Examiner* — William R Carpenter
(74) *Attorney, Agent, or Firm* — Nelson Mullins Riley & Scarborough LLP

(57) ABSTRACT

An apparatus includes a first catheter defining a first longitudinal axis and a first lumen. A first actuator can be coupled to the first catheter and configured to rotate about the first longitudinal axis to deflect a distal end of the first catheter relative to the first longitudinal axis. A second catheter can define a second longitudinal axis and a second lumen. At least a portion of the second catheter can be configured to slide within the first lumen. A magnetic member can be coupled to a distal end of the second catheter. The magnetic member can define a third lumen. The third lumen can be in fluid communication with the second lumen. A second actuator can be coupled to the second catheter and configured to move linearly along the second longitudinal axis so as to vary a spacing between the magnetic member and the first catheter.

16 Claims, 22 Drawing Sheets

Related U.S. Application Data continuation of application No. PCT/US2017/037609, filed on Jun. 15, 2017.

(60) Provisional application No. 62/489,643, filed on Apr. 25, 2017, provisional application No. 62/351,159, filed on Jun. 16, 2016.

(51) Int. Cl.

| | |
|---|---|
| *A61B 17/00* | (2006.01) |
| *A61B 18/00* | (2006.01) |
| *A61B 18/14* | (2006.01) |
| *A61B 90/00* | (2016.01) |
| *A61M 25/06* | (2006.01) |

(52) U.S. Cl.

CPC ............... *A61M 25/0113* (2013.01); *A61B 2017/00876* (2013.01); *A61B 2018/00351* (2013.01); *A61B 2018/00577* (2013.01); *A61B 18/1492* (2013.01); *A61B 2090/3966* (2016.02); *A61B 2218/002* (2013.01); *A61B 2218/007* (2013.01); *A61M 2025/0004* (2013.01); *A61M 25/0068* (2013.01); *A61M 25/0082* (2013.01); *A61M 25/0097* (2013.01); *A61M 25/0133* (2013.01); *A61M 2025/0175* (2013.01); *A61M 25/065* (2013.01); *A61M 2210/122* (2013.01)

(56) References Cited

U.S. PATENT DOCUMENTS

| | | |
|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | Deford et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho et al. |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Toellner et al. |
| 6,607,520 B2 | 8/2003 | Keane |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless et al. |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill et al. |
| 6,973,339 B2 | 12/2005 | Govari |
| 6,979,331 B2 | 12/2005 | Hintringer et al. |

(56) References Cited

U.S. PATENT DOCUMENTS

| | | |
|---|---|---|
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,282,057 B2 | 10/2007 | Surti et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro'et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emmons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |

(56) References Cited

U.S. PATENT DOCUMENTS

| | | |
|---|---|---|
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,016,232 B1 | 7/2018 | Bowers et al. |
| 10,130,423 B1 | 11/2018 | Viswanathan et al. |
| 10,172,673 B2 | 1/2019 | Viswanathan et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,507,302 B2 | 12/2019 | Leeflang et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0095176 A1 | 7/2002 | Prestel |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek-Petric |
| 2003/0229379 A1 | 12/2003 | Maynard |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1* | 1/2007 | Dando ............... A61B 18/1492 606/41 |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1* | 7/2007 | Heuser ............... A61B 17/3478 606/185 |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Sliwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004661 A1 | 1/2010 | Verin et al. |
| 2010/0023004 A1 | 1/2010 | Francischelli et al. |
| 2010/0137861 A1 | 6/2010 | Soroff et al. |
| 2010/0185140 A1* | 7/2010 | Kassab ............... A61M 25/0084 604/35 |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0098694 A1 | 4/2011 | Long |
| 2011/0106221 A1 | 5/2011 | Neal et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |

(56) References Cited

U.S. PATENT DOCUMENTS

| | | |
|---|---|---|
| 2012/0059255 A1 | 3/2012 | Paul et al. |
| 2012/0071872 A1 | 3/2012 | Rubinsky et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0172864 A1 | 7/2013 | Ibrahim et al. |
| 2013/0172875 A1 | 7/2013 | Govari et al. |
| 2013/0184702 A1 | 7/2013 | Neal et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Hue-Teh |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | de la Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1* | 7/2015 | Mickelsen .......... A61B 18/1492 606/41 |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal et al. |
| 2016/0058504 A1* | 3/2016 | Davies ................ A61B 18/1492 600/424 |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelson et al. |
| 2016/0331441 A1 | 11/2016 | Konings |
| 2016/0331459 A1 | 11/2016 | Townley et al. |
| 2016/0354142 A1 | 12/2016 | Pearson et al. |
| 2016/0361109 A1 | 12/2016 | Weaver et al. |
| 2017/0001016 A1 | 1/2017 | De Ridder |

(56) References Cited

U.S. PATENT DOCUMENTS

| | | |
|---|---|---|
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0146584 A1 | 5/2017 | Daw et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0200497 A1 | 7/2018 | Mickelsen |
| 2018/0303488 A1 | 10/2018 | Hill |
| 2018/0311497 A1 | 11/2018 | Viswanathan et al. |
| 2018/0360534 A1 | 12/2018 | Teplitsky et al. |
| 2019/0069950 A1 | 3/2019 | Viswanathan et al. |
| 2019/0151015 A1 | 5/2019 | Viswanathan et al. |
| 2019/0231421 A1 | 8/2019 | Viswanathan et al. |
| 2019/0269912 A1 | 9/2019 | Viswanathan et al. |

FOREIGN PATENT DOCUMENTS

| | | |
|---|---|---|
| EP | 2382935 A1 | 11/2011 |
| EP | 2532320 A2 | 12/2012 |
| EP | 2708181 A1 | 3/2014 |
| EP | 2777579 A1 | 9/2014 |
| EP | 3111871 A1 | 1/2017 |
| EP | 3151773 B1 | 4/2018 |
| JP | 06-507797 A | 9/1994 |
| JP | 2000-508196 A | 7/2000 |
| JP | 2005-516666 A | 6/2005 |
| JP | 2006-506184 A | 2/2006 |
| JP | 2008-538997 A | 11/2008 |
| JP | 2009-500129 A | 1/2009 |
| JP | 2011-509158 A | 3/2011 |
| JP | 2012-050538 A | 3/2012 |
| WO | 92/07622 A1 | 5/1992 |
| WO | 92/21278 A1 | 12/1992 |
| WO | 92/21285 A1 | 12/1992 |
| WO | 94/07413 A1 | 4/1994 |
| WO | 97/24073 A1 | 7/1997 |
| WO | 97/25917 A1 | 7/1997 |
| WO | 97/37719 A1 | 10/1997 |
| WO | 99/04851 A1 | 2/1999 |
| WO | 99/22659 A1 | 5/1999 |
| WO | 99/56650 A1 | 11/1999 |
| WO | 99/59486 A2 | 11/1999 |
| WO | 02/56782 A2 | 7/2002 |
| WO | 03/53289 A1 | 7/2003 |
| WO | 03/65916 A1 | 8/2003 |
| WO | 2004/045442 A1 | 6/2004 |
| WO | 2006/115902 A2 | 11/2006 |
| WO | 2007/006055 A2 | 1/2007 |
| WO | 2009/082710 A1 | 7/2009 |
| WO | 2009/089343 A1 | 7/2009 |
| WO | 2011/028310 A1 | 3/2011 |
| WO | 2012/153928 A2 | 11/2012 |
| WO | 2014/025394 A1 | 2/2014 |
| WO | 2014/031800 A1 | 2/2014 |
| WO | 2015/103530 A1 | 7/2015 |
| WO | 2015/103574 A1 | 7/2015 |
| WO | 2015/171921 A2 | 11/2015 |
| WO | 2015/175944 A1 | 11/2015 |
| WO | 2015/192018 A1 | 12/2015 |
| WO | 2015/192027 A1 | 12/2015 |
| WO | 2016/060983 A1 | 4/2016 |
| WO | 2016/090175 A1 | 6/2016 |
| WO | 2017/119934 A1 | 7/2017 |
| WO | 2017/120169 A1 | 7/2017 |
| WO | 2017/192477 A1 | 11/2017 |
| WO | 2017/192495 A1 | 11/2017 |
| WO | 2017/218734 A1 | 12/2017 |
| WO | 2018/200800 A1 | 11/2018 |

OTHER PUBLICATIONS

Hobbs, E. P., "Investor Relations Update: Tissue Ablation via Irreversible Electroporation (IRE)," Powerpoint (2004), 16 pages.

Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].

Madhavan, M. et al., "Novel Percutaneous Epicardial Autonomic Modulation in the Canine for Atrial Fibrillation: Results of an Efficacy and Safety Study," Pace, 00:1-11 (2016).

Neven, K. et al., "Epicardial linear electroporation ablation and lesion size," Heart Rhythm, 11:1465-1470 (2014).

Neven, K. et al., "Myocardial Lesion Size After Epicardial Electroporation Catheter Ablation After Subxiphoid Puncture," Circ Arrhythm Electrophysiol., 7(4):728-733 (2014).

Neven, K. et al., "Safety and Feasibility of Closed Chest Epicardial Catheter Ablation Using Electroporation," Circ Arrhythm Electrophysiol., 7:913-919 (2014).

Van Driel, V.J.H.M. et al., "Low vulnerability of the right phrenic nerve to electroporation ablation," Heart Rhythm, 12:1838-1844 (2015).

Van Driel, V.J.H.M. et al., "Pulmonary Vein Stenosis After Catheter Ablation Electroporation Versus Radiofrequency," Circ Arrhythm Electrophysiol., 7(4):734-738 (2014).

Wittkampf, F.H. et al., "Feasibility of Electroporation for the Creation of Pulmonary Vein Ostial Lesions," J Cardiovasc Electrophysiol, 22(3):302-309 (Mar. 2011).

Wittkampf, F.H. et al., "Myocardial Lesion Depth With Circular Electroporation Ablation," Circ. Arrhythm Electrophysiol., 5(3):581-586 (2012).

\* cited by examiner

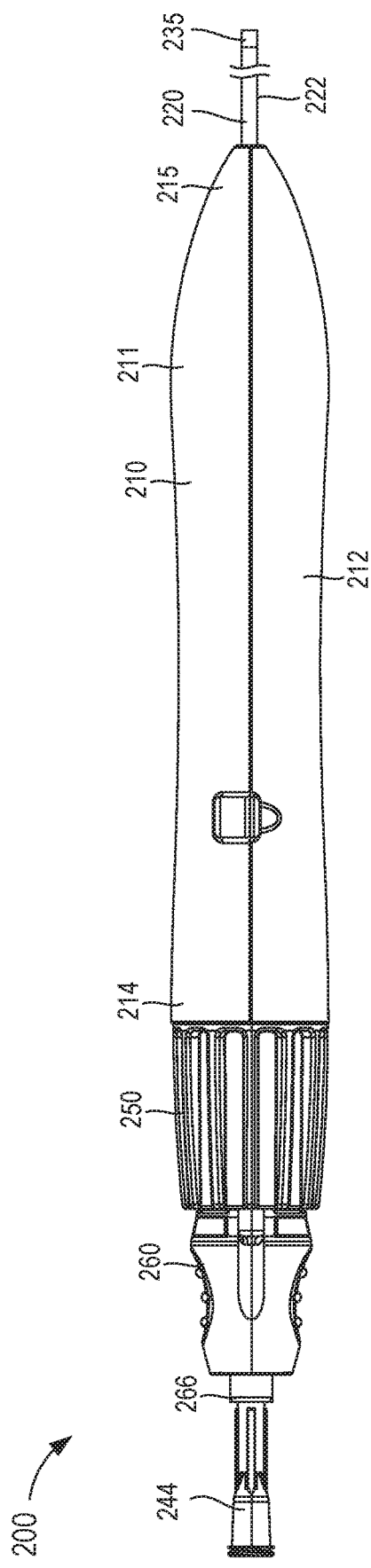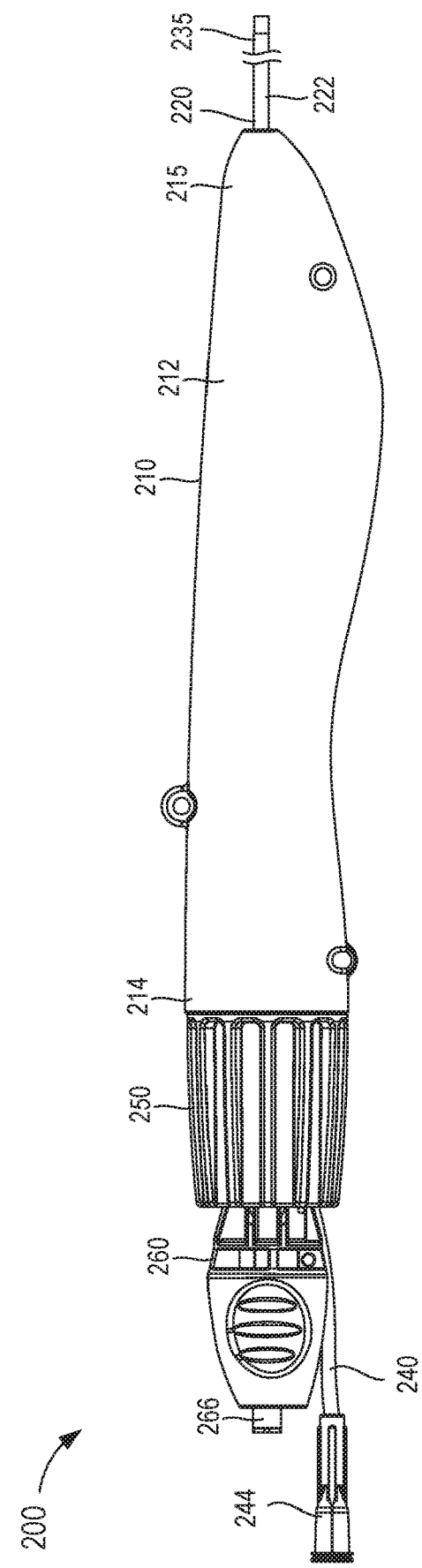
FIG. 4
FIG. 5

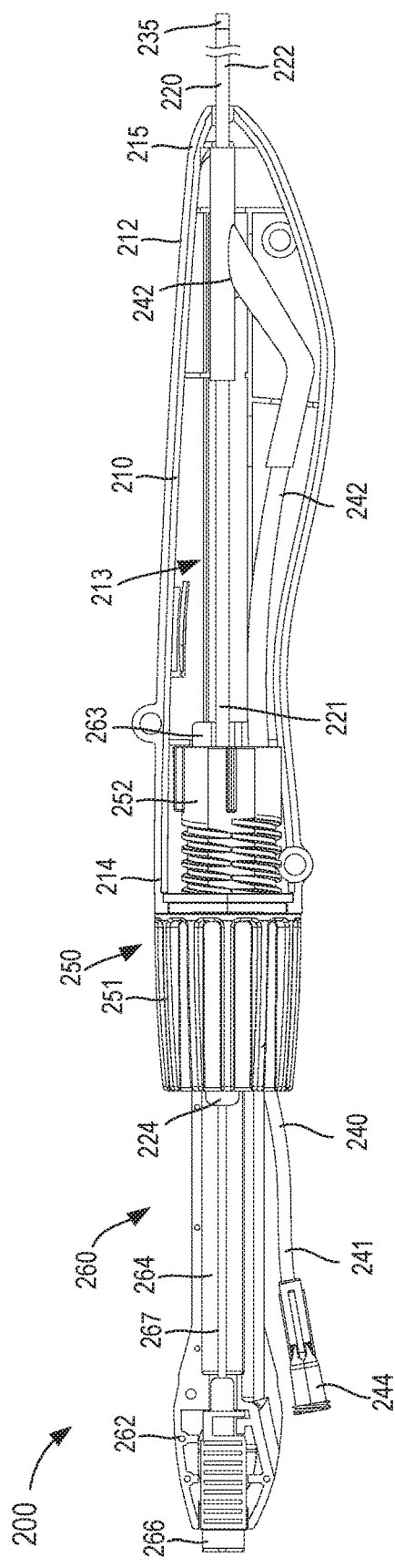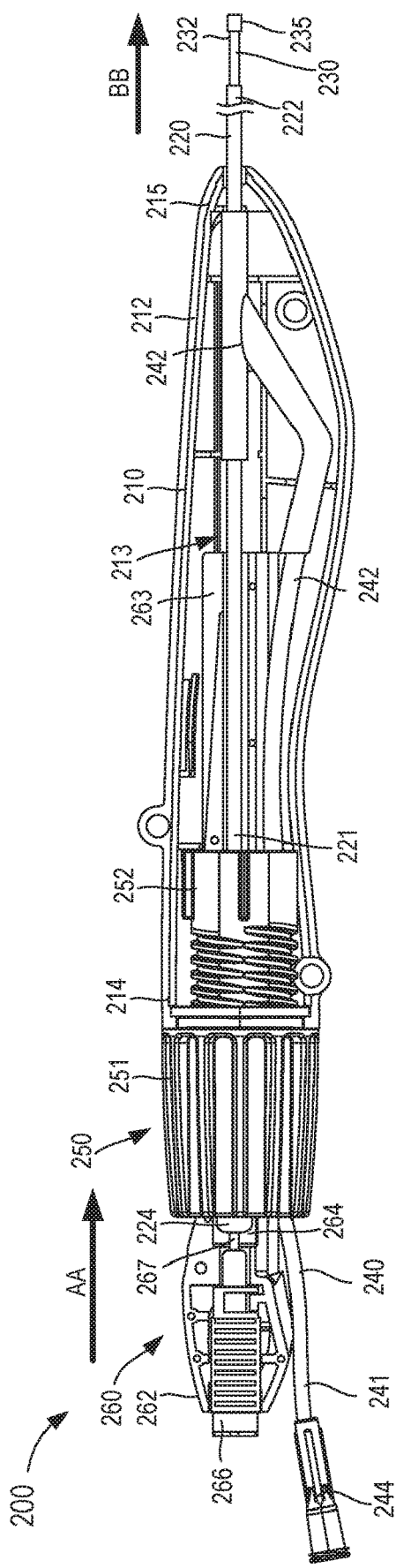
FIG. 6
FIG. 7

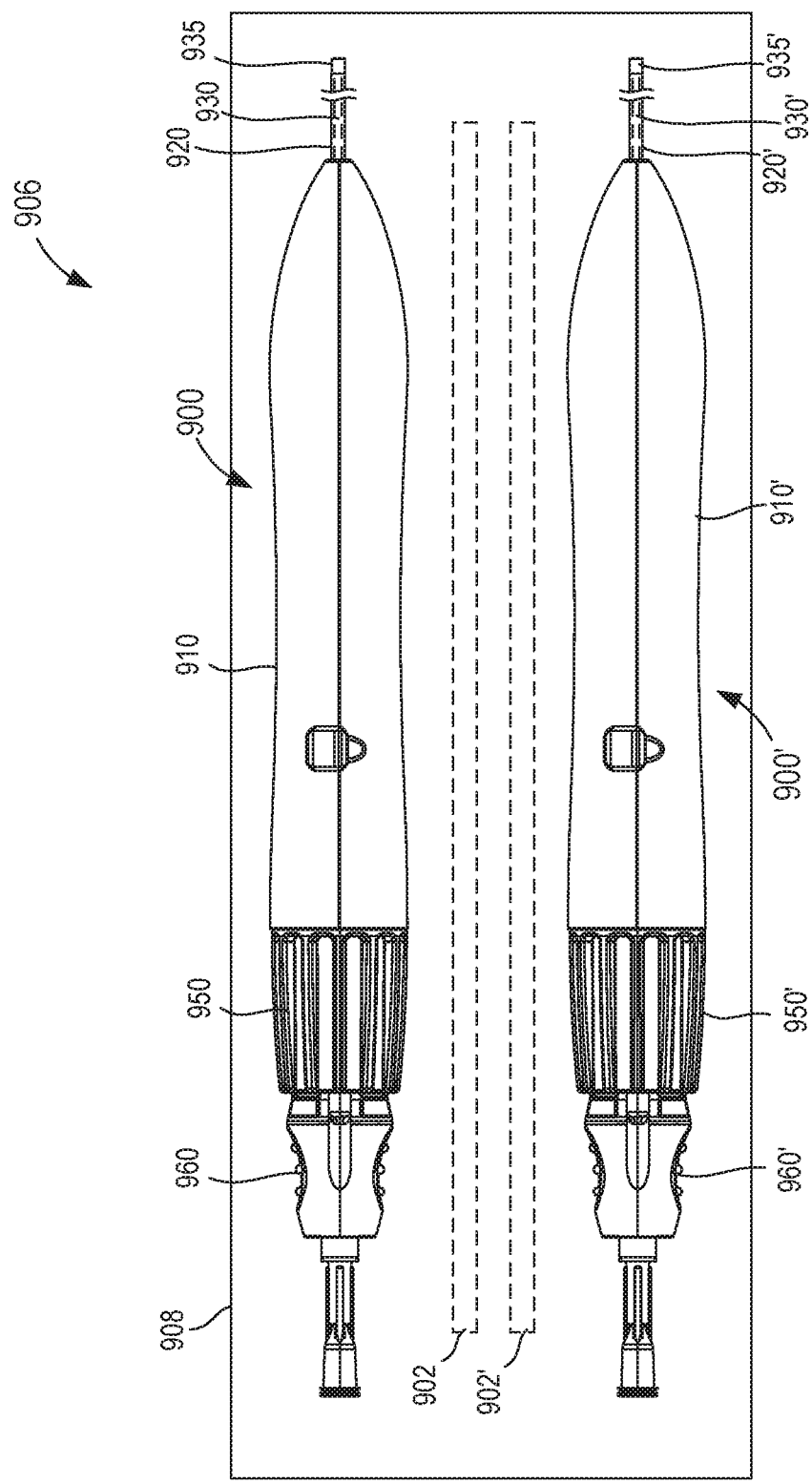

SYSTEMS, APPARATUSES, AND METHODS FOR GUIDE WIRE DELIVERY

CROSS-REFERENCE TO RELATED APPLICATIONS

This application is a divisional of U.S. patent application Ser. No. 15/672,916, entitled "SYSTEMS, APPARATUSES, AND METHODS FOR GUIDE WIRE DELIVERY," filed Aug. 9, 2017, which is a continuation of International Patent Application No. PCT/US2017/037609, entitled "SYSTEMS, APPARATUSES, AND METHODS FOR GUIDE WIRE DELIVERY," filed Jun. 15, 2017, and claims benefit of priority to U.S. Provisional Application Ser. No. 62/351,159, entitled "CATHETER DEVICES AND METHODS," filed Jun. 16, 2016, and to U.S. Provisional Application Ser. No. 62/489,643, entitled "SYSTEMS, APPARATUSES, AND METHODS FOR GUIDE WIRE DELIVERY," filed Apr. 25, 2017, the disclosures of each of which are incorporated herein by reference in their entireties.

BACKGROUND

The embodiments described herein relate generally to medical devices and methods for delivery catheters, and more particularly to delivery catheters configured for creating a passage in and/or through a target tissue for placement of a guidewire.

Many surgical procedures include delivering at least a portion of a device such as a catheter or the like to positions within a patient where access may be limited (e.g., by the anatomy or the like). For example, atrial fibrillation of a heart is typically treated by isolating portions of the atria. Such isolation of the atria can be done by open-heart surgery (e.g., a modified Maze procedure) or, most commonly, by a trans-venous catheter technique. In some known instances, the doctor cauterizes the left atrial muscle tissues using radiofrequency ablation techniques, with the ablation lesion targeting and/or circumscribing the pulmonary veins. Isolation of these anatomic portions of atria prevents the electrical propagation of the arrhythmia into the remainder of the atria. Generally, the operator (e.g., surgeon or interventionalist) places electrophysiologic catheters into the right heart. Under fluoroscopic guidance, a catheter is advanced adjacent to the atrial septum. In most cases, a puncture of the atrial septum (right to left) is made with a specialized needle catheter. A guidewire is then advanced into the left atrium.

The trans-septal catheter is removed and a guide catheter is delivered over the wire into the left atrium. An ablation catheter is then advanced into the left atrium under fluoroscopic guidance. Typically, electrophysiologists use additional imaging and mapping technology to improve safety and efficacy of the procedure, such as intracardiac ultrasound, cardiac computed tomography (CT), or non-contact mapping systems. Once the ablation/mapping catheters are in the left atrium, the operator delivers radiofrequency energy to the target sites. The operator moves the ablation catheter in a point-by-point fashion connecting the lesions, which in effect, electrically isolates the pulmonary veins from the rest of the atrium.

These known procedures typically take 3-6 hours to complete. The procedural success varies between operators and patient selection (success rate is between 50-85% for a single attempt), with some patients receiving subsequent ablation procedures to "touch up" the prior ablation site. The cost of these procedures is variable and increases substantially with duration of procedure and/or the addition of adjuvant imaging/mapping technology. Generally, current procedures are associated with a 5-6% risk of procedural complications, including a 0.5% risk of stroke due to instrumenting (i.e., placing one or more medical devices into) the left atrium. Other complications can include cardiac perforation, tamponade, pulmonary vein stenosis, and atrial-esophageal fistula. Despite attempts to simplify and streamline the procedure, the anatomic variations of the left atrium and pulmonary veins have limited the utility of alternative ablation techniques.

In some known instances, pericardial techniques for treating atrial fibrillation are employed; however, such known techniques also have various limitations. For example, most current pericardial ablation strategies include an operator blindly navigating recesses of the pericardial space with an ablation catheter. In some instances, reflections formed in the pericardial space, also described as "pericardial reflections", can pose an obstacle to delivery of a single contiguous lesion using these techniques. Thus, the anatomy of the pericardial space limits the efficacy and technical ease of current pericardial/epicardial catheter-based procedures. For example, although the membranous reflections of the pericardial space are thin and relatively avascular, the angle, spatial limitations, and orientation of the surgical access point relative to the pericardial reflections does not facilitate simple puncture with a blunt catheter or a standard needle. Moreover, the large vessel and cardiac chambers adjacent to the pericardial reflections make the proposition of blind puncture with conventional catheters impractical.

Accordingly, there is a need in the pertinent art for devices, systems, and methods for efficiently and reliably locating and puncturing pericardial reflections, e.g., for delivery of a guidewire and/or catheter.

SUMMARY

The embodiments of the present disclosure include devices and methods selective delivery of an ablation catheter to cardiac tissue. In some embodiments, an apparatus can include a first catheter defining a first longitudinal axis and a first lumen therethrough. A first actuator can be coupled to the first catheter and configured to rotate about the first longitudinal axis to deflect a distal end of the first catheter relative to the first longitudinal axis. A second catheter can define a second longitudinal axis and a second lumen therethrough. At least a portion of the second catheter can be configured to slide within the first lumen. A magnetic member can be coupled to a distal end of the second catheter. The magnetic member can define a third lumen therethrough. The third lumen can be in fluid communication with the second lumen. A second actuator can be coupled to the second catheter. The second actuator can be configured to move linearly along the second longitudinal axis so as to vary a spacing between the magnetic member and a distal end of the first catheter.

BRIEF DESCRIPTION OF THE DRAWINGS

FIG. 4 is a top view of a delivery device according to an embodiment.

FIG. 5 is a side view of a delivery device according to an embodiment.

FIG. 6 is a side view of the delivery device of FIG. 4 in a first configuration, shown without a portion of a handle to illustrate internal components of the delivery device.

FIG. 7 is side view of the delivery device of FIG. 5 in a second configuration, shown without a portion of a handle to illustrate internal components of the delivery device.

FIG. 26 is a schematic illustration of a kit, according to an embodiment.

DETAILED DESCRIPTION

Figure 1:
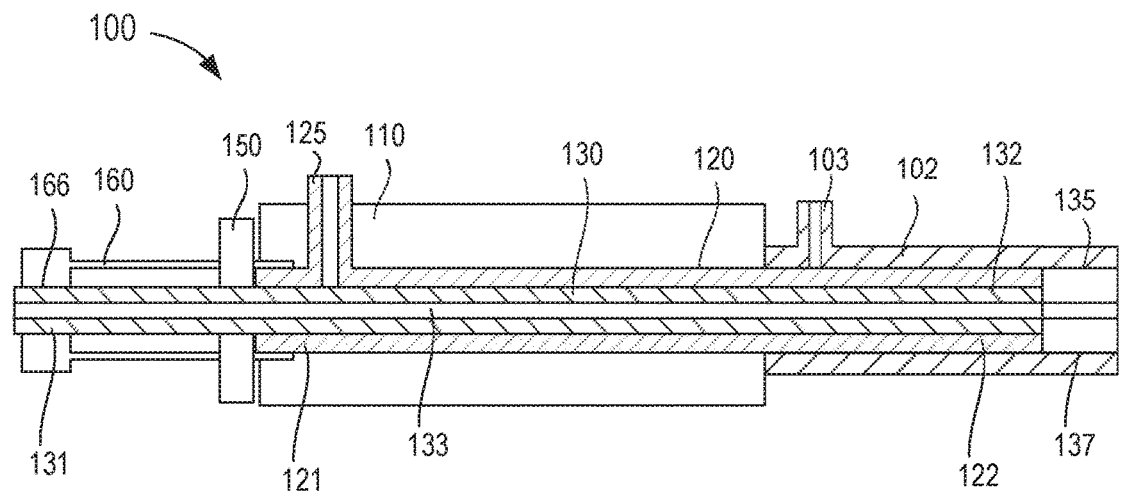
FIG. 1 is a schematic, cross-sectional illustration of a delivery device in a first configuration according to an embodiment.

In some embodiments, an apparatus includes a first catheter and a second catheter. In some embodiments, the first catheter can include a first port in fluid communication with a first lumen, and the second catheter can include a second port in fluid communication with a second lumen. The apparatus can also include a third catheter. The third catheter can define a third longitudinal axis and a fourth lumen therethrough. The third catheter can include a handle and a third port in fluid communication with the fourth lumen. The apparatus can be configured to transition between a first configuration and a second configuration in response to actuation of the second actuator. A distal end of the first catheter can be disposed within the third catheter in the first configuration. The distal end of the first catheter can be at least partially disposed distal to a distal end of the third catheter in the second configuration. A proximal end of the third catheter can include the third port.

In some embodiments, the magnetic member can include one or more of an electromagnet, a paramagnet, and a permanent magnet. The magnetic member can be at least partly constructed from radiopaque material. The first catheter and the magnetic member can have substantially the same diameter. The third lumen can be non-coaxial with a longitudinal axis of the magnetic member. A distal end of the magnetic member can include a convex or frustoconical shape. The second actuator can be coupled to a proximal end of the second catheter. The first actuator can be movably coupled to a proximal end of the handle. The rotation of the first actuator can be configured to deflect a distal end of the second catheter. The rotation of the first actuator can be configured to deflect a distal end of the third catheter.

In some embodiments, the first actuator can include a rotation member and a translation member. The rotation member can be coupled to a proximal end of the handle and the translation member can be movably disposed within the handle. Rotation of the rotation member can correspond to translation of the translation member along the first longitudinal axis. The translation member can be operably coupled to a distal end of the first catheter via a linkage.

In some embodiments, the third port can be configured to provide one or more of suction and lavage. The second actuator can include the second port. The second port, the second lumen, and the third lumen can be collectively configured to receive and advance a guidewire during use. The second actuator can include a push rod disposed within the first lumen and coupled to a proximal end of the second catheter. A lumen of the push rod can be in fluid communication with the second lumen. A lumen of the first port, the second lumen, and the lumen of the push rod can be co-axial.

In some embodiments, the handle can be configured for single-handed operation. The handle can be coupled to a proximal end of the third catheter. A conduit can define a lumen therethrough. The conduit can be configured to couple to a fluid source. The conduit can be at least partially disposed within the handle. The lumen of the conduit can be in fluid communication with the first lumen and fluidically isolated from the second lumen. At least a portion of the first catheter can be configured to slide within the fourth lumen. A proximal end of the first catheter can include the first port. The second and third lumen can be substantially the same diameter. A diameter of the first catheter can be between about 6 French and about 15 French. At least a portion of the second catheter can include a nickel-titanium alloy. A proximal end of the first catheter can be fixedly disposed within the handle.

In some embodiments, a proximal end of the first catheter includes a protrusion movably disposed within the second actuator. The second actuator can include a channel configured to movably receive the protrusion. A flexibility of the third catheter can be less than one or more of a flexibility of the first and second catheter. The flexibility of the first catheter can be less than the flexibility of the second catheter. The flexibility of the second catheter can be greater than the flexibility of the first and third catheter. The first catheter can have a bending stiffness between approximately $3 \times 10^{-5}$ Netwon-meters$^2$ and approximately $10^{-3}$ Netwon-meters$^2$. The second catheter can have a flexural modulus of about $3 \times 10^{-5}$ Netwon-meters$^2$ or less.

In some embodiments, a system can include a first device and second device. The first device can include a first catheter defining a first longitudinal axis and a first lumen therethrough. A first actuator can be coupled to the first catheter and configured to rotate about the first longitudinal axis to deflect a distal end of the first catheter relative to the first longitudinal axis. A second catheter can define a second longitudinal axis and a second lumen therethrough. At least a portion of the second catheter can be configured to slide within the first lumen. A first magnetic member can be coupled to a distal end of the second catheter. The first magnetic member can define a third lumen therethrough. The third lumen can be in fluid communication with the second lumen. A second actuator can be coupled to the second catheter. The second actuator can be configured to move linearly along the second longitudinal axis so as to vary a spacing between the first magnetic member and a distal end of the first catheter. The second device can include a fourth catheter defining a fourth longitudinal axis and a fourth lumen therethrough. A fourth actuator can be coupled to the fourth catheter and configured to rotate about the fourth longitudinal axis to deflect a distal end of the fourth catheter relative to the fourth longitudinal axis. A fifth catheter can define a fifth longitudinal axis and a fifth lumen therethrough. At least a portion of the fifth catheter can be configured to slide within the fourth lumen. A second magnetic member can be coupled to a distal end of the fifth catheter. The second magnetic member can define a sixth lumen therethrough. The sixth lumen can be in fluid communication with the fifth lumen. The second magnetic member can have a polarity opposite the first magnetic member such that the first and second magnetic members are configured to couple magnetically with the third lumen aligned to the sixth lumen. A fifth actuator can be coupled to the fifth catheter. The fifth actuator can be configured to move linearly along the fifth longitudinal axis so as to vary a spacing between the second magnetic member and a distal end of the fourth catheter.

In some embodiments, the first catheter can include a first port in fluid communication with the first lumen. The second catheter can include a second port in fluid communication with the second lumen. The first device can include a third catheter defining a third longitudinal axis and a lumen therethrough. The third catheter can include a handle and a third port in fluid communication with the lumen of the third catheter. The fourth catheter can include a fourth port in fluid communication with the fourth lumen. The fifth catheter can include a fifth port in fluid communication with the fifth lumen. The second device can include a sixth catheter defining a sixth longitudinal axis and a lumen therethrough. The sixth catheter can include a handle and a sixth port in fluid communication with the lumen of the sixth catheter. A distal end of the first magnetic member and a distal end of the second magnetic member can include complimentary shapes.

Also described here are methods. In general, these methods include the steps of inserting a first device into pericardial tissue of a heart of a subject such that a distal end of the first device is disposed within a pericardial space of the heart and on a first side of a first pericardial reflection. The first device can include a first catheter defining a first longitudinal axis and a first lumen therethrough. A second catheter can define a second longitudinal axis and a second lumen therethrough. At least a portion of the second catheter can be configured to slide within the first lumen. A first magnetic member can be coupled to a distal end of the second catheter. The first magnetic member can define a third lumen therethrough. The third lumen can be in fluid communication with the second lumen. A second device can be inserted into the pericardial tissue of the heart such that a distal end of the second device is disposed within the pericardial space on a second side of the first pericardial reflection opposite the first side. The second device can include a fourth catheter defining a fourth longitudinal axis and a fourth lumen therethrough. A fifth catheter can define a fifth longitudinal axis and a fifth lumen therethrough. At least a portion of the fifth catheter can be configured to slide within the fourth lumen. A second magnetic member can be coupled to a distal end of the fifth catheter. The second magnetic member can define a sixth lumen therethrough. The sixth lumen can be in fluid communication with the fifth lumen. The first magnetic member can be advanced to place the first magnetic member close to the first side of the first pericardial reflection. The second magnetic member can be advanced to place the second magnetic member close to the second side of the first pericardial reflection such that the first magnetic member couples to the second magnetic member across the first pericardial reflection via a magnetic force when the first magnetic member is close to the first side of the first pericardial reflection and the second magnetic member is close to the second side of the first pericardial reflection. A crossing wire can be advanced through the third lumen, the first pericardial reflection, and at least a portion of the sixth lumen to create an opening in the first pericardial reflection. A portion of one of the first and second magnetic members can be advanced through the opening and the first pericardial reflection.

In some embodiments, a guidewire can be advanced through the first lumen and the first pericardial reflection such that a portion of the guidewire is disposed on the second side of the first pericardial reflection. Advancing the first magnetic member can include actuating a first actuator of the first device. Actuating the first actuator can advance the second catheter relative to the first catheter. Actuating the first actuator can deflect a distal end of the first catheter. Advancing the second magnetic member can include actuating a second actuator of the second device. Actuating the second actuator can advance the fifth catheter relative to the fourth catheter. Actuating the second actuator can deflect a distal end of the second catheter. The opening in the first pericardial reflection can be dilated. The crossing wire can be withdrawn from the first pericardial reflection and the third lumen. The first and second devices disposed within the pericardial space can be fluoroscopically imaged.

In some embodiments, a method can include the steps of inserting a first device into pericardial tissue of a heart such that a distal end of the first device is disposed within a pericardial space of the heart and on a first side of a first pericardial reflection. The first device can include a first catheter defining a first longitudinal axis and a first lumen therethrough. A second catheter can define a second longitudinal axis and a second lumen therethrough. At least a portion of the second catheter can be configured to slide within the first lumen. A first magnetic member can be coupled to a distal end of the second catheter. The first magnetic member can define a third lumen therethrough. The third lumen can be in fluid communication with the second lumen. A second device can be inserted into the pericardial tissue of the heart such that a distal end of the second device is disposed within the pericardial space on a second side of the first pericardial reflection opposite the first side. The second device can include a fourth catheter defining a fourth longitudinal axis and a fourth lumen therethrough. A fifth catheter can define a fifth longitudinal axis and a fifth lumen therethrough. At least a portion of the fifth catheter can be configured to slide within the fourth lumen. A second magnetic member can be coupled to a distal end of the fifth catheter. The second magnetic member can define a sixth lumen therethrough. The sixth lumen can be in fluid communication with the fifth lumen. The first magnetic member can be advanced to place the first magnetic member close to the first side of the first pericardial reflection. The second magnetic member can be advanced to place the second magnetic member close to the second side of the first pericardial reflection such that the first magnetic member couples to the second magnetic member across the first pericardial reflection via a magnetic force when the first magnetic member is close to the first side of the first pericardial reflection and the second magnetic member is close to the second side of the first pericardial reflection. A crossing wire can be advanced through the third lumen, the first pericardial reflection, and at least a portion of the sixth lumen to create an opening in the first pericardial reflection. A portion of one of the first and second magnetic members can be advanced through the opening and the first pericardial reflection. The distal end of the first device can be advanced on a first side of a second pericardial reflection. The distal end of the second device can be advanced on a second side of the second pericardial reflection. The first magnetic member can be advanced to place the first magnetic member close to the first side of the second pericardial reflection. The second magnetic member can be advanced to place the second magnetic member close to the second side of the second pericardial reflection such that the first magnetic member couples to the second magnetic member across the second pericardial reflection via a magnetic force when the first magnetic member is close to the first side of the second pericardial reflection and the second magnetic member is close to the second side of the first second reflection. The crossing wire can be advanced through the third lumen, the second pericardial reflection, and at least a portion of the sixth lumen to create an opening in the second pericardial reflection. The portion of one of the first and second magnetic members can be advanced through the opening and the second pericardial reflection.

In some embodiments, the crossing wire can be withdrawn from the second pericardial reflection and the third lumen. A guidewire can be delivered through the third lumen, the opening in the first pericardial reflection, the opening in the second pericardial reflection, and the sixth lumen. The first and second devices can be withdrawn from a body of a subject while leaving the guidewire in place. A medical device can be advanced over the guidewire and through the openings in the first and second pericardial reflections. At least part of the left and right pulmonary veins can be encircled with the medical device. The medical device can include an ablation catheter. A circumferential ablation lesion can be formed using the ablation catheter. A guidewire can be advance through the first lumen and the second pericardial reflection such that a portion of the guidewire is disposed on the second side of the second pericardial reflection. The opening in the second pericardial reflection can be dilated. The first and second devices can be inserted into the pericardial tissue and include inserting an introducer catheter into a body of a subject. The first device can be inserted into the pericardial tissue and include advancing the first device along a transverse sinus of the heart. The second device can be inserted into the pericardial tissue and include advancing the second device along an oblique sinus of the heart.

In some embodiments, an apparatus includes a handle, a first catheter, a second catheter, a third catheter, a magnetic member, a first actuator, and a second actuator. The first catheter has a proximal end portion and a distal end portion and defines a lumen therethrough. The proximal end portion of the first catheter operably couples to the handle and includes a first port in fluid communication with the lumen of the first catheter. The second catheter has a proximal end portion and a distal end portion and defines a lumen therethrough. The second catheter is at least partially disposed within the lumen of the first catheter. The proximal end portion of the second catheter is fixedly disposed within the handle and includes a second port in fluid communication with the lumen of the second catheter. The third catheter has a proximal end portion and a distal end portion and defining a lumen therethrough. At least a portion of the third catheter is movably disposed within the lumen of the second catheter. The magnetic member is coupled to the distal end portion of the third catheter. The magnetic member defines a lumen extending therethrough that is in fluid communication with the lumen of the third catheter. The first actuator is coupled to the proximal end portion of the third catheter such that an access port of the first actuator is in fluid communication with the lumen of the third catheter. The first actuator is configured to be moved linearly relative to the housing to move the third catheter within the lumen of the second catheter between a proximal position, in which the magnetic member is adjacent to a distal surface of the second catheter, and a distal position, in which the magnetic member is distal to and spaced apart from the distal surface of the second catheter. The second actuator is operably coupled to the distal end portion of the second catheter such that rotation of the second actuator deflects the distal end portion of the second catheter in a non-linear direction.

In some embodiments, a system includes a first delivery device, a second delivery device, and a guidewire. The first delivery device includes a handle, a first catheter, a second catheter, and an actuator. The first catheter of the first delivery device has a proximal end portion disposed within the handle of the first delivery device and a distal end portion configured for insertion into the body and defines a lumen extending therethrough. The second catheter has a proximal end portion and a distal end portion and defines a lumen therethrough. The distal end portion of the second catheter of the first delivery device includes a magnetic member. At least a portion of the second catheter of the first delivery device is movably disposed within the lumen of the first catheter of the first delivery device. The actuator of the first delivery device is movably coupled to the proximal end portion of the second catheter of the first delivery device such that a port of the actuator is in fluid communication with the lumen of the second catheter. The actuator of the first delivery device is configured to move relative to the handle to place the magnetic member of the first delivery device adjacent to a first side of a target tissue when the distal end portion of the first catheter is inserted into the body. The second delivery device includes a handle, a first catheter, a second catheter, and an actuator. The first catheter of the second delivery device has a proximal end portion disposed within the handle of the second delivery device and a distal end portion configured for insertion into the body and defines a lumen extending therethrough. The second catheter has a proximal end portion and a distal end portion and defines a lumen therethrough. The distal end portion of the second catheter of the second delivery device includes a magnetic member having a length between approximately 2.0 millimeters (mm) and approximately 10.0 mm, including all values and sub-ranges in between. At least a portion of the second catheter of the second delivery device is movably disposed within the lumen of the first catheter of the second delivery device. The actuator of the second delivery device is movably coupled to the proximal end portion of the second catheter of the second delivery device such that a port of the actuator is in fluid communication with the lumen of the second catheter. The actuator of the second delivery device is configured to move relative to the handle to place the magnetic member of the second delivery device adjacent to a second side of the target tissue when the distal end portion of the first catheter is inserted into the body. The guidewire is configured to be inserted, via the port of the actuator of the first delivery device, through the second catheter of the first delivery device, the target tissue, and at least a portion of the second catheter of the second delivery device. The guidewire is configured to define a path circumscribing at least a portion of an anatomic structure.

In some embodiments, a method includes inserting a delivery catheter of a first delivery device into pericardial tissue of a heart such that a distal end portion of the delivery catheter is disposed within a pericardial space of the heart and on a first side of a pericardial reflection. A delivery catheter of a second delivery device is inserted into the pericardial tissue of the heart such that a distal end portion of the delivery catheter of the second delivery device is disposed within the pericardial space on a second side of the pericardial reflection opposite the first side. An actuator of the first delivery device is actuated to advance a magnetic member of the first delivery device relative to the delivery catheter of the first delivery device to place the magnetic member of the first delivery device close to the first side of the pericardial reflection.

The term "close to", as used herein with reference to separation between a pericardial reflection and one or more catheter components, and can encompass an absolute distance or a relative distance. The absolute distance can be from about 0 mm to about 30 mm, including all values and sub-ranges in between. The relative distance can be relative to a dimension of a particular catheter component. For example, if the magnetic member has a length (say) L (for example, L can have a value in the range between about 2 mm and about 11 mm), the tip of the magnetic member can be less than about a distance about four times the length L (4*L) from the pericardial reflection when the magnetic member is "close to" the pericardial reflection.

An actuator of the second delivery device is actuated to advance a magnetic member of the second delivery device relative to the delivery catheter of the second delivery device to place the magnetic member of the second delivery device close to the second side of the pericardial reflection. The magnetic member of the first delivery device and the magnetic member of the second delivery device are coupled via a magnetic coupling when the magnetic member of the first delivery device is close to the first side of the pericardial reflection and the magnetic member of the second delivery device is close to the second side of the pericardial reflection (e.g., if the magnetic member of the second delivery device has a length, the tip of the magnetic member can be less than about a distance of approximately four times the length L (4*L) from the second side of the pericardial reflection). A needle (e.g., a trocar, stylet, wire, and/or other sharpened elongate member) is advanced through a lumen of the magnetic member of the first delivery device, the pericardial reflection, and at least a portion of a lumen of the magnetic member of the second delivery device. The opening defined in the pericardial reflection as a result of the advancing the needle is dilated. A portion of the delivery catheter of the first delivery device is advanced through the opening defined in the pericardial reflection to place the magnetic member of the first delivery device on the second side of the pericardial reflection. A guidewire is then advanced through the lumen of the delivery catheter of the first delivery device and the pericardial reflection such that a portion of the guidewire is disposed on the second side of the pericardial reflection.

In some embodiments, a method includes positioning a distal end of a first delivery catheter proximate to a first side of a first pericardial reflection of a subject. The first delivery catheter has a lumen extending therethrough. A first catheter of a first device is disposed in the lumen of the first delivery catheter. The first catheter of the first device is extended towards the first pericardial reflection to lie outside a distal portion of the first delivery catheter. The first catheter having a lumen extending therethrough. A second catheter of the first device disposed in the first lumen of the first catheter. The second catheter of the first device is extended towards the first pericardial reflection to lie outside a distal portion of the first catheter of the first device such that the second catheter of the first device contacts the first pericardial reflection. A distal end portion of a second delivery catheter is positioned proximate to a second side of the first pericardial reflection of the subject. The second delivery catheter has a lumen extending therethrough. A first catheter of a second device is disposed in the lumen of the second delivery catheter. The first catheter of the second device is extended towards the first pericardial reflection to lie outside a distal portion of the second delivery catheter. The first catheter of the second device has a lumen extending therethrough. A second catheter of the first device is disposed in the lumen of the first catheter. The second catheter of the second device is extended towards the first pericardial reflection to lie outside a distal portion of the first catheter of the second device such that the second catheter of the second device contacts the first pericardial reflection. A first magnet assembly of the second catheter of the first device and a second magnet assembly of the second catheter of the second device are magnetically coupled across the first pericardial reflection when the second catheter of the second device is extended such that the lumen of the second catheter of the first device is substantially axially aligned with the lumen of the second catheter of the second device. The first pericardial reflection is pierced by advancing a sharpened guidewire through the lumen of the second catheter of the first device, through the first pericardial reflection, and into the lumen of the second catheter of the second device to define a pierced portion in the first pericardial reflection. The sharpened guidewire is withdrawn from the lumen of the second catheter of the second device and from the first pericardial reflection. The second catheter of the first device is withdrawn into the first catheter of the first device and the first catheter of the first device is withdrawn into the first delivery catheter. The second catheter of the second device is withdrawn into the first catheter of the second device and the first catheter of the second device is withdrawn into the second delivery catheter. The distal end portion of the first delivery catheter is positioned proximate to a first side of a second pericardial reflection of the subject. The first catheter of the first device is extended from the first delivery catheter towards the second pericardial reflection to lie outside the distal portion of the first delivery catheter. The second catheter of the first device is extended towards the second pericardial reflection to lie outside the distal portion of the first catheter of the first device such that the second catheter of the first device contacts the second pericardial reflection. A distal end of the second delivery catheter is positioned proximate to a second side of the second pericardial reflection of the subject. The first catheter of the second device is extended from the second delivery catheter towards the second pericardial reflection to lie outside the distal portion of the second delivery catheter. The second catheter of the second device is extended towards the second pericardial reflection to lie outside the distal portion of the first catheter of the second device such that the second catheter of the second device contacts the first pericardial reflection. The first magnet assembly of the second catheter of the first device and the second magnet assembly of the second catheter of the second device are magnetically coupled across the second pericardial reflection when the second catheter of the second device is extended such that the lumen of the second catheter of the first device is substantially axially aligned with the lumen of the second catheter of the second device. The second pericardial reflection is pierced by advancing the sharpened guidewire through the lumen of the second catheter of the first device, through the second pericardial reflection, and into the lumen of the second catheter of the second device to define a pierced portion in the second pericardial reflection. The sharpened guidewire is then withdrawn from the lumen of the second catheter and from the second pericardial reflection. A guidewire is delivered through the lumen of the second catheter of the first device, the pierced portion in the first pericardial reflection, the pierced portion in the second pericardial reflection, and the lumen of the second catheter of the second device. The first device, the first delivery catheter, the second device, and the second catheter are withdrawn from the body of the subject while leaving the guidewire in place. A medical device is then positioned in the pericardial space of the heart of the subject by passing the medical device over the guidewire, through the pierced portion of the first pericardial reflection, and through the pierced portion of the second pericardial reflection, such that a central portion of the medical device at least partially encircles the left pulmonary veins and the right pulmonary veins.

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the words "a" or "an" and the phrase "one or more" can be used interchangeably.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. In general, the term "or" as used herein should be interpreted as exclusive when the context explicitly indicates exclusivity is intended (e.g., when "or" is used in conjunction with terms of exclusivity such as "one of," "only one of," etc.).

As used herein, the words "proximal" and "distal" refer to direction closer to and away from, respectively, an operator of the medical device. Thus, for example, the end of a catheter or delivery device contacting the patient's body would be the distal end of the medicament delivery device, while the end opposite the distal end (i.e., the end operated by the user) would be the proximal end of the catheter or delivery device.

As used herein, the terms "about" and/or "approximately" when used in conjunction with numerical values and/or ranges generally refer to those numerical values and/or ranges near to a recited numerical value and/or range. In some instances, the terms "about" and "approximately" can mean within ±10% of the recited value. For example, in some instances, "about 100 [units]" can mean within ±10% of 100 (e.g., from 90 to 110). The terms "about" and "approximately" can be used interchangeably.

In a similar manner, term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±1%, ±2%, ±3%, ±4%, ±5%, ±6%, ±7%, ±8%, ±9%, or ±10% of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

As used herein, the term "stiffness" is related to an object's resistance to deflection, deformation, and/or displacement that is produced by an applied force, and is generally understood to be the opposite of the object's "flexibility." For example, a wall with greater stiffness is more resistant to deflection, deformation, and/or displacement when exposed to a force than a wall having a lower stiffness. Similarly stated, an object having a higher stiffness can be characterized as being more rigid than an object having a lower stiffness. Stiffness can be characterized in terms of the amount of force applied to the object and the resulting distance through which a first portion of the object deflects, deforms, and/or displaces with respect to a second portion of the object. When characterizing the stiffness of an object, the deflected distance can be measured as the deflection of a portion of the object different from the portion of the object to which the force is directly applied. Said another way, in some objects, the point of deflection is distinct from the point where force is applied.

Stiffness (and therefore, flexibility) is an extensive property of the object being described, and thus is dependent upon the material from which the object is formed as well as certain physical characteristics of the object (e.g., cross-sectional shape, length, boundary conditions, etc.). For example, the stiffness of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the stiffness of the object can be decreased, for example, by introducing into the object and/or constructing the object of a material having a relatively low modulus of elasticity. In another example, the stiffness of the object can be increased or decreased by changing the flexural modulus of a material of which the object is constructed.

Flexural modulus is used to describe the ratio of the applied stress on an object in flexure to the corresponding strain in the outermost portions of the object. The flexural modulus, rather than the modulus of elasticity, is used to characterize certain materials, for example plastics, that do not have material properties that are substantially linear over a range of conditions. An object with a first flexural modulus is less elastic and has a greater strain on the outermost portions of the object than an object with a second flexural modulus lower than the first flexural modulus. Thus, the stiffness of an object can be increased by including in the object a material having a high flexural modulus.

The stiffness of an object can also be increased or decreased by changing a physical characteristic of the object, such as the shape or cross-sectional area of the object. For example, an object having a length and a cross-sectional area can have a greater stiffness than an object having an identical length but a smaller cross-sectional area. As another example, the stiffness of an object can be reduced by including one or more stress concentration risers (or discontinuous boundaries) that cause deformation to occur under a lower stress and/or at a particular location of the object. Thus, the stiffness of the object can be decreased by decreasing and/or changing the shape of the object.

The embodiments described herein can be formed or constructed of one or more biocompatible materials. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A biocompatible polymer material can be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof. While specific examples of materials are listed above, it should be understood that the list is not exhaustive and thus, some embodiments described herein can be formed of biocompatible materials other than those listed. Moreover, any of the embodiments and/or components described herein can be formed of and/or can include a material that is visible under known imaging techniques such as, for example, X-Ray, fluoroscopy, computed tomography (CT), etc. For example, in some embodiments, one or more components can be formed of and/or can include a radiopaque material, such as a radiopaque band and/or marker.

The embodiments can include, be used with, and/or used to place devices in the pericardial space, such as devices including one or more electrodes and/or electrode portions. Any of the electrodes or electrode portions described herein can be constructed from any suitable material having any suitable range of electrical conductivity. For example, any of the electrode portions described herein can be constructed from silver, palladium, stainless steel, titanium, platinum, nickel, and any alloys thereof. The electrodes and/or electrode portions described herein can be constructed using any suitable procedures. In some embodiments, the electrode materials with chosen electrical conductivities can be plated, coated, and/or otherwise applied in an appropriately thick layer on top of a different substrate material. In other embodiments, electrode portions can be coupled together using annealing, soldering, welding, crimping, and/or lamination to ensure good electrical contact at all interfaces.

Figure 2:
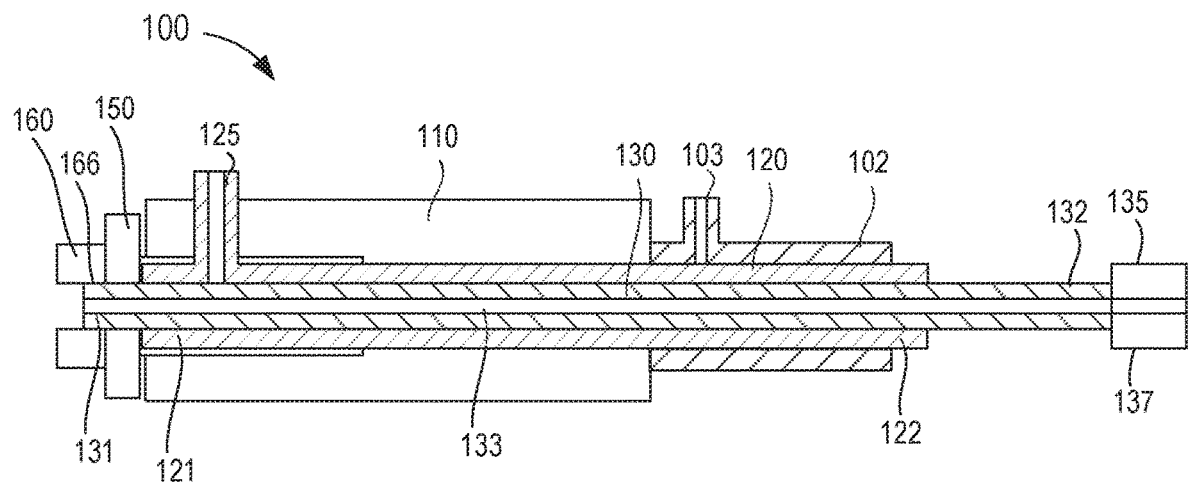
FIG. 2 is a schematic, cross-sectional illustration of a delivery device in a second configuration according to an embodiment.

FIGS. 1 and 2 are schematic illustrations of a delivery device 100 (also sometimes referred to herein as a "first device") in a first configuration and a second configuration, respectively, according to an embodiment. As described herein, the delivery device 100 can be used to deliver a catheter, guidewire, needle, etc. to a target tissue. In some instances, for example, the delivery device 100 can be used with a second delivery device 100' (also sometimes referred to herein as a "second device") substantially similar to the delivery device 100 to place a guidewire and/or a catheter in, at, and/or around a target tissue (see e.g., FIG. 3). By way of example, the delivery device(s) 100 and/or 100' can be used to place a guidewire within the pericardial space and about the pulmonary veins of a heart. In some instances, an ablation catheter or the like can be advanced along the guidewire and once placed, can be used to produce a circumferential ablation lesion suitable to treat, for example, atrial fibrillation, and/or the like. In some embodiments, portions of the delivery device 100 can be similar in form and/or function to those described in PCT Patent Publication No. WO2014/025394 entitled, "Catheters, Catheter Systems, and Methods for Puncturing Through a Tissue Structure," filed Mar. 14, 2013, the disclosure of which is incorporated herein by reference in its entirety and presented herewith as Exhibit A. As such, some portions of the delivery device(s) 100 and/or 100' are not described in further detail herein. In some instances, the delivery devices 100 and 100' can be similar or substantially the same, while in other instances, the delivery devices 100 and 100' can be structurally and/or functionally different, based on the intended use of the respective device. For example, a device placed in a longer route to reach its intended target can be longer than one intended to traverse a shorter distance. The discussion of the delivery device 100 is intended to apply equally to the delivery device 100' unless clearly indicated otherwise.

As shown in FIGS. 1 and 2, the delivery device 100 (includes a handle 110, a delivery catheter 102 (also sometimes referred to herein as a "third catheter"), a first catheter 120, a second catheter 130, a magnetic member 135, a first actuator 150, and a second actuator 160. The handle 110 can be any suitable shape, size, and/or configuration. In some embodiments, for example, the handle 110 can have a size and/or shape suitable for single-handed operation (either left hand or right hand operation). In some embodiments, the size and/or shape of the handle 110 can be configured to increase the ergonomics and/or ease of use of the device 100.

The delivery catheter 102 can be any suitable shape, size, and/or configuration. The delivery catheter 102 has a proximal end portion and a distal end portion and defines a lumen therethrough. In some embodiments, the proximal end portion of the delivery catheter 102 is coupled to the handle 110. In other embodiments, the delivery catheter 102 can be included in and/or coupled to any suitable portion of the device other than the handle 110. The proximal end portion of the delivery catheter 102 includes and/or defines a port 103 (also sometimes referred to as "third port") in fluid communication with the lumen. The port 103 can be used to provide (e.g., lavage) or withdraw (e.g., suction) a fluid through the lumen of the delivery catheter 103, which in some instances, can facilitate the advancement of the delivery catheter 102 through portions of the body. As shown in FIGS. 1 and 2, the lumen of the delivery catheter 102 movably receives at least a portion of the first catheter 120, the second catheter 130, and the magnetic member 135. In other words, the delivery catheter 102 is disposed about at least a portion of the first catheter 120, the second catheter 130, and the magnetic member 135.

In some embodiments, the delivery catheter 102 can be formed of a relatively flexible material such as any of those described herein. In some embodiments, for example, the delivery catheter 102 can be formed from one or more materials and can have a flexibility that is lesser than a flexibility of the first catheter 120 and/or the second catheter 130. In this manner, the delivery catheter 102 can be configured to support, protect, and/or otherwise deliver the distal end portions of the catheters 120 and 130 and the magnetic member 135 to a desired position within a portion of the body. In some embodiments, at least a portion of the delivery catheter 102 can be non-linear (e.g., can have and/or can define one or more curved sections). For example, in some instances, the delivery catheter 102 can be curved in such a manner as to facilitate access to epicardial or pericardial locations on an anterior and/or posterior surface(s) of the heart. Specifically, in some instances, the delivery catheter 102 can be inserted into and advanced through the pericardial space of a heart to place, for example, the magnetic member 135 close to a pericardial reflection (e.g., within about four times the length of the magnetic member), as described in further detail herein with reference to specific embodiments.

The first catheter 120 can be any suitable catheter configured to be inserted into a portion of a patient. For example, the first catheter 120 can be relatively flexible to allow a portion of the first catheter 120 to bend, flex, deflect, and/or otherwise elastically deform as the first catheter 120 is advanced within a portion of the body. In some embodiments, the first catheter 120 can have a flexibility that is greater than a flexibility of the delivery catheter 102 but less than a flexibility of the second catheter 130, as described in further detail herein. Moreover, the first catheter 120 can have a size (e.g., diameter) that is associated with and/or otherwise suitable for insertion into the handle 110 and/or the delivery catheter 102.

The first catheter 120 has a proximal end portion 121 and a distal end portion 122 and defines a first longitudinal axis and a first lumen therethrough. The proximal end portion 121 of the first catheter 120 is fixedly disposed within the handle 110. In other embodiments, the proximal end portion 121 of the first catheter 120 can be movably coupled to and/or movably disposed in the handle 110. In some instances, as illustrated, the proximal end portion 121 of the first catheter 120 includes, defines, and/or is otherwise coupled to a port 125 (also sometimes referred to as "first port"). The port 125 is in fluid communication with the lumen of the first catheter 120 and can be used to provide (e.g., lavage) or withdraw (e.g., suction) a fluid through the lumen of the first catheter 120. The distal end portion 122 of the first catheter 120 is disposed distal to and outside of the handle 110 and is at least partially and/or at least temporarily disposed within a lumen defined by the delivery catheter 102, as described in further detail herein. For example, in some instances, the distal end portion 122 of the first catheter 120 can be disposed within the lumen (also sometimes referred to as a "fourth lumen") of the delivery catheter 102 when the device 100 is in the first configuration (e.g., FIG. 1) and can be partially disposed within the lumen of the delivery catheter 102 and extend distal thereto when the device 100 is in the second configuration (e.g., FIG. 2). As described in further detail herein, the distal end portion 122 of the first catheter 120 is operably coupled to the first actuator 150 such that actuation of the first actuator 150 results in a deflection of at least the distal end portion 122 of the first catheter 120. A proximal end of the first catheter can be configured to slide within the fourth lumen.

The second catheter 130 can be any suitable catheter configured to be inserted into a portion of the patient and can have a size (e.g., diameter) that is associated with and/or otherwise suitable for insertion into the lumen of the first catheter 120. In addition, the second catheter 130 can be formed of a relatively flexible material (e.g., a material having a relatively low stiffness) such as any of those described above. In some embodiments, for example, the second catheter 130 can have a stiffness that is less than a stiffness of the first catheter 120 (and less than a stiffness of the delivery catheter 102). In other words, in some embodiments, the second catheter 130 can be more flexible than the first catheter 120 and the delivery catheter 102. Said another way, the second catheter 130 can be the most flexible catheter 130 included in the delivery device 100. At least a portion of the second catheter 130 can be configured to slide within the first lumen.

The second catheter 130 has a proximal end portion 131 and a distal end portion 132 and defines a second longitudinal axis and a second lumen 133 therethrough. As shown in FIGS. 1 and 2, the distal end portion 132 of the second catheter 130 is coupled to the magnetic member 135 such that a third lumen 137 of the magnetic member 135 is in fluid communication with the second lumen 133 of the second catheter 130, as described in further detail herein. While the lumens 133 and 137 are shown in FIGS. 1 and 2 as having substantially the same diameter, in other embodiments, a second lumen 133 of the second catheter 130 can have a diameter that is less than or, alternatively, that is greater than, a diameter of the third lumen 137 of the magnetic member 135. The proximal end portion 131 of the second catheter 130 is coupled to the second actuator 160 such that the second catheter 130 is moved within the first lumen of the first catheter 120 between a first position (e.g., FIG. 1) and a second position (e.g., FIG. 2) in response to an actuation of the second actuator 160, as described in further detail herein. The device can be configured to transition between a first configuration and a second configuration in response to actuation of the second actuator 160. A distal end of the first catheter can be disposed within the third catheter in the first configuration. The distal end of the first catheter can be at least partially disposed distal to a distal end of the third catheter in the second configuration. Additionally or alternatively, the device can be configured to transition between any suitable number of configurations (e.g., one, two, three, four, or more configurations), and can transition between any two configurations in a stepwise manner or continuous manner.

As described above, the magnetic member 135 is included in and/or coupled to the distal end portion 132 of the second catheter 130. For example, in some embodiments, the magnetic member 135 is coupled to the distal end portion 132 of the second catheter 130 via a weld, adhesive, and/or mechanical fastener. In other embodiments, the magnetic member 135 can be integrally formed with the distal end portion 132 of the second catheter 130 (e.g., co-molded, over-molded, etc.). In still other embodiments, the distal end portion 132 of the second catheter 130 can be at least partially formed of a magnetic constituent material or the like. Moreover, the arrangement of the second catheter 130 and the magnetic member 135 is such that the second lumen 133 of the second catheter 130 is in fluid communication with the third lumen 137 of the magnetic member 135. More particularly, as shown in FIGS. 1 and 2, the lumens 133 and 137 can be aligned and/or co-axial.

The magnetic member 135 can be any suitable shape, size, and/or configuration. In some embodiments, the magnetic member 135 can be, for example, an electromagnet, a paramagnet, a permanent magnet, and/or any other suitable magnetic member. The magnetic member 135 can be formed of any suitable magnetic material and/or any material capable of being magnetized. Moreover, the magnetic member 135 can be formed of a material configured to be visible within a portion of the body via fluoroscopic imaging techniques (e.g., a radiopaque material or the like). In some embodiments, the magnetic member 135 can be polygonal (e.g., triangular, square, rectangular, pentagonal, etc.), rounded (e.g., semi-circular, circular, elliptical, oblong, etc.), and/or a combination thereof. In some embodiments, the magnetic member 135 can be at least partially cylindrical or the like and can have a diameter that is substantially similar to a diameter of the first catheter 120 (see e.g., FIG. 1). In some embodiments, the magnetic member 135 can have a size and/or shape configured to be matingly coupled to a corresponding magnetic member of a second (e.g., separate) delivery device. In some embodiments, the size and/or shape of the magnetic member 135 can increase and/or otherwise direct a magnetic flux or force operable to increase a likelihood of a magnetic coupling between the magnetic member 135 and a corresponding magnetic member through a target tissue (e.g., magnetically coupled such that a portion of the target tissue is disposed therebetween), as described in further detail herein. For example, in some embodiments, when the magnetic member 135 is placed in a desired position relative to a first side of the target tissue (e.g., placed at a distance that is within about four times the length of the magnetic member 135) and a corresponding magnetic member (e.g., the magnetic member 135' of FIG. 3) is placed in a similar position relative to a second side of the target tissue (opposite the first side), a force operable to magnetically couple the magnetic members can be sufficient to bend, flex, and/or move the distal end portion 132 of the second catheter 130 to allow the magnetic members 135, 135' to couple together.

The first actuator 150 can be any suitable shape, size, and/or configuration. The first actuator 150 is movably coupled to the proximal end portion of the handle 110 and operably coupled to the distal end portion 122 of the first catheter 120. For example, in some embodiments, the first actuator 150 is configured to rotate relative to the handle 110 and about the second actuator 160 (e.g., the second actuator 160 defines an axis of rotation). In other embodiments, the first actuator 150 can be coupled to the handle 110 in any suitable manner and/or position. The first actuator 150 can be operably coupled to the distal end portion 122 of the first catheter 120 in any suitable manner. For example, in some embodiments, the first actuator 150 is operably coupled to the distal end portion 122 of the first catheter 120 via a wire, tether, and/or any other suitable linkage. In this manner, movement of the first actuator 150 relative to the handle 110 results in movement of the distal end portion 122 of the first catheter 120, which in turn, can result in movement of the second catheter 130. For example, in some embodiments, rotation of the first actuator 150 relative to the handle 110 results in an elastic deformation and/or a deflection (e.g., bending, curving, twisting, and/or any other suitable reconfiguration) of the distal end portion 122 of the first catheter 120. Said another way, the first actuator 150 can be coupled to the first catheter 120 and configured to rotate about the first longitudinal axis to deflect a distal end of the first catheter 120 relative to the first longitudinal axis. Moreover, with the second catheter 130 at least partially disposed in the lumen of the first catheter 120, the deflection of the first catheter 120 can result in an associated and/or similar deflection of the second catheter 130. Thus, in some instances, deflection of the distal end portion 122 of the first catheter 120, for example, can facilitate the placement of the magnetic member 135 within a desired portion of the body, as described in further detail herein.

In some embodiments, forming the first catheter 120 from a relatively flexible material can allow for steering and/or fine control of the distal end portion 122 of the first catheter 120 during placement near and/or at a target location and/or tissue within the body such as, for example, a pericardial reflection, as described herein. In some instances, the first actuator 150 can be actuated while the distal end portion 122 of the first catheter 120 is disposed within the lumen of the delivery catheter 102, which in turn, can result in deflection of both the distal end portion of the delivery catheter 102 and the distal end portion 122 of the first catheter 120 (as well as the second catheter 130 disposed within the first catheter 120, as described above). That is to say, the delivery catheter 102 can be formed of a material that is sufficiently flexible to allow the distal end portion of the delivery catheter 102 to deflect when the distal end portion 122 of the first catheter 120 is disposed therein and in response to an actuation of the first actuator 150. In other embodiments, the delivery catheter 102 can be formed of a material that is not sufficiently flexible (e.g., a stiffness of the material is too large) to deflect in response to the deflection of the first catheter 120. In other words, a force associated with a deflection of the distal end portion 122 of the first catheter 120, in response to an actuation of the first actuator 150, is not sufficient to deflect the distal end portion of the delivery catheter 102 when disposed therein.

The second actuator 160 is coupled to the proximal end portion 131 of the second catheter 130 and is configured to move the second catheter 130 relative to the first catheter 120. For example, in some embodiments, the second actuator 160 is slidably and/or movably coupled to a proximal end portion of the handle 110 and is configured to move linearly in a proximal and/or distal direction to move the second catheter 130 between a first position (e.g., a proximal position as shown in FIG. 1) and a second position (e.g., a distal position as shown in FIG. 2). Said another way, the second actuator 160 can be configured to move linearly along the second longitudinal axis so as to vary a spacing between the magnetic member 135 and a distal end of the first catheter 120.

The second actuator 160 includes and/or defines an access port 166 that is in fluid communication with the lumen 133 of the second catheter 130. In this manner, any suitable member, device, substance, and/or the like can be delivered to and/or withdrawn from the lumen 133 of the second catheter 130. For example, in some instances, a needle and/or a guidewire can be inserted into the access port 166 of the second actuator 160 and advanced through the lumen 133 of the second catheter 130 and/or the lumen 137 of the magnetic member 135. More specifically, in some instances, a needle and/or a sharpened guidewire can be inserted into the access port 166 and through the lumens 133 and 137 to pierce, puncture, and/or otherwise define an opening in, for example, a pericardial reflection. Similarly, once the pericardial reflection is pierced, a guidewire (e.g., a non-sharpened guidewire) can be inserted into the access port 166 and advanced through the lumens 133 and 137 and the opening in the pericardial reflection. As such, a catheter and/or the like can be advanced along the guidewire and through the opening in the pericardial reflection, as described in further detail herein.

As described above, the device 100 can be used to deliver a guidewire, a catheter, and/or the like to any suitable target location within, for example, a body. More specifically, the device 100 can be used with a corresponding device such as the device 100' shown in FIG. 3 collectively to deliver a guidewire, catheter, and/or the like. By way of a specific example, the devices 100 and 100' can be used to deliver a guidewire to a desired position within the pericardial space of a heart such that the guidewire circumscribes and/or is otherwise positioned around the pulmonary veins. In the example described herein with reference to FIG. 3, the devices 100 and 100' (e.g., a first device 100 and a second device 100', respectively) are substantially the same and thus, the components of the device 100' are substantially the same as the corresponding components in the device 100 and are referred to using the same reference characters with prime notation.

In some instances, a user (e.g., surgeon, technician, interventionalist, doctor, etc.) can insert the delivery catheter 102 and 102' of each device 100 and 100', respectively, into a body of a patient and can position the distal end portion of each deliver catheter 102 and 102' in a desired position relative to a target tissue T. More specifically, a user can advance the delivery catheter 102 of the first device 100 to dispose a distal end of the delivery catheter 102 of the first device 100 on a first side of the target tissue T (e.g., a first or superior pericardial reflection) and can advance the delivery catheter 102' of the second device 100' to dispose a distal end of the deliver catheter 102' of the second device 100' on a second side of the target tissue T.

The user can then manipulate the first device 100 to advance the first catheter 120, the second catheter 130, and the magnetic member 135 in a distal direction relative to the delivery catheter 102 and toward the target tissue T. In some instances, the user can manipulate the first actuator 150 of the first device 100 concurrently (or in one or more separate processes) as the first catheter 120, the second catheter 130, and the magnetic member 135 are advanced (e.g., collectively) relative to the delivery catheter 102 to advance and/or steer the first catheter 120, the second catheter 130, and the magnetic member 135 toward the first side of the target tissue T. Similarly, the first catheter 120', the second catheter 130', and the magnetic member 135' of the second device 100' can be advanced and/or steered toward the second side of the target tissue T. In some instances, for example, the first catheter 120, the second catheter 130, and the magnetic member 135 of the first device 100 can be advanced and/or steered within the pericardial space toward a first or superior pericardial reflection.

Figure 3:
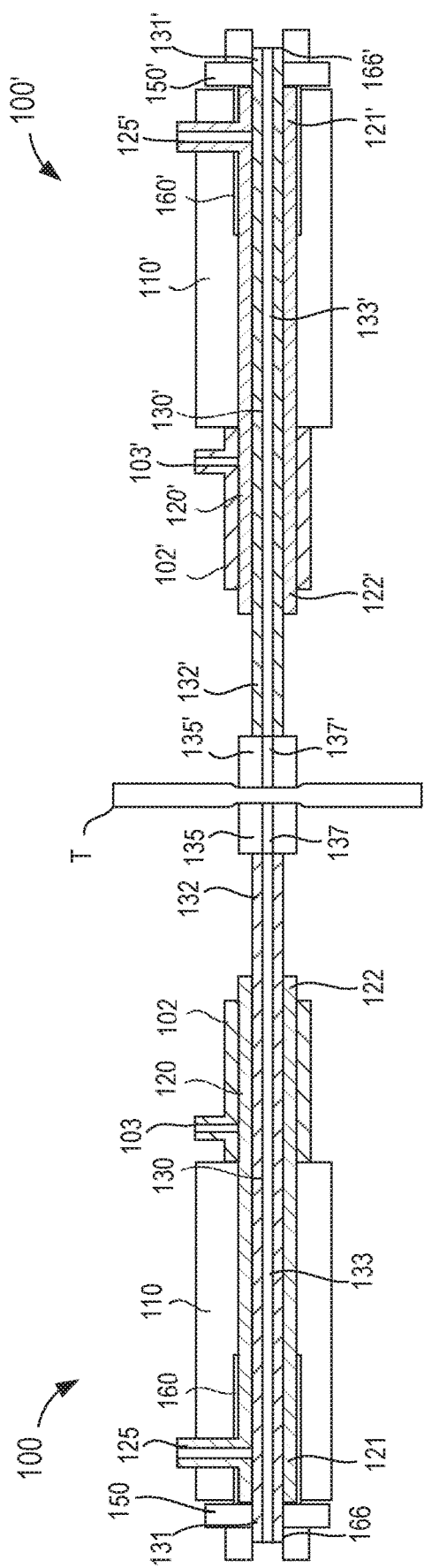
FIG. 3 is a schematic illustration of the delivery device of FIGS. 1 and 2 and a second delivery device, which are coupled together with a portion of a target tissue disposed therebetween.

As shown in FIG. 3, in some instances, the distal end portions 122 and 122' of the first catheters 120 and 120', respectively, can be advanced and/or steered toward the target tissue T to positions in which an attractive magnetic force between the magnetic members 135 and 135' results in a magnetic coupling of the magnetic member 135 of the first device 100 to the magnetic member 135' of the second device 100' with a portion of the target tissue T disposed therebetween. As described in further detail herein with reference to specific embodiments, the arrangement, shape, size, and/or configuration of the magnetic members 135 and/or 135' can be configured to facilitate and/or enhance a coupling of the magnetic members 135 and 135' and/or an alignment of the magnetic members 135 and 135' once coupled. As a specific example, the first catheter 120 of the first device 100 can be placed in a desired position on a first side of a first or superior pericardial reflection and the first catheter 120' of the second device 100' can be placed in a desired position on a second side of the first or superior pericardial reflection such that a magnetic coupling is formed between the magnetic member 135 of the first device 100 and the magnetic member 135' of the second device 100' with a portion of the first or superior pericardial reflection disposed therebetween.

After magnetically coupling the magnetic members 135 and 135' (e.g., through the target tissue T, as shown in FIG. 3), the user can advance, for example, a needle or a sharpened guidewire (not shown in FIGS. 1-3) through the access port 166 of the second actuator 160, the lumen 133 of the second catheter 130, and the lumen 137 of the magnetic member 135 of the first device 100 (or, alternatively, the second device 100') to pierce the portion of the target tissue T disposed between the magnetically coupled magnetic members 135 and 135'. The user can then retract the needle and/or sharpened guidewire and can subsequently advance a guidewire (not shown in FIGS. 1-3) through the access port 166 of the second actuator 160, the lumen 133 of the second catheter 130, and the lumen 137 of the magnetic member 135 of the first device 100, through the opening defined in the target tissue T, and into the lumen 137' of the magnetic member 135' and the lumen 133' of the second catheter 130' of the second device 100'. In other instances, a user need not insert a guidewire after piercing the target tissue T.

At least the first catheter 120, the second catheter 130, and the magnetic member 135 of the first device 100 can be advanced through the opening in the target tissue T (e.g., advanced along the placed guidewire). In some instances, the user can advance a dilation catheter or the like into the opening of the target tissue T (e.g., along the guidewire or without the use of the guidewire) prior to advancing at least the first catheter 120, the second catheter 130, and the magnetic member 135 of the first device 100. In this manner, the dilation catheter can be actuated to dilate the opening defined in the target tissue T to a suitable size to receive at least the first catheter 120, the second catheter 130, and the magnetic member 135 of the first device 100 therethrough.

In some instances, once the first catheter 120, the second catheter 130, and the magnetic member 135 of the first device 100 are advanced through the target tissue T, the first catheters 120 and 120', the second catheters 130 and 130', and the magnetic members 135 and 135' (within or distal to the respective delivery catheters 102 and 102') can then be positioned relative to a second target tissue (not shown in FIG. 3) in a substantially similar manner as described above with reference to the target tissue T. For example, the first catheters 120 and 120', the second catheters 130 and 130', and the magnetic members 135 and 135' can be positioned (as described above) in desired positions relative to a second or posterior pericardial reflection. As such, the user can manipulate the second actuators 160 and 160' of the devices 100 and 100', respectively, as described above, to magnetically couple the magnetic members 135 and 135' such that a portion of the second or posterior pericardial reflection is disposed therebetween. The user can then advance the needle or sharpened guidewire (not shown) to pierce the second or posterior pericardial reflection and after retracting the needle, can subsequently advance the guidewire through the opening defined by the second or posterior pericardial reflection. In some instances, advancing the guidewire through the first or superior pericardial reflection and the second or posterior pericardial reflection can be such that the guidewire is disposed and/or positioned about the pulmonary veins. In some instances, such as procedures and/or surgeries for treating atrial fibrillation, an ablation catheter, for example, can be advanced along the guidewire to be disposed around and/or about the pulmonary veins. Thus, the devices 100 and 100' can be used to place an ablation catheter within the pericardial space such that the ablation catheter circumscribes a portion of the pulmonary veins. The ablation catheter can then be used to form a continuous lesion along the cardiac tissue as described in detail in the '394 publication incorporated by reference herein and presented herewith as Exhibit A.

FIGS. 4-7 illustrate an example delivery device 200 according to an embodiment. The delivery device 200 can be any suitable device configured to deliver a catheter, guidewire, needle, and/or any suitable medical device to a target tissue. In some instances, for example, a pair of delivery devices 200 can be used collectively to place a guidewire and/or a catheter (e.g., an ablation catheter or the like) within the pericardial space of a patient's heart, as described above with reference to the devices 100 and 100' in FIG. 3. By way of example, the delivery device 200 can be used to place a guidewire within the pericardial space and about the pulmonary veins of a heart, which in turn, can define a path along which an ablation catheter and/or any other suitable medical device can be advanced. For example, in some instances, an ablation catheter can be disposed about the pulmonary veins of a heart and can be used to produce a circumferential ablation lesion suitable to treat, for example, atrial fibrillation or the like. In some embodiments, portions of the delivery device 200 can be similar in form and/or function to those described above with reference to the delivery device 100. In some embodiments, the delivery device 200 can be substantially similar in form and/or function to those described in the '394 publication incorporated by reference herein and presented herewith as Exhibit A. As such, some portions of the delivery device 200 are not described in further detail herein.

The delivery device 200 (also referred to herein as "device") includes a handle 210, a first catheter 220, a second catheter 230, a conduit 240, a magnetic member 235, a first actuator 250 and a second actuator 260. The handle 210 can be any suitable shape, size, and/or configuration. In some embodiments, for example, the handle 210 can have a size and/or shape suitable for single-handed operation (either left hand or right hand operation). In some embodiments, the size and/or shape of the handle 210 can be configured to increase the ergonomics and/or ease of use of the device 200 (see e.g., FIGS. 4 and 5). In some embodiments, the handle 210 can be a two-part assembly, in which a first part is coupled to a second part to collectively form the handle 210. In such embodiments, the first part and the second part can be coupled during a manufacturing process or can be coupled, for example, by an end user (e.g., packaged and shipped in an unassembled configuration). As shown in FIGS. 6 and 7, the handle 210 defines an inner volume 213 configured to receive and/or house at least a portion of the first catheter 220, the second catheter 230, and the actuator assembly 250, as described in further detail herein.

The first catheter 220 can be any suitable catheter configured to be inserted into a portion of a patient. For example, the first catheter 220 can be formed of a relatively flexible material (e.g., formed of a material having a relatively low stiffness) such as any of those described herein. For example, in some embodiments, the first catheter 220 can be formed of a material having a bending stiffness between approximately $3 \times 10^{-5}$ Newton-meters$^2$ (N-m$^2$) and approximately $10^{-3}$ N-m$^2$, including all values and subranged in between. In this manner, at least a portion of the first catheter 220 can bend, flex, deflect, and/or otherwise elastically deform as the first catheter 220 is advanced within a portion of the body. Moreover, the first catheter 220 can have a size (e.g., diameter) that is associated with and/or otherwise suitable for insertion into the handle 210. In some embodiments, the diameter of the first catheter 220 can be in a range between approximately 6 French (e.g., about 2.0 mm) and approximately 15 French (e.g., about 5.0 mm), including all values and sub-ranges in between.

The first catheter 220 has a proximal end portion 221 and a distal end portion 222 and defines a lumen therethrough (not shown in FIGS. 4-7). The proximal end portion 221 of the first catheter 220 is fixedly disposed within the handle 210. The proximal end portion 221 of the first catheter 221 includes a protrusion 224 that is movably disposed within the second actuator 260. Said another way, the protrusion 224 is disposed within a portion of the second actuator 260 and is maintained in a relatively fixed position as the second actuator 260 is moved relative to the handle 210, as described in further detail herein.

The distal end portion 222 of the first catheter 220 is disposed distal to and outside of the handle 210. Although not shown in FIGS. 4-7, in some embodiments, the distal end portion 222 of the first catheter 220 and/or a portion of the first catheter 220 disposed distal to and outside of the handle 210 can be at least temporarily disposed within a lumen defined by a delivery catheter, as described above with reference to the delivery catheter 102 in FIGS. 1-3. For example, in some embodiments, the distal end portion of the first catheter 220 can be disposed within the lumen of the delivery catheter when the device 200 is in a first configuration (e.g., FIG. 6) and can be partially disposed within the lumen of the delivery catheter 202 and extend distal thereto when the device 200 is in a second configuration (e.g., FIG. 7). In other embodiments, no portion of the first catheter 220 is disposed in a delivery catheter or the like. As described in further detail herein, the distal end portion of the first catheter 220 is operably coupled to the first actuator 250 such that actuation of the first actuator 250 results in a deflection of the distal end portion of the first catheter 220.

The second catheter 230 can be any suitable catheter configured to be inserted into a portion of the patient and can have a size (e.g., diameter) that is associated with and/or otherwise suitable for insertion into the lumen of the first catheter 220. In addition, the second catheter 230 can be formed of a flexible material such as any of those described above. In some embodiments, for example, the second catheter 230 can have a stiffness that is less than a stiffness of the first catheter 220. For example, in some embodiments, the second catheter 230 can have a flexural modulus of about $3 \times 10^{-5}$ N-m² or less. In some embodiments, at least a portion of the second catheter 230 can be formed of and/or can include a nickel-titanium alloy (nitinol). As such, the second catheter 230 can be configured to bend and/or deflect a relatively large amount prior to permanent deformation and/or otherwise prior to failure (e.g., buckling, kinking, breaking, etc.). Moreover, the first catheter 220 can be configured to provide structural support to the second catheter 230 as the catheters 220 and 230 are advanced through a portion of the body (e.g., pericardial space).

The second catheter 230 has a proximal end portion (not shown in FIGS. 4-7) and a distal end portion 232 and defines a lumen therethrough (not shown in FIGS. 4-7). The distal end portion 232 of the second catheter 230 is coupled to the magnetic member 235 such that a lumen of the magnetic member 235 is in fluid communication with the lumen of the second catheter 230, as described in further detail herein. The proximal end portion of the second catheter 230 is coupled to the second actuator 260 such that the lumen of the second catheter 230 is in fluid communication with an access port 266 of the second actuator 260. As described in further detail herein, the second catheter 230 is configured to be moved within the lumen of the first catheter 220 between a first position (e.g., FIG. 6) and a second position (e.g., FIG. 7) in response to an actuation of the second actuator 260.

The magnetic member 235 is included in and/or coupled to the distal end portion of the second catheter 230. For example, in some embodiments, the magnetic member 235 is coupled to the second catheter 230 via a weld, adhesive, and/or mechanical fastener. In other embodiments, the magnetic member 235 can be integrally formed with the distal end portion of the second catheter 230 (e.g., co-molded, over-molded, etc.). In still other embodiments, the distal end portion of the second catheter 230 can be at least partially formed of a magnetic constituent material or the like. Moreover, the arrangement of the second catheter 230 and the magnetic member 235 is such that the lumen 233 of the second catheter 230 is in fluid communication with the lumen 237 of the magnetic member 235 (e.g., aligned and/or co-axial).

The magnetic member 235 can be any suitable shape, size, and/or configuration. In some embodiments, the magnetic member 235 can be, for example, an electromagnet, a paramagnet, a permanent magnet, and/or any other suitable magnetic member. As described above with reference to the magnetic member 135, the magnetic member 235 can be formed of any suitable magnetic material and/or a material visible under known imaging techniques such as fluoroscopy or the like (e.g., a radiopaque material). In some embodiments, the magnetic member 235 can be at least partially cylindrical or the like and can have a diameter that is substantially similar to a diameter of the first catheter 220 (see e.g., FIGS. 4-7). In some embodiments, the magnetic member 235 can include a distal end portion that is convex or frustoconical. In some embodiments, the magnetic member 235 can have a size and/or shape configured to be matingly coupled to a corresponding magnetic member of a second (e.g., separate) delivery device. In some embodiments, the size and/or shape of the magnetic member 235 can increase and/or otherwise direct a magnetic flux or force operable to increase a likelihood of a magnetic coupling between the magnetic member 235 and a corresponding magnetic member through a target tissue (e.g., magnetically coupled such that a portion of the target tissue is disposed therebetween), as described in further detail herein.

The conduit 240 can be any suitable shape, size, and/or configuration. As shown in FIGS. 6 and 7, the conduit 240 has a proximal end portion 241 and a distal end portion 242 and defines a lumen therethrough (not shown). The conduit 240 is at least partially disposed in the handle 210. The proximal end portion 241 of the conduit 240 is disposed outside of the proximal end portion 211 of the handle 210 and is coupled to a port 244 or the like. The port 244 can be, for example, a Luer Lok® or other coupling device configured to physically and fluidically couple the conduit 240 to a fluid reservoir and/or a fluid source. The distal end portion 242 of the conduit 240 is disposed within the inner volume 213 of the handle 210 and includes and/or is coupled to an adapter 245. As shown in FIGS. 6 and 7, the adapter 245 also receives and/or is coupled to the proximal end portion 221 of the first catheter 220. Although not shown, the arrangement of the catheters 220, 230, the conduit 240, and the adapter 245 is such that the lumen defined by the conduit 240 is in fluid communication with the lumen of the first catheter 220 and fluidically isolated from the lumen of the second catheter 230. That is to say, the lumen of the conduit 240 is in fluid communication with a portion of the lumen of the first catheter 220 defined between an inner surface of the first catheter 220 and an outer surface of the second catheter 230 disposed therein. In other embodiments, the lumen of the conduit 240 can be in fluid communication with the lumen of the first catheter 220 and the lumen of the second catheter 230. In this manner, the port 244 can be coupled to a fluid source or the like to provide, for example, irrigation through the lumen of the first catheter 220 and/or the lumen of the second catheter 230 or can be coupled to a fluid reservoir or vacuum source to provide, for example, suction through the lumen of the first catheter 220 and/or the lumen of the second catheter 230.

The first actuator 250 can be any suitable shape, size, and/or configuration. The first actuator 250 is movably coupled to the proximal end portion of the handle 210 and operably coupled to the distal end portion of the first catheter 220. For example, in the embodiment shown in FIGS. 4-7, a portion of the first actuator 250 is configured to rotate relative to the handle 210 and about the second actuator 260 (e.g., the second actuator 260 defines an axis of rotation) to deflect, bend, turn, steer, etc. the distal end portion of the first catheter 222. Specifically, as shown in FIGS. 5 and 6, the first actuator 250 includes a rotation member 251 and a translation member 252. The rotation member 251 is rotatably coupled to the proximal end portion 211 of the handle 210. Although not shown in FIGS. 4-7, the rotation member 251 includes an inner surface that can be threaded or the like and configured to selectively engage the translation member 252. The translation member 252 is movably disposed within the handle 210 and is configured for translational motion (e.g., linear motion in the proximal direction and/or the distal direction). In other words, rotation of the translation member 252 member within the handle 210 is limited and/or substantially restricted while an amount of translation of the translation member 252 is permitted (e.g., a predetermined range of motion). As shown in FIGS. 6 and 7, the translation member 252 has an outer surface that is threaded or the like. In this manner, the threaded outer surface of the translation member 252 can form a threaded coupling with the threaded inner surface of the rotation member 251. With rotation of the translation member 252 limited and/or substantially restricted, the arrangement of the first actuator 250 is such that rotation of the rotation member 251 results in a translation of the translation member 252 in a proximal direction or a distal direction along a first longitudinal axis (e.g., depending on a direction of rotation of the rotation member 251).

Although not shown in FIGS. 4-7, the translation member 252 can be operably coupled to the distal end portion of the first catheter 220 in any suitable manner. For example, in some embodiments, the translation member 252 is operably coupled to the distal end portion of the first catheter 220 via a wire, tether, and/or any other suitable linkage. In this manner, a user can manipulate and/or actuate the first actuator 250 to deflect, bend, turn, steer, etc. the distal end portion of the first catheter 220. For example, a user can rotate the rotation member 251 relative to the handle 210, which in turn, results in a translation of the translation member 252 in the proximal direction or the distal direction (as described above). Thus, with translation member 252 coupled to the distal end portion of the first catheter 220, the tether or the like can increase or decrease a force exerted on the distal end portion of the first catheter 220 in response to the movement of the translation member 252. Therefore, the change in force exerted by the tether or the like results in a deflection (e.g., bending, curving, twisting, and/or any other suitable reconfiguration) of the distal end portion of the first catheter 220, as described above with reference to the first actuator 150 and the first catheter 120 in FIGS. 1-3. In some instances, deflection of the distal end portion of the first catheter 220, for example, can facilitate the placement of the magnetic member 235 within a desired portion of the body, as described in further detail herein.

The second actuator 260 includes a proximal end portion 262 and a distal end portion 263. The second actuator 260 is slidably and/or movably coupled to the handle 210. For example, the second actuator 260 is configured to movably extend through the proximal end portion 211 of the handle 210 such that the proximal end portion 262 of the second actuator 260 is disposed outside of the handle 210 while the distal end portion 263 of the second actuator 260 is disposed within the inner volume 213 defined by the handle 210. The second actuator 260 defines a channel 264 configured to movably receive the proximal end portion 221 and the protrusion 224 of the first catheter 220. In this manner, an actuation force can be exerted on, for example, the proximal end portion 262 of the first actuator to slide the second actuator 260 in a distal direction (or a proximal direction) relative to the handle 210 and the first catheter 220, as indicated by the arrow AA in FIG. 7.

As described above, the second actuator 260 is at least operably coupled to the proximal end portion of the second catheter 230 such that the access port 266 of the first actuator 260 is in fluid communication with the lumen 233 of the second catheter 230. The second catheter 260 can be coupled to a proximal end of the second catheter. More specifically, the second actuator 260 includes a push rod 267 formed of a relatively rigid or stiff material that is fixedly coupled to the access port 266. A distal end of the push rod 267 is disposed within the lumen of the first catheter 220 and is coupled to and/or in contact with a proximal end of the second catheter 230. In this manner, the push rod 267 operably couples the second catheter 230 to the second actuator 260 such that movement of the second actuator 260 relative to the handle 210 and first catheter 220 results in a similar movement of the second catheter 230 and the magnetic member 235 relative to the handle 210 and first catheter 220, as indicated by the arrow BB in FIG. 7. In other words, a user can exert a force on the second actuator 260 to move the second actuator 260, the second catheter 230, and the magnetic member 235 in, for example, a distal direction to transition the device 200 from a first configuration (FIG. 6) to a second configuration (FIG. 7). Moreover, because the push rod 267 is relatively rigid, the force exerted on the second actuator 260 does not result in a bending, flexing, and/or deforming thereof, which might otherwise occur in the second catheter 230 if the second catheter 230 were coupled directly to the access port 266.

Although not shown in FIGS. 4-7, the push rod 267 defines a lumen that is in fluid communication with the lumen of the access port 266 and the lumen of the second catheter 230. Thus, the push rod 267 establishes fluid communication between the access port 266 and the second catheter 230. In some embodiments, the lumens of the access port 266, the push rod 267, and the second catheter 230 are aligned and/or otherwise co-axial. In this manner, any suitable member, device, substance, and/or the like can be delivered to and/or withdrawn from the lumen 233 of the second catheter 230. For example, in some instances, a needle and/or a guidewire can be inserted into the access port 266 of the first actuator 260 and advanced through the lumen 233 of the second catheter 230 and/or the lumen 237 of the magnetic member 235. More specifically, in some instances, a needle can be inserted into the access port 266 and through the lumens 233 and 237 to pierce, puncture, and/or otherwise define an opening in, for example, a pericardial reflection. Similarly, once the pericardial reflection is pierced, a guidewire can be inserted into the access port 266 and advanced through the lumens 233 and 237 and the opening in the pericardial reflection. The second port, second lumen, and third lumen can be collectively configured to receive and advance a guidewire during use. As such, a catheter and/or the like can be advanced along the guidewire and through the opening in the pericardial reflection, as described in further detail herein.

As described above, the device 200 can be used to deliver a catheter, guidewire, and/or the like to any suitable target location within, for example, a body. By way of a specific example, in some instances, the device 200 can be used to deliver an ablation catheter to a desired position within the pericardial space of a heart. In such instances, the device 200 can be used with a similar device and/or a device that is substantially the same as the device 200 (e.g., as described above with reference to devices 100 and 100' shown in FIG. 3) to deliver a guidewire within the pericardial space. In some instances, the guidewire placed within the pericardial space (e.g., and about the pulmonary veins) can provide a path along which a catheter (e.g., an ablation catheter) can be advanced, as described in detail above with reference to the devices 100 and/or 100' in FIGS. 1-3 as well as the '394 publication incorporated by reference herein and presented herewith as Exhibit A. Therefore, the operation of the device 200 is not described in further detail herein.

Figure 8:
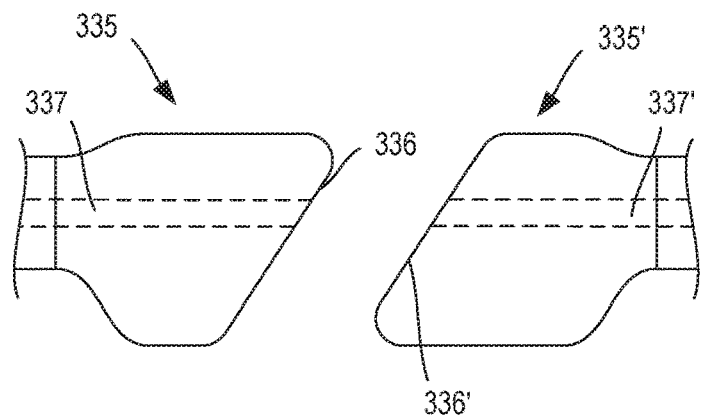
FIG. 8 is a schematic illustration of a first magnetic member and a second magnetic member configured to form a magnetic coupling therebetween according to an embodiment.
Figure 9:
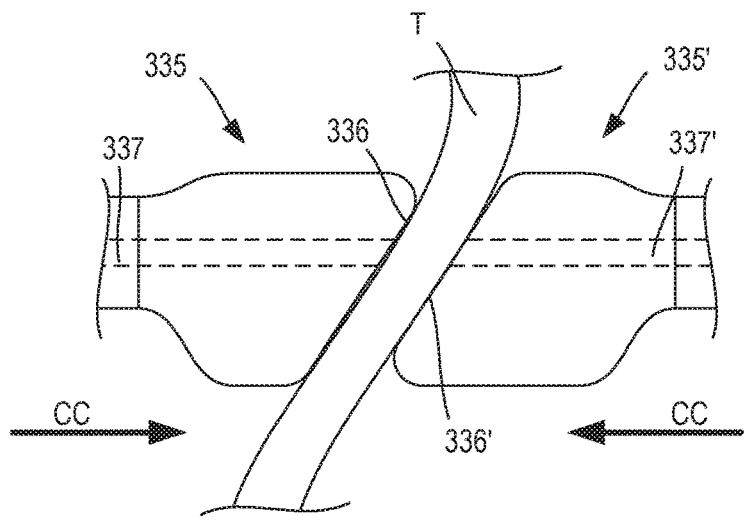
FIG. 9 is a schematic illustration of a first magnetic member and a second magnetic member configured to form a magnetic coupling therebetween according to an embodiment.
Figure 10:
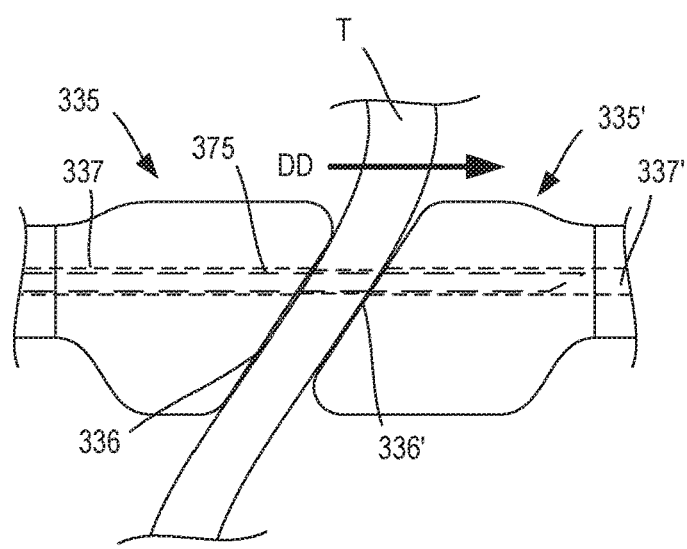
FIG. 10 is a schematic illustration of a first magnetic member and a second magnetic member configured to form a magnetic coupling therebetween according to an embodiment.

As described above, the devices 100 and 200 include the magnetic members 135 and 235, respectively, configured to form a magnetic coupling with a corresponding magnetic member of a second device (e.g., a device similar to or substantially the same as the devices 100 and/or 200, respectively). While the magnetic members 135 and 235 are particularly described above, in other embodiments, a delivery device can include any suitable magnetic member. For example, FIGS. 8-10 is a schematic illustration of a first magnetic member 335 and a second magnetic member 335' according to an embodiment. The magnetic members 335 and 335' can be included in any suitable device such as those described herein. More specifically, the first magnetic member 335 can be included in a first delivery device such as, for example, the delivery devices 100 and/or 200. As described above, the delivery devices 100 and/or 200 are configured to be used in conjunction with, for example, a corresponding delivery device (e.g., the device 100' shown in FIG. 3). As such, the second magnetic member 335' can be included in a second delivery device configured to be used in conjunction with the first delivery device.

The magnetic members 335 and 335' can be any suitable shape, size, and/or configuration and can be formed from any suitable material. For example, in some embodiments, the magnetic members 335 and 335' can be, for example, electromagnets, paramagnets, permanent magnets, and/or any other suitable magnetic member, or a combination thereof. The magnetic members 335 and 335' can be formed of any suitable magnetic material and/or any material capable of being magnetized. Moreover, the magnetic members 335 and 335' can be formed of a material configured to be visible within a portion of the body via fluoroscopic imaging techniques (e.g., a radiopaque material or the like). In some embodiments, the magnetic members 335 and 335' can be the same type of magnet and/or formed from the same material. In other embodiments, the first magnetic member 335 can be a first type of magnet and/or formed of a first material and the second magnetic member 335' can be a second type of magnet and/or formed of a second material different from the first type and/or first material, respectively. Furthermore, the first magnetic member 335 can have a first polarity and the second magnetic member 335' can have a second polarity opposite the first polarity.

In the embodiment shown in FIG. 8, the first magnetic member 335 includes a distal surface 336 and defines a lumen 337 extending through the first magnetic member 335. As described above with reference to the magnetic members 135 and 135' shown in FIG. 3, the first magnetic member 335 can be coupled to a catheter (e.g., the second catheters 130 and/or 230) such that the lumen 337 of the first magnetic member 335 is in fluid communication with a lumen of the catheter coupled thereto. In some embodiments, the third lumen 337 of the first magnetic member 335 can be off-centered and/or non-coaxial with a centerline and/or longitudinal axis of the first magnetic member 335 (e.g., parallel to but offset from the centerline and/or longitudinal axis), as shown in FIGS. 8-10. In other embodiments, the lumen 337 of the first magnetic member 335 can be centered and/or can be coaxial with the centerline of the first magnetic member 335. The distal surface 336 of the first magnetic member 335 can be any suitable shape, size, or configuration. For example, in the embodiment shown in FIGS. 8-10, the distal surface 336 is a substantially planar surface forming a slope and/or angled surface (e.g., a surface that is not orthogonal to a horizontal or a vertical plane). The slope of the distal surface 335 can be and/or can form any suitable angle relative to, for example, a horizontal or vertical plane (e.g., 5°, 10°, 15°, 20°, 30°, 45°, 60°, or more). In some embodiments, the angle and/or slope of the distal surface 336 can, for example, increase an area of the distal surface 336, which in turn, can facilitate a magnetic coupling between the first magnetic member 335 and the second magnetic member 335', as described in further detail herein.

The second magnetic member 335' includes a distal surface 336' and defines a lumen 337' extending through the second magnetic member 335'. The second magnetic member 335' can be coupled to a catheter such that the lumen 337' of the second magnetic member 335' is in fluid communication with the lumen of the catheter coupled thereto. As described above with reference to the first magnetic member 335, the lumen 337' of the second magnetic member 335' is off-center and/or non-coaxial with a centerline of the second magnetic member 335'. Moreover, the distal surface 336' of the second magnetic member 335' can be substantially planar with a slope and/or angle that is associated with and/or corresponds to the slope and/or angle of the first magnetic member 335. In other words, the distal surfaces 336 and 336' can be complimentary or the like (e.g., the angles of the distal surfaces 336 and 336' can be supplementary angles).

In some embodiments, the arrangement of the distal surface 336 of the first magnetic member 335 and the distal surface 336' of the second magnetic member 335' can facilitate a magnetic coupling therebetween when disposed within a portion of the body. By way of example, the first magnetic member 335 can be inserted into a portion of the body and positioned on a first side of a target tissue T (see e.g., FIGS. 9 and 10), while the second magnetic member 335' can be inserted into the portion of the body and positioned on a second side of the target tissue T. As a specific example, the first magnetic member 335 can be inserted into the pericardial space of a heart and positioned on a first side of a pericardial reflection and the second magnetic member 335' can be inserted into the pericardial space and positioned on a second side of the pericardial reflection opposite the first side. As such, an attractive magnetic force between the magnetic members 335 and 335' (e.g., due to opposite polarities) can pull the magnetic members 335 and 335' toward the target tissue T, as indicated by the arrows CC in FIG. 9. In this manner, the magnetic force can at least temporarily couple the magnetic members 335 and 335' with a portion of the target tissue T disposed therebetween. As described above, the arrangement of the distal surfaces 336 and 336' can facilitate the magnetic coupling therebetween and/or can facilitate the alignment of the lumens 337 and 337'. For example, in some embodiments, the angled and/or sloped distal surfaces 336 and 336' can increase an amount of magnetic flux and/or can otherwise direct an amount of magnetic flux operable to couple the magnetic members 335 and 335'.

As shown in FIG. 10, with the magnetic members 335 and 335' coupled, a guidewire, sharpened guidewire, or flexible needle can be advanced through, for example, the lumen 337 of the first magnetic member 335 (and a lumen of the catheter coupled thereto) to pierce and/or define an opening in the portion of the target tissue T (e.g., a pericardial reflection or the like) disposed between the distal surfaces 336 and 336', as indicated by the arrow DD in FIG. 10. Once the target tissue T is pierced, a standard guidewire can similarly be advanced through the opening in the target tissue T and the guidewire, in turn, can be configured to provide and/or define a path along which one or more catheters or other suitable medical device can be advanced such that at least a portion of the one or more catheters or other suitable medical device extends through the target tissue T, as described in detail above with reference to the device 100 shown in FIGS. 1-3.

Figure 11:
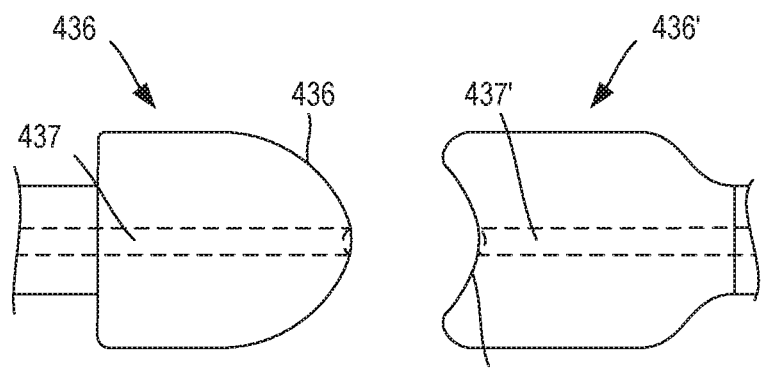
FIG. 11 is a schematic illustration of a first magnetic member and a second magnetic member configured to form a magnetic coupling therebetween according to an embodiment.

While the magnetic members 335 and 335' are described above as being substantially cylindrical with substantially linear distal surfaces 336 and 336', respectively, in other embodiments, a magnetic member can be any suitable shape. For example, FIG. 11 is a schematic illustration of a first magnetic member 435 and a second magnetic member 435' according to an embodiment. As described above with reference to the magnetic members 335 and 335', the first magnetic member 435 includes a distal surface 436 and can couple to a catheter such that a lumen 437 of the first magnetic member 435 is in fluid communication with a lumen of the catheter coupled thereto. In the embodiment shown in FIG. 11, the lumen 437 is substantially centered and/or coaxial with a centerline of the first magnetic member 435. The first magnetic member 435 can be any suitable shape, size, and/or configuration. For example, as shown in FIG. 11, the first magnetic member 435 is substantially cylindrical and the distal surface 436 is substantially convex. In other words, the distal surface 436 of the first magnetic member 435 can be at least partially frustoconical or the like.

The second magnetic member 435' includes a distal surface 436' and defines a lumen 437' extending through the second magnetic member 435'. The second magnetic member 435' can be coupled to a catheter such that the lumen 437' of the second magnetic member 435' is in fluid communication with the lumen of the catheter coupled thereto. As described above with reference to the first magnetic member 435, the lumen 437' of the second magnetic member 435' is centered and/or coaxial with a centerline of the second magnetic member 435'. In this embodiment, the second magnetic member 435' is substantially cylindrical and the distal surface 436' of the second magnetic member 435' is substantially concave. In some instances, the concave distal surface 436' of the second magnetic member 435' can have a radius of curvature that is substantially similar to a radius of curvature of the convex distal surface 436 of the first magnetic member 435. In other words, the distal surfaces 436 and 437' can be complimentary or the like (e.g., physically and magnetically). In some embodiments, the arrangement of the first magnetic member 435 and the second magnetic member 435' can facilitate a magnetic coupling therebetween and/or an alignment of a lumen 437 of the first magnetic member 435 and the lumen 437' of the second magnetic member 435', as described above with reference to the magnetic members 335 and 335'. Moreover, in some instances, the curved distal surfaces 436 and 436' (e.g., convex and concave, respectively) can limit and/or substantially prevent a relative movement of a tissue disposed therebetween.

Figure 12:
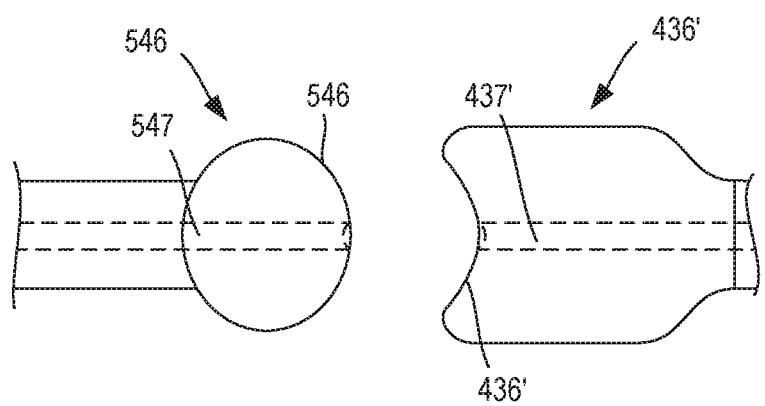
FIG. 12 is a schematic illustration of a first magnetic member and a second magnetic member configured to form a magnetic coupling therebetween according to an embodiment.

FIG. 12 is a schematic illustration of a first magnetic member 535 according to an embodiment that is configured to form a magnetic coupling with, for example, the second magnetic member 435' described above with reference to FIG. 11. In this embodiment, the first magnetic member 535 is substantially circular or spherical with a rounded or convex distal surface 536. In some embodiments, the distal surface 536 can have a radius of curvature that is substantially similar to the radius of curvature of the distal surface 336 of the magnetic member 335. In other embodiments, the first magnetic member 535 (e.g., the spherical magnetic member) or at least the distal surface 536 thereof, can have any suitable radius of curvature. As described above with reference to FIG. 11, the arrangement of the first magnetic member 535 and the second magnetic member 435' can facilitate a magnetic coupling therebetween and/or can facilitate an alignment of a lumen 537 of the first magnetic member 535 and the lumen 437' of the second magnetic member 435'.

Figure 13:
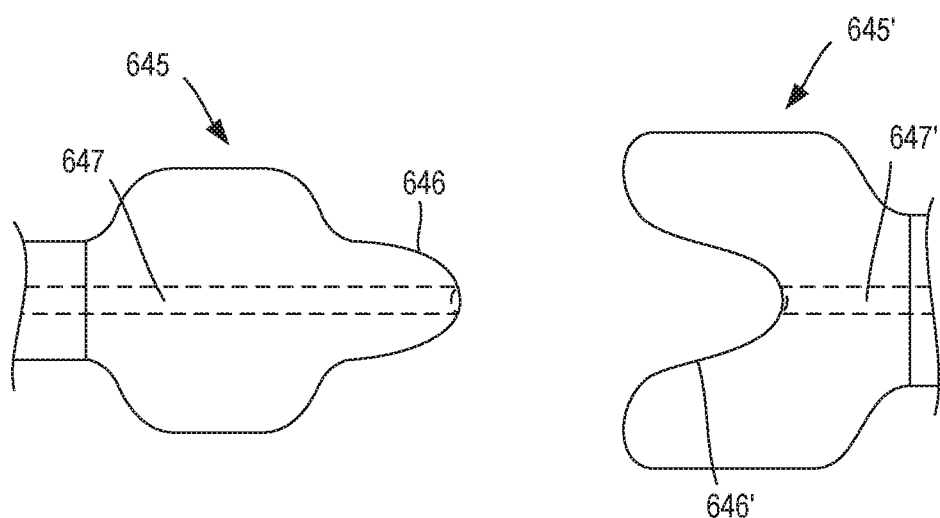
FIG. 13 is a schematic illustration of a first magnetic member and a second magnetic member configured to form a magnetic coupling therebetween according to an embodiment.

FIG. 13 is a schematic illustration of a first magnetic member 635 and a second magnetic member 635' according to another embodiment. The first magnetic member 635 and the second magnetic member 635' can be substantially similar in at least function to the magnetic members 335 and 335', respectively, described above with reference to FIG. 8. The first magnetic member 635 includes a distal surface 636 and defines a lumen 637 extending through the first magnetic member 635. Similarly, the second magnetic member 635' includes a distal surface 636' and defines a lumen 637' extending through the second magnetic member 635'. In the embodiment shown in FIG. 13, the distal surface 636 of the first magnetic member 635 is substantially elongated with a reduced diameter relative to, for example, the distal surface 336 of the first magnetic member 335 shown in FIG. 8. That is to say, the first magnetic member 635 tapers from a relatively larger first diameter to a relatively smaller second diameter formed, at least in part, by the distal surface 636. The distal surface 636' of the second magnetic member 635' is a substantially elongated concave surface with a size and shape that substantially corresponds with a size and shape of the distal surface 636 of the first magnetic member 635. Thus, as described above with reference to the magnetic member 535 and 535' shown in FIG. 8, the arrangement of the magnetic members 635 and 635' shown in FIG. 13 can facilitate a magnetic coupling therebetween and can facilitate an alignment of the lumens 637 and 637'.

Any of the delivery devices and/or portions thereof can be used during a procedure to deliver a catheter, guidewire, and/or the like to any suitable target location within, for example, a body. By way of a specific example, in some instances, the devices described herein (e.g., the devices 100 and/or 200) can be used to deliver an ablation catheter to a desired position within the pericardial space of a heart 10, as shown in FIGS. 14-23. In such instances, the device can be one of a pair of similar devices (e.g., corresponding devices) to deliver the ablation catheter. In the example shown in FIGS. 14-23, a first delivery device 700 is used in conjunction with a second delivery device 700', as described above with reference to the devices 100 and 100' shown in FIG. 3.

The first delivery device 700 (also referred to as "first device") includes at least a first catheter 720, a second catheter 730, a magnetic member 735, and a delivery catheter 702. Similarly, the second delivery device 700' (also referred to as "second device") includes at least a fourth catheter 720', a fifth catheter 730', a second magnetic member 735', and a delivery catheter 702' (e.g., sixth catheter). Although not shown in FIGS. 14-23, the devices 700 and/or 700' can also include a handle, and two actuators configured to move the first catheter 720 and fourth catheter 720', respectively, and/or the second catheter 730 and fifth catheter 730', respectively. In this manner, the first device 700 and the second device 700' can be substantially similar in form and/or function to the device 100 described above with reference to FIGS. 1-3 and/or the device 200 described above with reference to FIGS. 4-7. In addition, each of the devices 700 and 700' can include one or more ports in fluid communication with a lumen of the first catheter 720 and fourth catheter 720', respectively, a lumen of the second catheter 730 and fifth catheter 730', respectively, and/or a lumen of the third catheter 702 and sixth catheter 702', respectively. The ports, in turn, can be coupled to a fluid source, fluid reservoir, pump, and/or the like to provide lavage or suction as desired. For example, in some embodiments, the ports can be in fluid communication with the lumen of the first catheter 720 and fourth catheter 720' to provide lavage or suction through one or more openings, holes, apertures, ports, etc. disposed at or near a distal end portion of the first catheter 720 and fourth catheter 720' (see e.g., the distal end portion of the first catheter 720 in FIG. 17). In some embodiments, the ports can be used to inject a contrast agent through the lumen of the first catheter 720 and/or fourth catheter 720' and out of the openings, which in turn, can facilitate visualization of the anatomy and/or portion of the first device 700 and/or second device 700' during use.

In a procedure for treating, for example, atrial fibrillation of a heart of a patient, an operator or user (e.g., surgeon) can remove the first device 700 and/or the second device 700' from a sterile packaging (e.g., the devices 700 and 700' can be packaged and sold together as a kit or can be packaged and sold individually). Similarly, the operator can remove an introducer catheter 704 from a sterile packaging (e.g., the same packaging as the devices 700 and 700' or a separate package). The introducer catheter 704 can be any suitable catheter commonly used to advance devices and/or materials through a lumen thereof. Thus, the introducer catheter 704 is not described in further detail herein.

Figure 14:
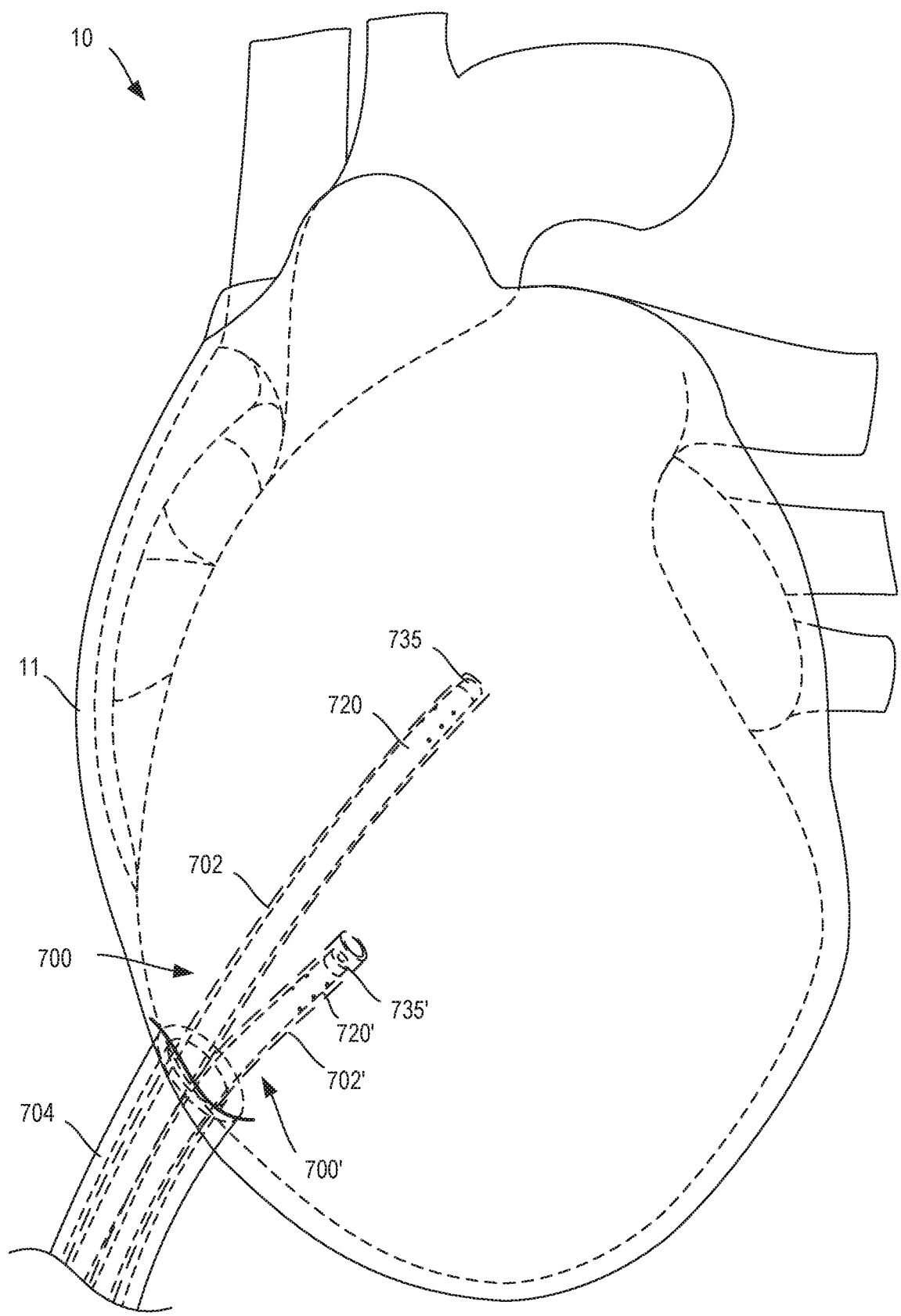
FIG. 14 is an illustration of a portion of a first delivery device and a portion of a second delivery device disposed within a pericardial space of a heart according to an embodiment.

The operator can insert the introducer catheter 704 into the body of the patient via, for example, subxiphoid access or the like. The introducer catheter 704 can be advanced to be partially inserted through an incision in the pericardium 11 of the heart 10 to place the lumen of the introducer catheter 704 in fluid communication with the pericardial space, as shown in FIG. 14. With the lumen of the introducer catheter 704 in fluid communication with the pericardial space, the operator can manipulate the first device 700 and the second device 700' to advance the delivery catheters 702 and 702', respectively, through the lumen of the introducer catheter 704 and into the pericardial space of the heart 10.

In some embodiments, the first catheter 720, the second catheter 730, and the magnetic member 735 of the first device 700 can each be disposed within the delivery catheter 702 of the first device 700 as the delivery catheter 702 is advanced. Similarly, the first catheter 720', the second catheter 730', and the magnetic member 735' of the second device 700' can each be disposed within the delivery catheter 702' of the second device 700' as the delivery catheter 702' is advanced. Although the delivery catheters 702 and 702' are shown as being advanced through the introducer catheter 704 to be inserted into the pericardial space of the heart 10, in other instances, the delivery catheters 702 and 702' can be delivered and inserted into the pericardium without using an introducer catheter such as the introducer catheter 704.

Figure 15:
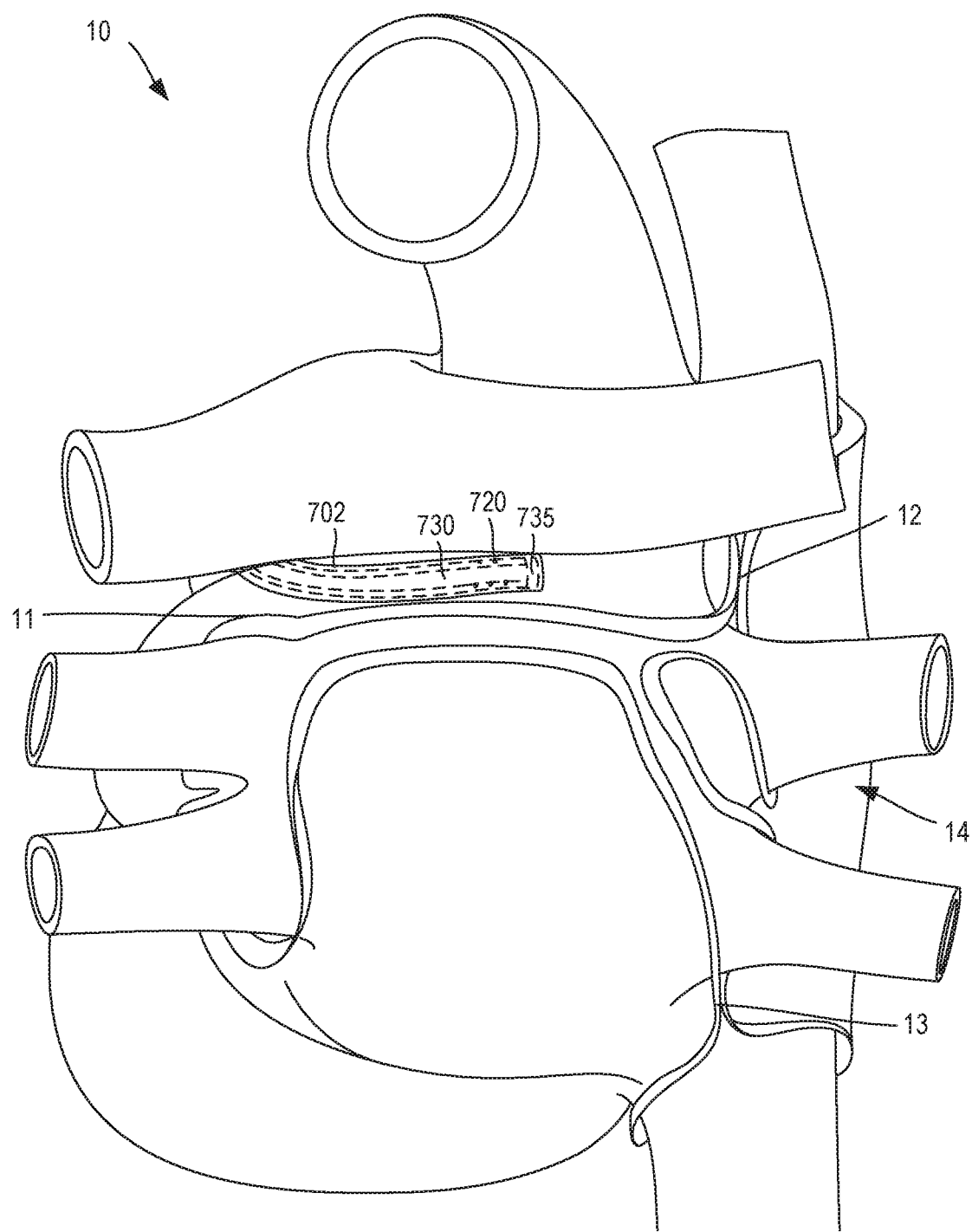
FIG. 15 is an illustration of a portion of a first delivery device disposed within a pericardial space of a heart according to an embodiment.
Figure 16:
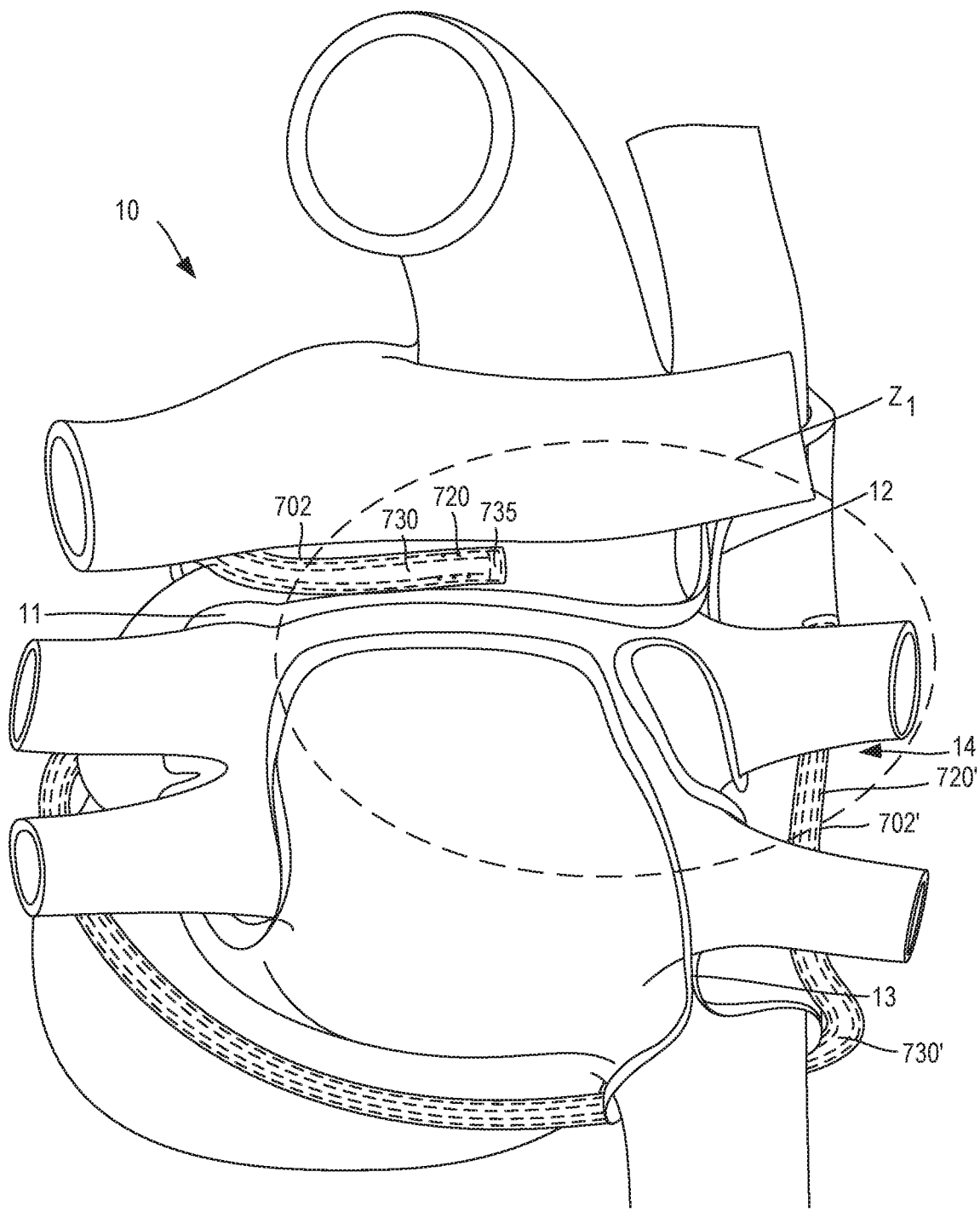
FIG. 16 is an illustration of a portion of a first delivery device disposed within the pericardial space of the heart and a portion of the second delivery device disposed within the pericardial space of the heart via a posterior approach.

As shown in FIGS. 15 and 16, the operator can advance the delivery catheter 702 (sometimes referred to as the "transverse sinus catheter") of the first device 700 in a first direction around and/or relative to, for example, the pulmonary veins 14 to dispose a distal end of the delivery catheter 702 of the first device 700 in a desired position within the pericardial space and on a first side of a superior pericardial reflection 12. For example, in some instances, the delivery catheter 702 can be passed through and/or along the transverse sinus of the heart. The operator can also advance the delivery catheter 702' (sometimes referred to as the "oblique sinus catheter") of the second device 700' in a second direction around the epicardial surface to dispose a distal end of the deliver catheter 702' of the second device 700' in a desired position within the pericardial space and on a second side of the superior pericardial reflection 12. For example, in some instances, the delivery catheter 702' can be passed through and/or along the oblique sinus of the heart. In some instances, the desired position of the delivery catheters 702 and 702' can be a position in which a distal surface of the delivery catheter 702 and 702' is within about five centimeters (cm) from the first or superior pericardial reflection 12 (also referred to henceforth as "superior pericardial reflection").

Figure 16A:
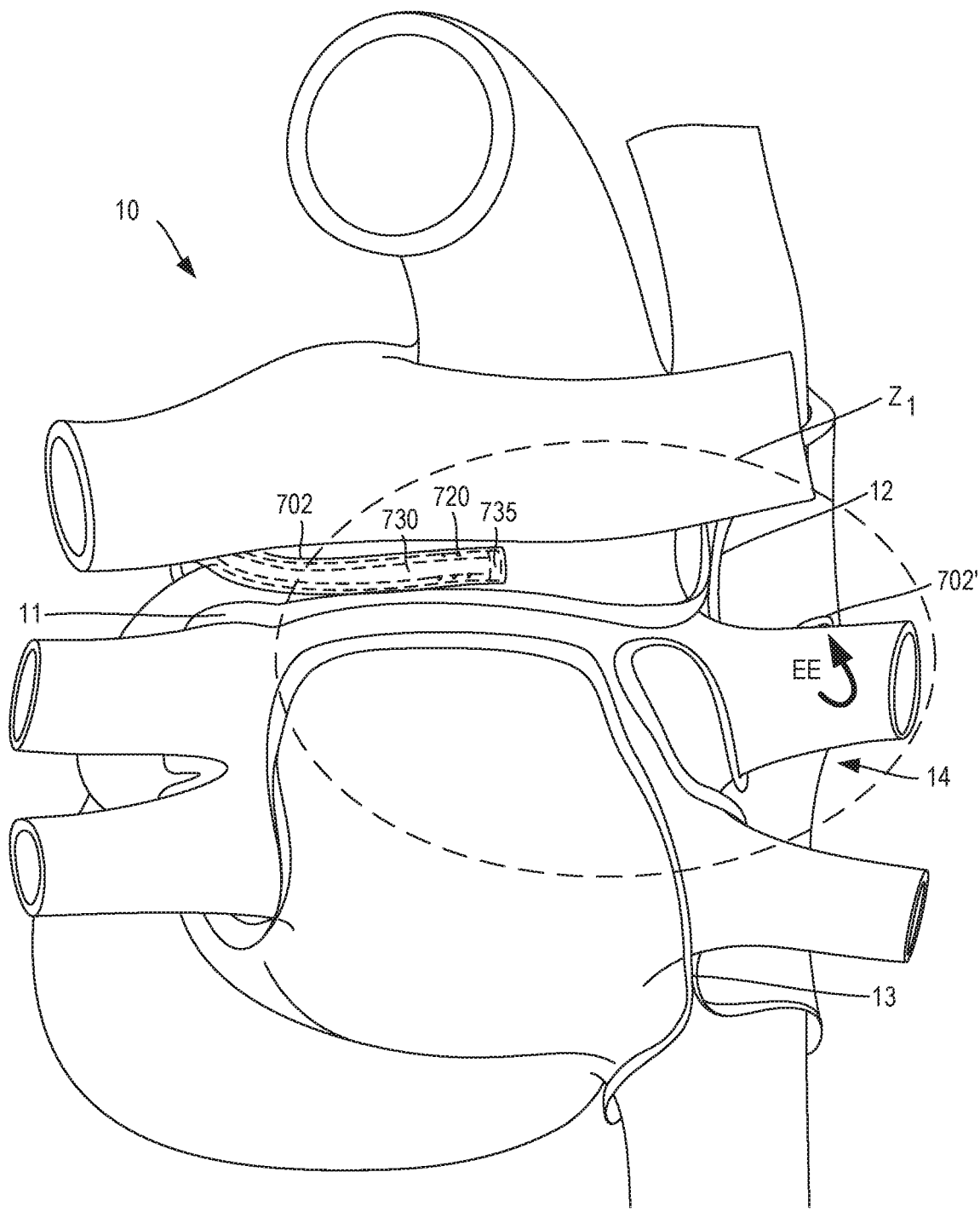
FIG. 16A is an illustration of a portion of a first delivery device disposed within a pericardial space of the heart and a portion of a second delivery device disposed within the pericardial space of the heart via an anterior approach.

Although the delivery catheter 702' of the second device 700' (e.g., the oblique sinus catheter) is shown in FIG. 16 as being passed around the posterior side of the heart 10 (e.g., inferior to the pulmonary veins 14) to the desired position on the second side of the superior pericardial reflection 12, in other instances, the delivery catheter 702' can be placed in the desired position via a different path along or relative to the heart 10. For example, in some instances, the delivery catheter 702' can remain substantially on the anterior side of the heart 10 and can be positioned on the second side of the superior pericardial reflection 12, as shown in FIG. 16A. In other words, while the delivery catheter 702' is shown in FIG. 16 as being passed around the left side of the heart 10 (in the posterior view shown in FIGS. 16, 16A), in some instances, the delivery catheter 702' can be passed around the right side of the heart 10 to be placed in the desired position relative to the superior pericardial reflection 12, as indicated by the arrow EE in FIG. 16A.

With the transverse sinus catheter 702 (i.e., the first delivery catheter 702 of the first device 700) and the oblique sinus catheter 702' (i.e., the second delivery catheter 702' of the second device 700') in the desired position, the operator can advance the first catheter 720, the second catheter 730, and the first magnetic member 735 of the first device 700 in a distal direction relative to the first delivery catheter 702 toward the superior pericardial reflection 12. For example, in some embodiments, the operator can actuate the second actuator of the first device 700 (e.g., the second actuators 160 and/or 260 described above) to advance the second catheter 730 and the first magnetic member 735 coupled thereto in a distal direction and relative to the first catheter 720 toward the superior pericardial reflection 12. In some instances, the operator can also manipulate the first actuator (e.g., the first actuators 150 and/or 250 described above) to move, bend, deflect, etc. a distal end portion of the first catheter 720, as described in detail above. In this manner, the second catheter 730 and the magnetic member 735 of the first device 700 can be advanced and/or steered within the pericardial space toward the superior pericardial reflection 12.

Figure 17:
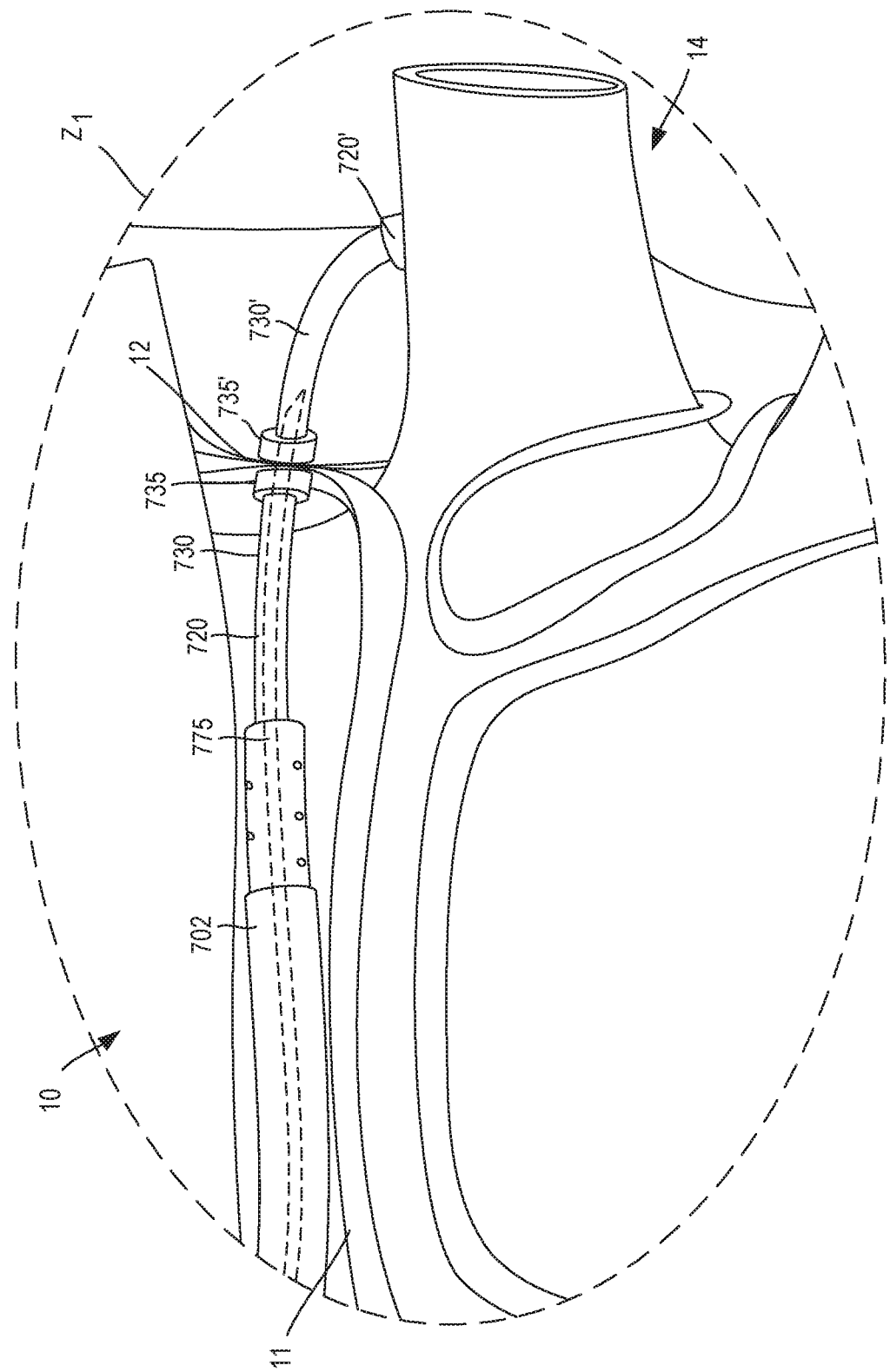
FIG. 17 is an enlarged illustration of a portion of the first delivery device and a portion of the second delivery device of FIGS. 14-16A within the heart, identified in FIGS. 16-16A as region $Z_1$.

With the oblique sinus catheter 702' in the desired position (e.g., via the posterior approach shown in FIG. 16 or the anterior approach shown in FIG. 16A), the operator can similarly manipulate the second device 700' to advance the fourth catheter 720', the fifth catheter 730', and the second magnetic member 735' of the second device 700' in a distal direction relative to the delivery catheter 702 toward the superior pericardial reflection 12. As shown in FIG. 17, advancing the second catheter 730 and fifth catheter 730' can place the magnetic members 735 and 735', respectively, in positions such that an attractive magnetic force between the magnetic members 735 and 735' results in a magnetic coupling of the first magnetic member 735 of the first device 700 to the second magnetic member 735' of the second device 700' with a portion of the superior pericardial reflection 12 disposed therebetween. As described above with reference to the magnetic members 135, 135', 235, 335 and 335', 435 and 435', 535 and 535', and 635 and 635', the arrangement, shape, size, and/or configuration of the magnetic members 735 and 735' can be configured to facilitate and/or enhance a coupling of the magnetic members 735 and 735' and/or an alignment of the magnetic members 735 and 735' once magnetically coupled.

After magnetically coupling the magnetic members 735 and 735' (e.g., through the superior pericardial reflection 12), the operator can advance, for example, a flexible needle 775 (or a crossing wire such as a sharpened guidewire) through the lumen of the second catheter 730 and a lumen of the magnetic member 735 of the first device 700 to pierce the portion of the superior pericardial reflection 12 disposed between the magnetically coupled magnetic members 735 and 735'. For example, as described above with reference to the devices 100 and/or 200, an actuator and/or any other suitable portion of the first device 700 can include a port that is in fluid communication with the lumen of the second catheter 730. Thus, the crossing wire 775 can be advanced through, for example, a handle of the first device 700, the second catheter 730, and the magnetic member 735 and through the superior pericardial reflection 12.

After puncturing the superior pericardial reflection 12, the operator can retract the crossing wire 775. In some instances, the operator can advance a dilation catheter or the like (not shown) through the lumens of the second catheter 730 and magnetic member 735 of the first device 700 and into the opening of the superior pericardial reflection 12. In this manner, the dilation catheter can be actuated and/or otherwise employed to dilate the opening defined in the superior pericardial reflection 12 to a sufficient size such that at least the first catheter 720, the second catheter 730, and the magnetic member 735 of the first device 700 can be extended out of the delivery catheter 702 and advanced through the opening. In some instances, the opening can be dilated to a size sufficient to allow an ablation catheter to be passed therethrough, as described in further detail herein.

Although described as dilating the opening defined by the pericardial reflection 12, in other instances, the opening need not be dilated prior to advancing the first catheter 720, the second catheter 730, and the magnetic member 735.

Figure 18:
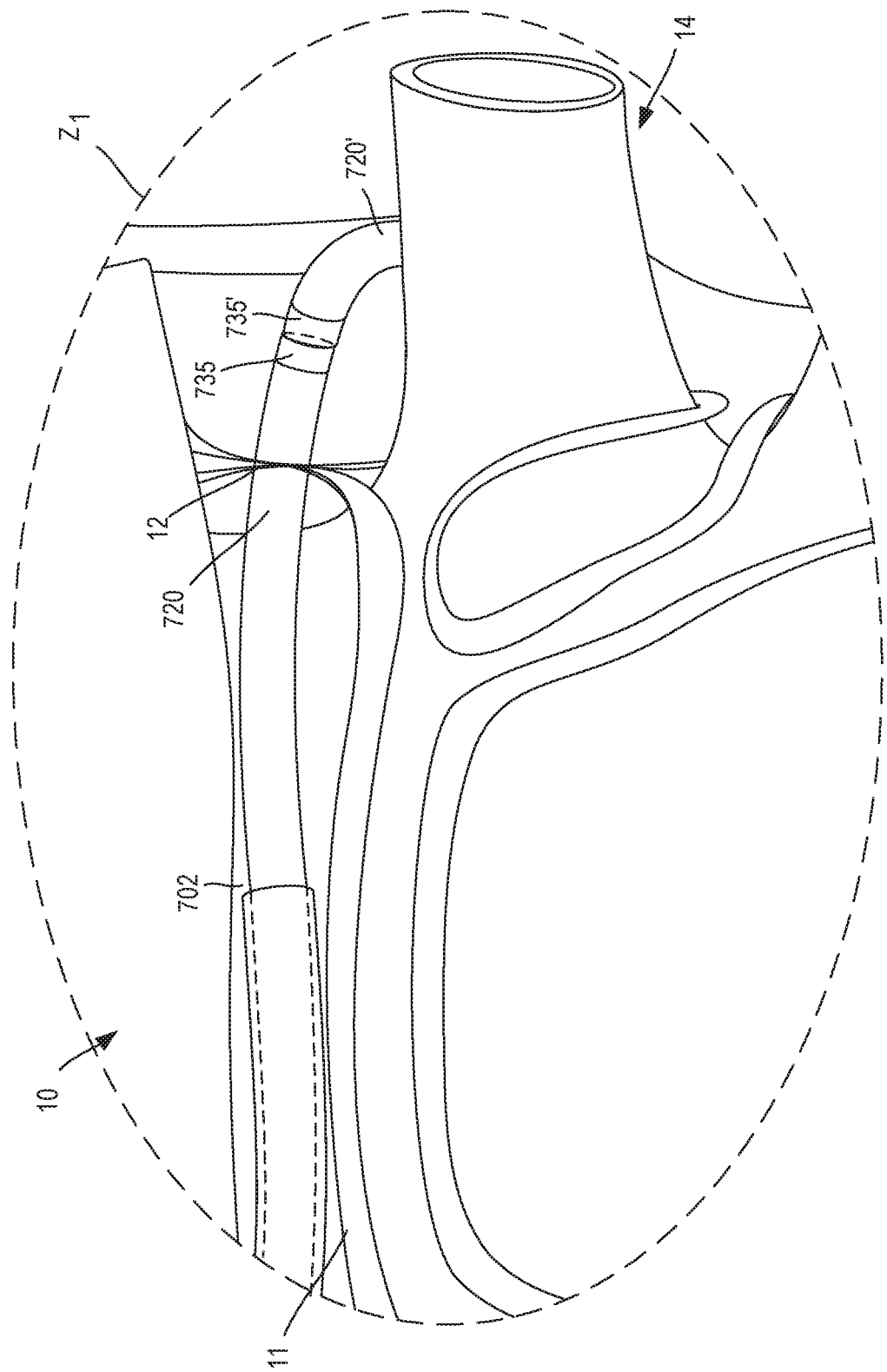
FIG. 18 is an enlarged illustration of a portion of the first delivery device and a portion of the second delivery device of FIGS. 14-16 within the heart, identified in FIGS. 16-16A as region $Z_1$.
Figure 19:
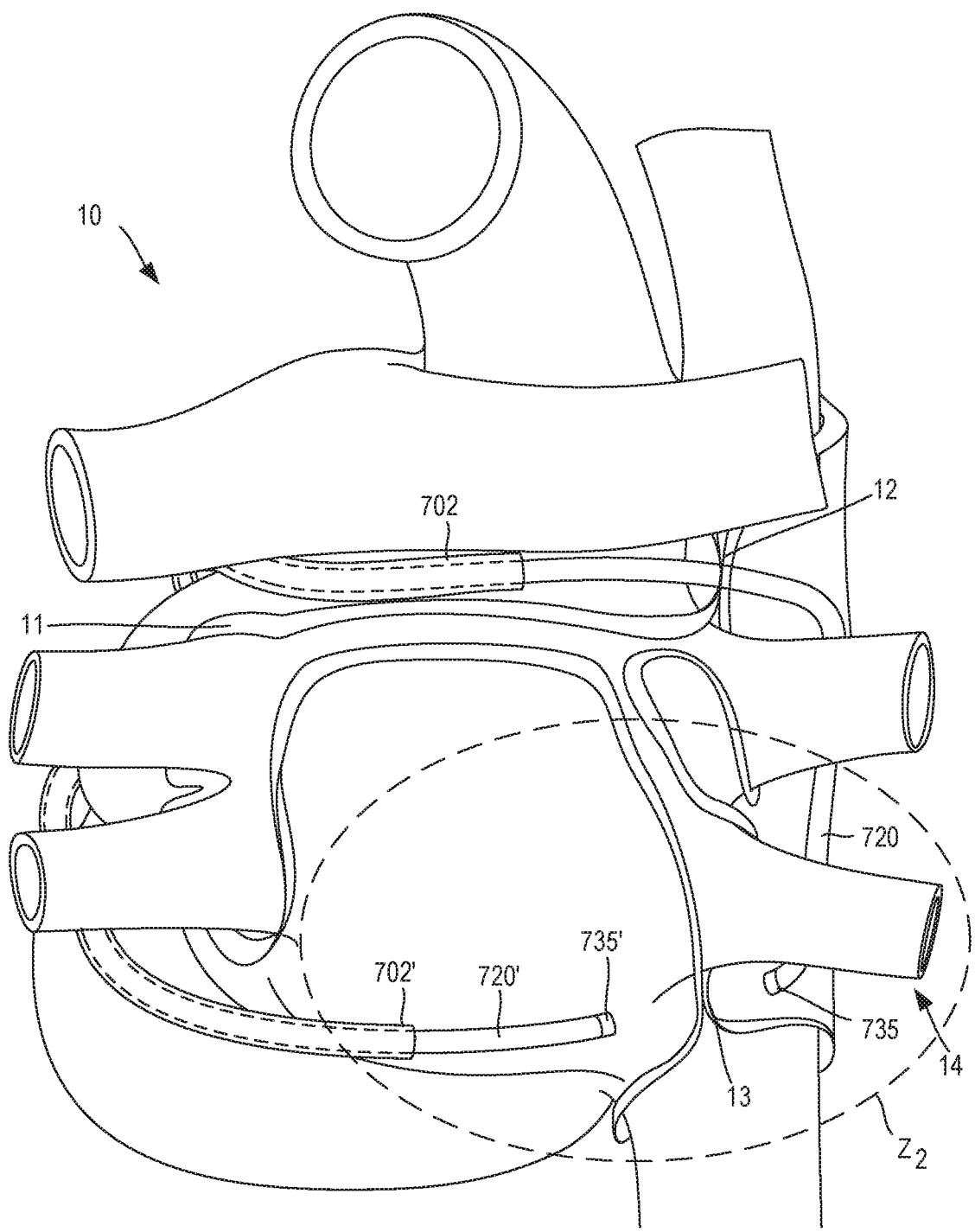
FIG. 19 is an illustration of a portion of a first delivery device and a portion of a second delivery device configured to place a guidewire and/or catheter within a pericardial space of a heart according to an embodiment.

As shown in FIGS. 18 and 19, the first catheter 720 and fourth catheter 720', the second catheter 730 and fifth catheter 730', and the magnetic members 735 and 735' can extend out of the delivery catheters 702 and 702', respectively, and can be moved and/or repositioned to be disposed in a desired position relative to a second or posterior pericardial reflection 13 (referred to henceforth as "inferior pericardial reflection 13"). More particularly, as shown in FIG. 19, the first catheter 720, the second catheter 730, and the first magnetic member 735 of the first device 700 can be advanced on a posterior side of the heart 10 around the right pulmonary veins 14 to be placed in a desired position relative to the inferior pericardial reflection 13. In some instances, the fourth catheter 720', the fifth catheter 730', and the second magnetic member 735' of the second device 700' can be retracted into the delivery catheter 702' (the oblique sinus catheter 702'). Once retracted, the oblique sinus catheter can be repositioned relative to the heart 10 and, for example, advanced around the left side of the heart 10 from an anterior position to a posterior position. In other words, the oblique sinus catheter 702' can be advanced around the heart 10 through, for example, the oblique sinus to the desired position relative to the inferior pericardial reflection 13, as shown in FIG. 19. In this manner, the oblique sinus catheter 702' is designed and usable for being positioned on the posterior side of the heart as described herein from both the right side of the heart (e.g., via the anterior approach shown in FIG. 16A) and the left side of the heart (e.g., via the posterior approach shown in FIG. 16).

Figure 20:
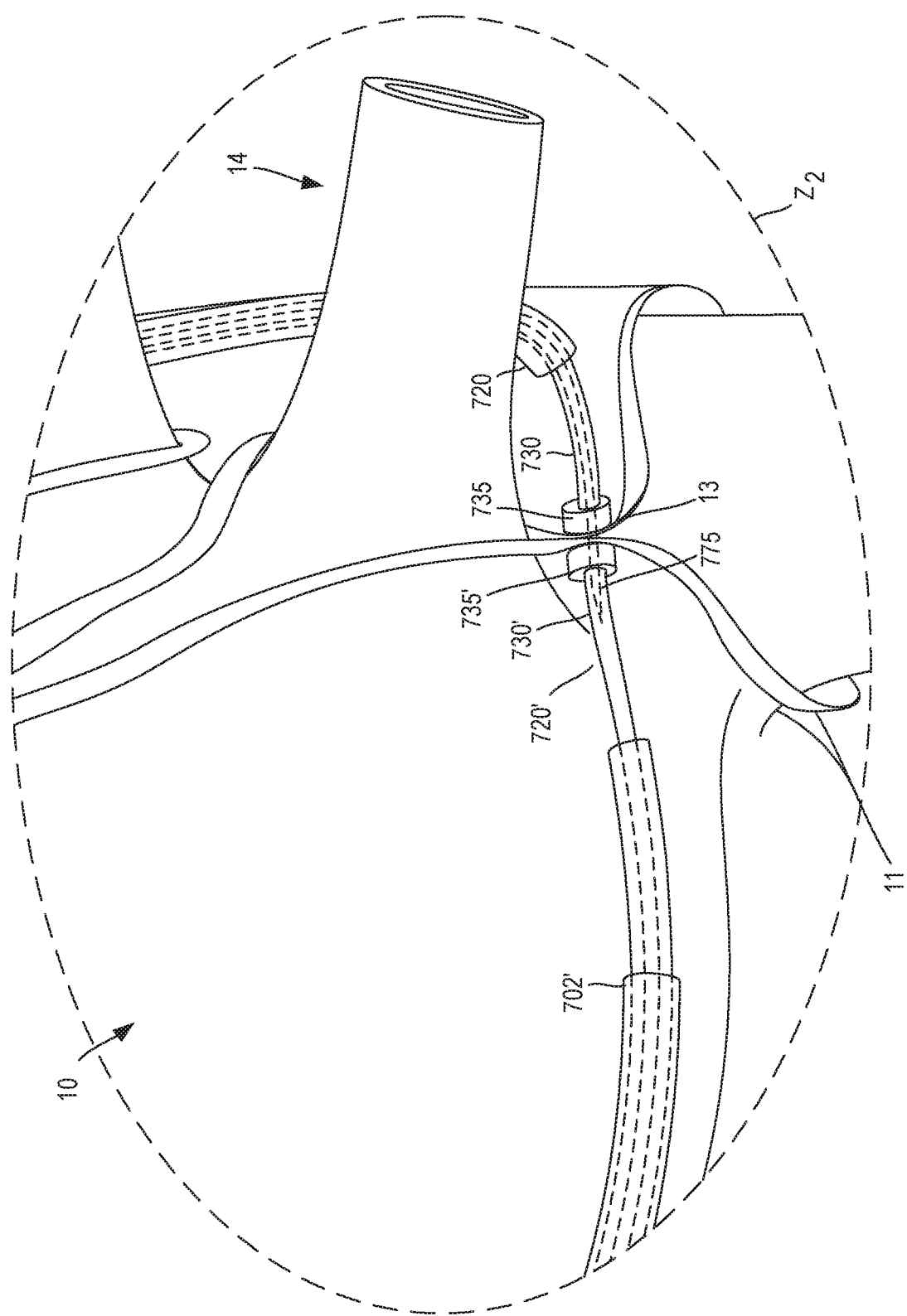
FIG. 20 is an enlarged illustration of a portion of the first delivery device and a portion of the second delivery device of FIGS. 14-16 within the heart, identified in FIG. 19 as region $Z_2$.
Figure 21:
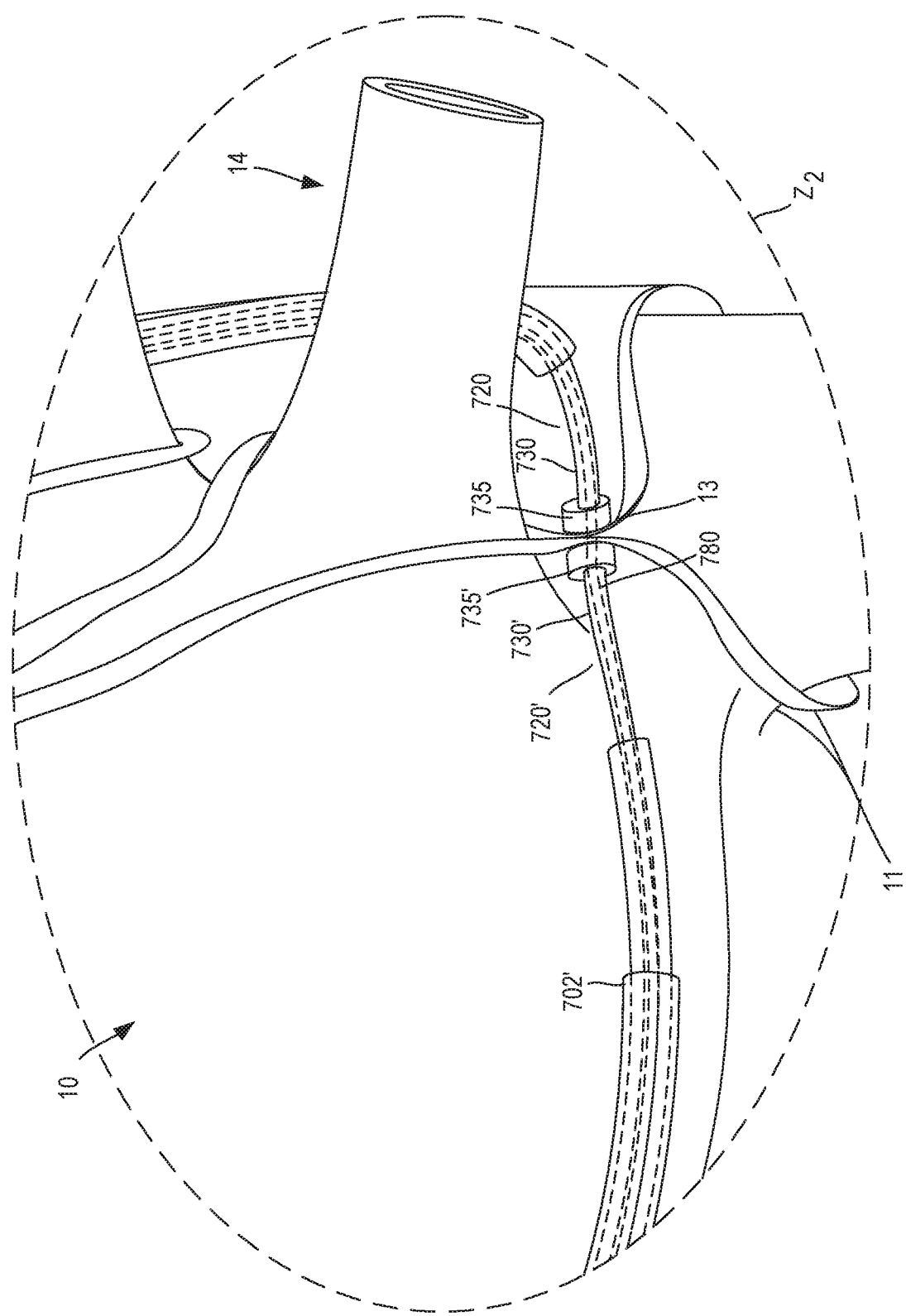
FIG. 21 is an enlarged illustration of a portion of the first delivery device and a portion of the second delivery device of FIGS. 14-16 within the heart, identified in FIG. 19 as region $Z_2$.

Once the first catheter 720 and fourth catheter 720' are disposed in the desired positions relative to the inferior pericardial reflection 13, the operator can manipulate the devices 700 and 700' to magnetically couple the magnetic members 735 and 735' with a portion of the inferior pericardial reflection 13 disposed therebetween (see e.g., FIG. 20), as described in detail above with reference to the superior pericardial reflection 12. Furthermore, the operator can manipulate the first device 700 to advance the crossing wire 775 to pierce and/or puncture the inferior pericardial reflection 13 (FIG. 20). After piercing and/or puncturing the inferior pericardial reflection 13, the operator can retract the crossing wire 775 and can subsequently advance the guidewire 780 through the opening defined by the inferior pericardial reflection 13, as shown in FIG. 21.

Figure 22:
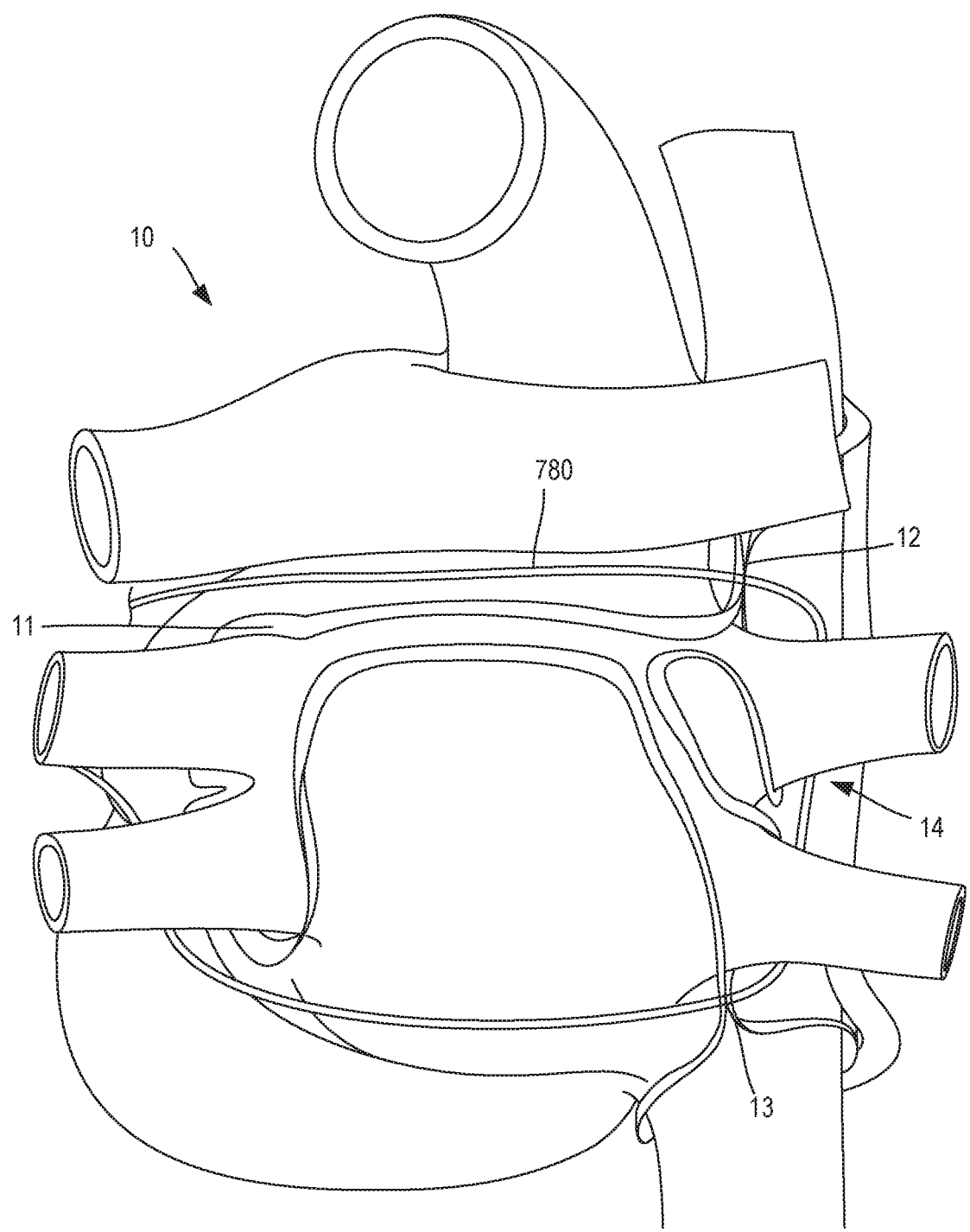
FIG. 22 is an illustration of a guidewire disposed within the pericardial space and about the pulmonary veins of the heart.

In this manner, the guidewire 780 can be advanced through the lumen of the second catheter 730 and the lumen of the magnetic member 735 of the first device; through the opening in the inferior pericardial reflection 13, and through the lumen of the second magnetic member 735' and the lumen of the fifth catheter 730' of the second device 700'. In some instances, the guidewire 780 can be advanced through the lumens such that a proximal end portion of the guidewire 780 (not shown) extends and/or is disposed proximal to the handle of the first device 700 and a distal end portion of the guidewire 780 (not shown) extends and/or is disposed proximal to the handle of the second device 700'. In other instances, the end portions of the guidewire 780 need not extend through the devices 700 and/or 700'. In this example, the guidewire 780 is advanced through the lumens such that the guidewire 780 is disposed and/or positioned about the pulmonary veins 14. Moreover, once the guidewire 780 is in a desired position, the operator can manipulate the first device 700 to retract the delivery catheter 702, the first catheter 720, the second catheter 730, and the first magnetic member 735 from the body of the patient without retracting the guidewire 780. Similarly, the operator can manipulate the second device 700' to retract the delivery catheter 702', the fourth catheter 720', the fifth catheter 730', and the second magnetic member 735' from the body of the patient without retracting the guidewire 780. In other words, a single continuous guidewire (i.e., the guidewire 780) is disposed within the pericardial space and substantially circumscribes the pulmonary veins 14, as shown in FIG. 22.

Figure 23:
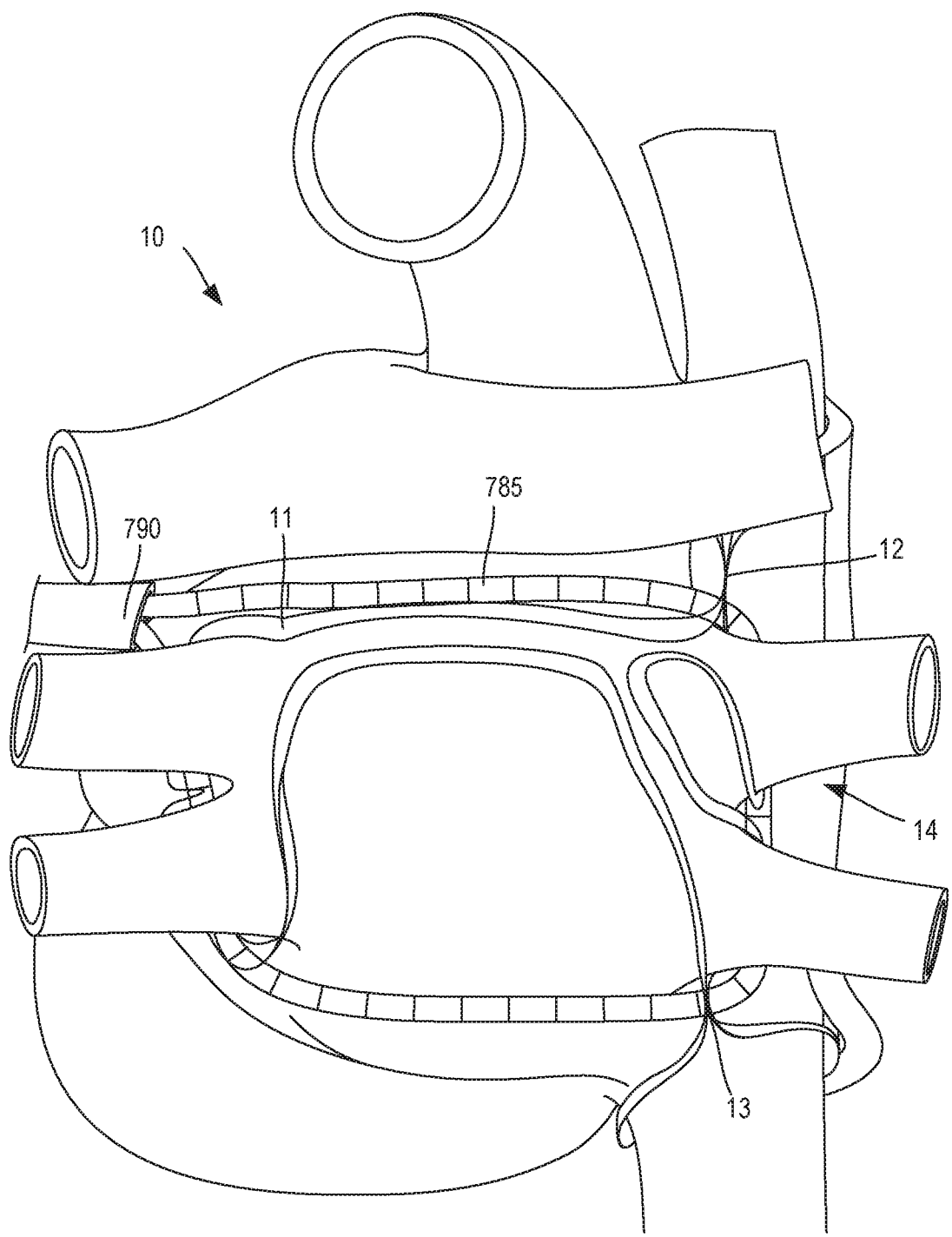
FIG. 23 is an illustration of an ablation catheter disposed within the pericardial space and about the pulmonary veins of the heart via the guidewire of FIG. 22.

In the example, shown in FIGS. 14-23, with the guidewire 780 defining a path within the pericardial space and around the pulmonary veins 14, a medical device such as an ablation catheter 785 can be advanced within the pericardial space along the guidewire 780 (see FIG. 23). Moreover, in some instances, the operator can dispose each end of the ablation catheter 785 within in a lumen of a cinch tool 790, which in turn, can be advanced such that the ablation catheter 785 forms a loop that substantially circumscribes the pulmonary veins 14. In some instances, advancing the cinch tool 790 in a distal direction can, for example, tighten the ablation catheter 785 about the pulmonary veins 14. The ablation catheter 785 can then be used to ablate the cardiac tissue around the pulmonary veins 14. In some instances, the ablation catheter 785 can be used to form a continuous lesion along the cardiac tissue as described in detail in the '394 publication incorporated by reference herein and presented herewith as Exhibit A. Thus, the function and/or operation of the ablation catheter 785 is not described in further detail herein.

Figure 24:
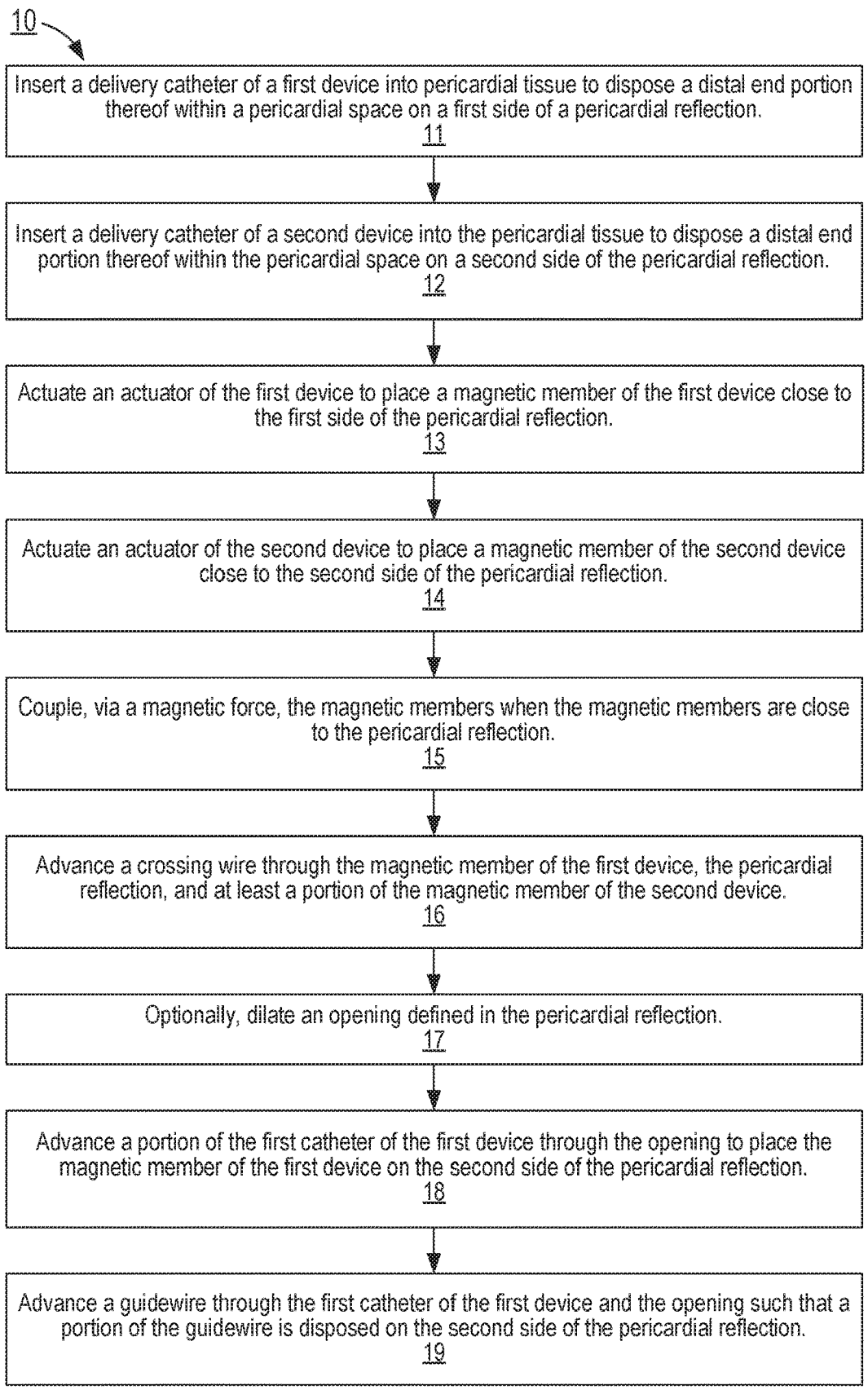
FIG. 24 is a flowchart illustrating a method of delivering a catheter to cardiac tissue according to an embodiment.

FIG. 24 is a flowchart illustrating a method 10 of using one or more devices such as those described herein, according to an embodiment. In some embodiments, at least some of the steps of the method 10 can be substantially similar to steps of the method of using the devices 700 and 700' described above with reference to FIGS. 14-23. In the embodiment shown in FIG. 24, the method 10 includes inserting a delivery catheter of a first delivery device into pericardial tissue of a heart such that a distal end portion of the delivery catheter is disposed within a pericardial space of the heart and on a first side of a pericardial reflection, at 11. In some embodiments, the first delivery device (also referred to herein as "first device") can be similar to the device(s) 100, 100', 200, 700, and/or 700' described herein. For example, the first delivery device can include the delivery catheter, a handle, a first catheter, a second catheter, a magnetic member, and an actuator (e.g., a first actuator and a second actuator, as described above). As described above with reference to FIG. 14, the delivery catheter of the first device can be inserted into the pericardial space via an incision and/or opening formed in the pericardium. In some instances, once the delivery catheter is at least partially disposed within the pericardial space, an operator (e.g., a surgeon or doctor) can move the handle of the first device in a distal direction (e.g., towards the heart) to place the distal end portion of the delivery catheter on the first side of the pericardial reflection (see e.g., FIGS. 14-16). In some instances, the pericardial reflection is a first or superior pericardial reflection, as described above with reference to FIGS. 15-18.

A delivery catheter of a second delivery device is inserted into the pericardial tissue of the heart such that a distal end portion of the delivery catheter of the second delivery device is disposed within the pericardial space on a second side of the pericardial reflection opposite the first side, at 12. In some embodiments, the second delivery device (also referred to herein as "second device") can be substantially similar to the first device, as described above, for example, with reference to the devices 100 and 100'. As described above with reference to the first device, the operator can move the handle of the second device in a distal direction to place the distal end portion of the delivery catheter on the second side of the pericardial reflection (see e.g., FIG. 16).

The actuator of the first device is then actuated to advance the magnetic member of the first device relative to the delivery catheter of the first device to place the magnetic member of the first device close to the first side of the pericardial reflection, at 13. Similarly, an actuator of the second device is actuated to advance a magnetic member of the second device relative to the delivery catheter of the second device to place the magnetic member of the second device close to the second side of the pericardial reflection, at 14. The magnetic members of the first device and the second device can be substantially similar to any of those described herein (e.g., the magnetic members 135, 135', 235, 335, 335', 435, 435', 535, 535', 635, 635', 735, and/or 735').

When the magnetic member of the first device is close to the first side of the pericardial reflection and the magnetic member of the second device is close to the second side of the pericardial reflection, the magnetic member of the first device is coupled, via magnetic force, to the magnetic member of the second device, at 15. More particularly, the magnetic members of the first device and the second device are coupled such that a portion of the pericardial reflection is disposed therebetween (see e.g., FIG. 17). Once the magnetic members are coupled with the portion of the pericardial reflection disposed therebetween, a flexible needle or sharpened guide wire (also referred to herein as a crossing wire) is advanced through a lumen of the magnetic member of the first device, the pericardial reflection, and at least a portion of a lumen of the magnetic member of the second device, at 16 (see e.g., FIG. 17).

In some instances, once the crossing wire pierces and/or punctures the pericardial reflection to define an opening therethrough, the crossing wire can be withdrawn such that a distal end of the crossing wire is at least within or proximal to a distal end of the magnetic member of the first device. In other instances, the crossing wire can be completely withdrawn from the first device and the second device.

In some instances, the method 10 optionally includes dilating the opening defined in the pericardial reflection as a result of the advancing the crossing wire, at 17. In some instances, for example, a dilation catheter can be advanced into the pericardial space (e.g., via the delivery catheter or outside of the delivery catheter). In other instances, the crossing wire can include a dilation portion or the like that can be actuated and/or otherwise dilated. In such instances, the crossing wire can remain in an advanced position (e.g., as shown in FIG. 17). Thus, a diameter of the opening defined in the pericardial reflection can be increased such that, for example, the diameter of the opening is larger than at least an outer diameter of the first catheter of the first device.

A portion of the first catheter of the first device is advanced through the opening defined in the pericardial reflection to place the magnetic member of the first device on the second side of the pericardial reflection, at 18. For example, in some embodiments, the second catheter and the magnetic member can be retracted into the first catheter prior to the first catheter being advanced through the pericardial reflection. In some instances, such a retraction into the first catheter can limit and/or substantially prevent damage to and/or bending of the more flexible second catheter (as described above with reference to the device 200). In this manner, a portion of the first catheter, a portion of the second catheter, and the magnetic member are disposed on the second side of the pericardial reflection, as shown in FIGS. 18 and 19. In some embodiments, after the portion of the first catheter is advanced through the opening defined in the pericardial reflection, a guidewire is advanced through the lumen of the first catheter and the opening defined by the pericardial reflection such that a portion of the guidewire is disposed on the second side of the pericardial reflection, at 19.

In some instances, with the guidewire extending through the opening in the pericardial reflection, a catheter (e.g., an ablation catheter or the like) and/or any other suitable medical device can be advanced along the guidewire and through the pericardial reflection. In other instances, such as those described above with reference to FIGS. 14-23, the first device and the second device can be used to define an opening in, for example, a second pericardial reflection prior to the advancing of the guidewire through the delivery catheter and the opening defined by the pericardial reflection. For example, in some instances, the method 10 can optionally include positioning the first catheter of the first device in a desired position on a first side of a second or inferior pericardial reflection and positioning the first catheter (retracted into the delivery catheter or extending from the delivery catheter) of the second device on a second side of the second or posterior pericardial reflection. As described above with reference to the superior pericardial reflection, an operator can then manipulate the devices to magnetically couple the magnetic members such that a portion of the posterior pericardial reflection is disposed therebetween. Once the magnetic members are coupled, the operator can then advance the crossing wire through the first device, the inferior pericardial reflection, and into the lumen of the magnetic member of the second device, as shown, for example, in FIG. 20.

As described above with reference to step 19 of the method 10, the guidewire can then be advanced through the first device (e.g., a lumen of the second catheter and the lumen of the magnetic member of the first device), the superior pericardial reflection, the inferior pericardial reflection, and into the second device (e.g., into the lumen of the second magnetic member and a lumen of the fifth catheter of the second device), as shown in FIG. 20. Thus, as described above with reference to FIG. 21, the guidewire can be positioned within the pericardial space to surround and/or substantially circumscribe the pulmonary veins of the heart. Moreover, in some instances, such as those shown in FIGS. 22 and 23, an ablation catheter can then be advanced along the guidewire to circumscribe the pulmonary veins within the pericardial space, as described above and as described, for example, in the '394 publication incorporated by reference herein and presented herewith as Exhibit A.

Figure 27A:
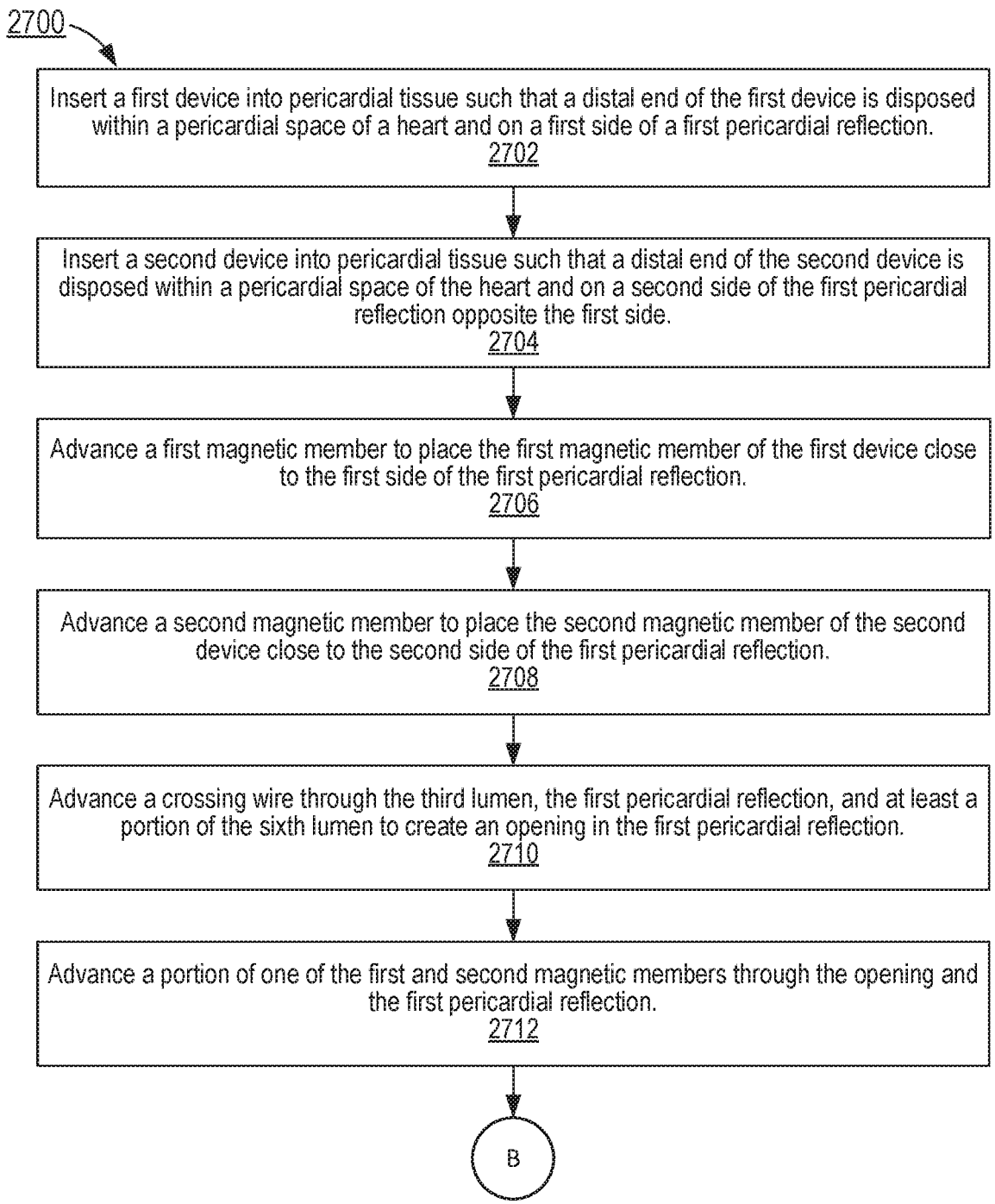
FIG. 27A is a flowchart illustrating a method of delivering a catheter to cardiac tissue according to an embodiment.
Figure 27B:
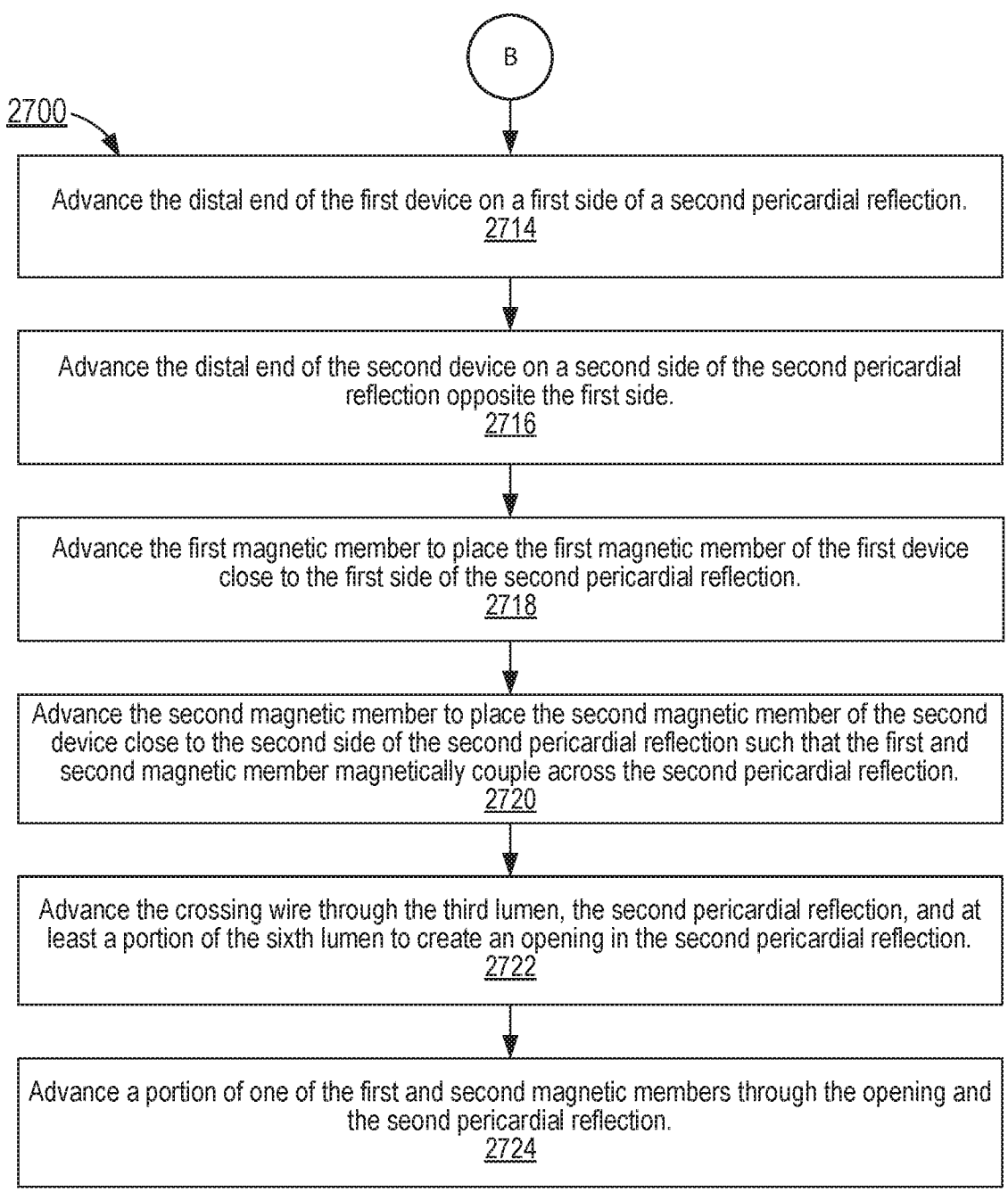
FIG. 27B is a flowchart illustrating a method of delivering a catheter to cardiac tissue according to an embodiment.

FIGS. 27A-27B are flowcharts illustrating a method 2700 of using one or more devices such as those described herein, according to an embodiment. In some embodiments, at least some of the steps of the method 2700 can be substantially similar to steps of the method of using the devices 700 and 700' described above with reference to FIGS. 14-23. In the embodiment shown in FIGS. 27A-27B, the method 2700 includes inserting a first device into pericardial tissue of a heart of a subject such that a distal end of the first device is disposed within a pericardial space of the heart and on a first side of a first pericardial reflection, at 2702. In some embodiments, the first delivery device (also sometimes referred to herein as "first device") can be similar to the device(s) 100, 100', 200, 700, and/or 700' described herein. For example, the first device can include a first catheter defining a first longitudinal axis and a first lumen therethrough and a second catheter defining a second longitudinal axis and a second lumen therethrough. At least a portion of the second catheter can be configured to slide within the first lumen. A first magnetic member can be coupled to a distal end of the second catheter. The first magnetic member can define a third lumen therethrough. The third lumen can be in fluid communication with the second lumen. As described above with reference to FIG. 14, the first device can be inserted into the pericardial space via an incision and/or opening formed in the pericardium. In some instances, once the delivery catheter is at least partially disposed within the pericardial space, an operator (e.g., a surgeon or doctor) can move a handle of the first device in a distal direction (e.g., towards the heart) to place the distal end of the first device on the first side of the pericardial reflection (see e.g., FIGS. 14-16). In some instances, the pericardial reflection is a first or superior pericardial reflection, as described above with reference to FIGS. 15-18.

A second device can be inserted into the pericardial tissue of the heart such that a distal end of the second device is disposed within the pericardial space on a second side of the first pericardial reflection opposite the first side, at 2704. In some embodiments, the second delivery device (also referred to herein as "second device") can be substantially similar to the first device, as described above, for example, with reference to the devices 100 and 100'. As described above with reference to the first device, the operator can move a handle of the second device in a distal direction to place the distal end of the second device on the second side of the pericardial reflection (see e.g., FIG. 16). For example, the second device can include a fourth catheter defining a fourth longitudinal axis and a fourth lumen therethrough, and a fifth catheter defining a fifth longitudinal axis and a fifth lumen therethrough. At least a portion of the fifth catheter can be configured to slide within the fourth lumen. A second magnetic member can be coupled to a distal end of the fifth catheter. The second magnetic member can define a sixth lumen therethrough. The sixth lumen can be in fluid communication with the fifth lumen.

The first magnetic member may be advanced (e.g., by actuation of an actuator of the first device) to place the first magnetic member close to the first side of the first pericardial reflection, at 2706. Similarly, the second magnetic member can be advanced to place the second magnetic member close to the second side of the first pericardial reflection such that the first magnetic member couples to the second magnetic member across the first pericardial reflection via a magnetic force when the first magnetic member is close to the first side of the first pericardial reflection and the second magnetic member is close to the second side of the first pericardial reflection, at 2708. The magnetic members of the first device and the second device can be substantially similar to any of those described herein (e.g., the magnetic members 135, 135', 235, 335, 335', 435, 435', 535, 535', 635, 635', 735, and/or 735').

More particularly, the magnetic members of the first device and the second device are coupled such that a portion of the first pericardial reflection is disposed therebetween (see e.g., FIG. 17). Once the magnetic members are coupled with the portion of the first pericardial reflection disposed therebetween, a flexible needle or sharpened guide wire (also sometimes referred to herein as a crossing wire) is advanced through the third lumen of the magnetic member of the first device, the first pericardial reflection, and at least a portion of the sixth lumen of the second magnetic member of the second device to create an opening in the first pericardial reflection, at 2710 (see e.g., FIG. 17).

In some instances, once the crossing wire pierces and/or punctures the pericardial reflection to define the opening therethrough, the crossing wire can be withdrawn such that a distal end of the crossing wire is at least within or proximal to a distal end of the first magnetic member of the first device. In other instances, the crossing wire can be completely withdrawn from the first device and the second device.

In some instances, the method 2700 optionally includes dilating the opening defined in the pericardial reflection as a result of the advancing the crossing wire. In some instances, for example, a dilation catheter can be advanced into the pericardial space (e.g., via the delivery catheter or outside of the delivery catheter). In other instances, the crossing wire can include a dilation portion or the like that can be actuated and/or otherwise dilated. In such instances, the crossing wire can remain in an advanced position (e.g., as shown in FIG. 17). Thus, a diameter of the opening defined in the first pericardial reflection can be increased such that, for example, the diameter of the opening is larger than at least an outer diameter of the first catheter of the first device.

A portion of one of the first and second magnetic members may be advanced through the opening and the first pericardial reflection, at 2712. For example, a portion of the first catheter, a portion of the second catheter, and the first magnetic member can be disposed on the second side of the first pericardial reflection, as shown in FIGS. 18 and 19. In some embodiments, after the portion of the first catheter is advanced through the opening defined in the pericardial reflection, a guidewire is advanced through the first lumen of the first catheter and the opening defined by the first pericardial reflection such that a portion of the guidewire is disposed on the second side of the first pericardial reflection.

In some instances, with the guidewire extending through the opening in the first pericardial reflection, a catheter (e.g., an ablation catheter or the like) and/or any other suitable medical device can be advanced along the guidewire and through the pericardial reflection. In other instances, such as those described above with reference to FIGS. 14-23, the first device and the second device can be used to define an opening in, for example, a second pericardial reflection prior to the advancing of the guidewire through the delivery catheter and the opening defined by the first pericardial reflection. In some embodiments, as shown in FIG. 27B, the method 2700 can include advancing the distal end of the first device on a first side of a second or posterior pericardial reflection, at 2714. The distal end of the second device can be advanced on a second side of the second pericardial reflection, at 2716. The first magnetic member can be advanced to place the first magnetic member close to the first side of the second pericardial reflection, at 2718. Similarly, the second magnetic member may be advanced to place the second magnetic member close to the second side of the second pericardial reflection such that the first magnetic member couples to the second magnetic member across the second pericardial reflection via a magnetic force when the first magnetic member is close to the first side of the second pericardial reflection and the second magnetic member is close to the second side of the first second reflection, at 2720. The crossing wire may be advanced through the third lumen, the second pericardial reflection, and at least a portion of the sixth lumen to create an opening in the second pericardial reflection, at 2722. The portion of one of the first and second magnetic members may be advanced through the opening and the second pericardial reflection, at 2724.

As described above with reference to the superior pericardial reflection, an operator can then manipulate the devices to magnetically couple the magnetic members such that a portion of the posterior pericardial reflection is disposed therebetween. Once the magnetic members are coupled, the operator can then advance the crossing wire through the first device, the inferior pericardial reflection, and into the lumen of the magnetic member of the second device, as shown, for example, in FIG. 20.

As described herein, the guidewire can then be advanced through the first device (e.g., a second lumen of the second catheter and the third lumen of the first magnetic member of the first device), the superior pericardial reflection, the inferior pericardial reflection, and into the second device (e.g., into the sixth lumen of the second magnetic member and a fifth lumen of the fifth catheter of the second device). Thus, as described above with reference to FIG. 21, the guidewire can be positioned within the pericardial space to surround and/or substantially circumscribe the pulmonary veins of the heart. Moreover, in some instances, such as those shown in FIGS. 22 and 23, an ablation catheter can then be advanced along the guidewire to circumscribe the pulmonary veins within the pericardial space, as described above and as described, for example, in the '394 publication incorporated by reference herein and presented herewith as Exhibit A.

Any of the embodiments described herein can be used with any suitable devices, catheters, and/or systems to place, for example, a catheter in a desired position when anatomic structures or the like might otherwise block and/or present challenges to catheterization. Similarly, any of the embodiments described herein can be used in any suitable procedure such as, for example, any of those described in the '394 publication incorporated by reference herein and presented herewith as Exhibit A. The ablation catheters and/or the like described herein (e.g., the ablation catheter 785) can be similar to any of those described in the '394 publication. Thus, any of the ablation catheters described herein can have electrode designs adapted for various procedures and/or uses, depending on the devices and/or procedures in which such electrodes are to be employed. Although examples presented herein describe using one or more devices to place an ablation catheter, in some embodiments, the devices and/or methods described herein can be used in any suitable procedure to place a catheter or the like within a portion of a body.

Figure 25:
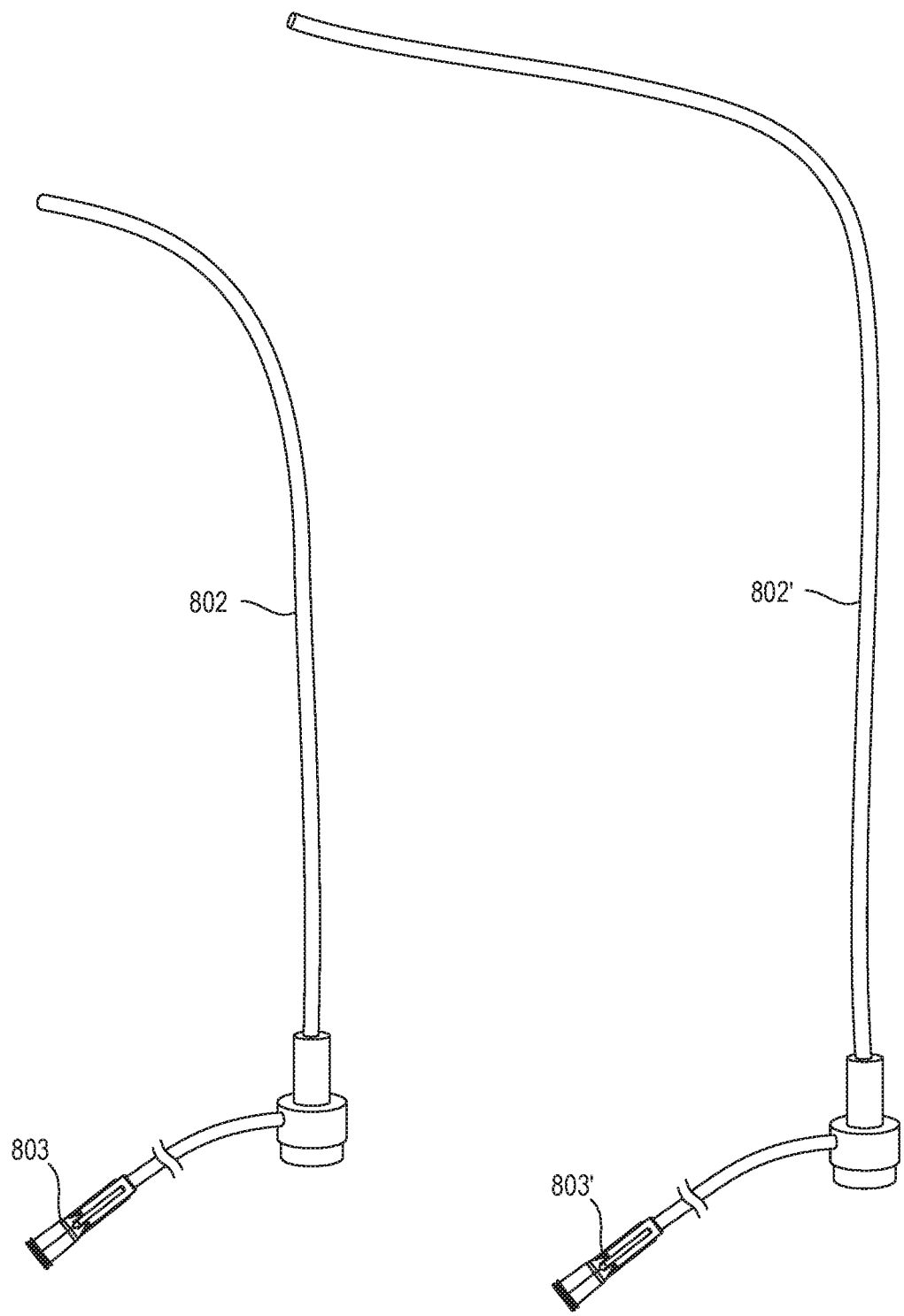
FIG. 25 is a schematic illustration of a first delivery catheter and second delivery catheter, according to an embodiment.

By way of another example, any of the embodiments described herein can be used with any suitable delivery catheter configured to receive a portion of one or more catheters to allow for insertion and/or placement of the one or more catheters into or at a target tissue. For example, any of the embodiments described herein can be used with one or more delivery catheters such as, for example, the delivery catheters 102 and 102' described above with reference to FIGS. 1-3 and/or the delivery catheters 702 and 702' described above with reference to FIGS. 14-23. As shown in FIG. 25, in other embodiments, any of the devices described herein can be used with a first delivery catheter 802 (e.g., a transverse sinus catheter) and/or a second delivery catheter 802' (e.g., an oblique sinus catheter). In the embodiment shown in FIG. 25, the first delivery catheters 802 and/or 802' can be substantially similar in form and/or function to the delivery catheters 102, 702 and/or the delivery catheters 102', 702', respectively. Moreover, each of the first delivery catheter 802 and the second delivery catheter 802' can include a port 803 and 803', respectively, as illustrated. The ports 803 and 803' are in fluid communication with a lumen of the delivery catheters 802 and 802' and can, for example, be coupled to a fluid source and/or vacuum source to provide lavage and/or suction, respectively. In some embodiments, the ports 803 and 803' can be substantially similar in form and/or function to the port 103 of the first delivery device 102 and/or port 103' of the second delivery device 102'. In other embodiments, the ports 803 and/or 803' can be substantially similar in form and/or function to the port 244 of the delivery device 200, described above with reference to FIGS. 4-7.

The delivery catheters 802 and 802' can be formed of or from any suitable material and/or combination of materials. For example, in some embodiments, the delivery catheters 802 and 802' can be formed from a relatively rigid plastic or the like (e.g., a plastic with a relatively high stiffness). For example, in some embodiments, the delivery catheters 802 and 802' can be formed of polyether block amide (Pebax), polyurethane, nylon, polyethylene, and/or fluoropolymers such as polytetrafluoroethylene (PTFE) or fluorinated ethylene propylene (FEP), and/or combinations thereof. In some embodiments, the delivery catheters 802 and 802' can be formed of any suitable material(s) having a durometer ranging between about 25 shore D and 80 shore D, including all values and sub-ranges in between. In the embodiment shown in FIG. 25, the delivery catheters 802 and 802' can be formed of a material with a stiffness sufficient to retain and/or regain a shape of the delivery catheters 802 and 802' upon or after application of force (e.g., under their own weight).

The delivery catheters 802 and 802' can be pre-formed with any desired bend, curve, twist, etc. that can be associated with, for example, a target tissue within the body. By way of example, in some embodiments, the delivery catheters 802 and 802' can be substantially similar to the delivery catheters 702 and 702', respectively, described above with reference to FIGS. 14-23. In this manner, the first delivery catheter 802 (the transverse sinus catheter) can be formed with a shape (e.g., bend, curve, and/or the like) suitable for placing a distal end portion of the first delivery catheter 802 within the pericardial space of a heart at a desired position relative to, for example, access to a superior pericardial reflection (e.g., advancing the transverse sinus catheter 802 through the transverse sinus of the heart to be disposed on a first side of the reflection). Likewise, the second delivery catheter 802' can be formed with a shape (e.g., bend, curve, and/or the like) suitable for placing a distal end portion of the second delivery catheter 802' within the pericardial space of the heart at a desired position relative to access to a second side of the superior pericardial reflection (e.g., on a second side of the reflection). Accordingly, the approximate size and/or shape of the delivery catheters 802 and 802' can be associated with and/or at least partially based on a predetermined and/or desired path from an insertion point to a target tissue. In embodiments in which the delivery catheters 802 and 802' are placed in desired positions relative to a superior pericardial reflection, the second delivery catheter 802' can be longer than the first delivery catheter 802 due to, for example, a longer distance along a predetermined path from an insertion point to the target tissue. For example, in some embodiments, the relatively smaller curve of the first delivery catheter 802 can be useful for accessing the transverse sinus anteriorly, and the relatively larger curve of the second delivery catheter 802' is useful for accessing the superior reflection anteriorly, for accessing the inferior reflection posteriorly (after partial insertion), and for subsequent wrapping around the heart. In some embodiments, the length and/or shape of the second delivery catheter 802' (e.g., the oblique sinus catheter) can be useful for advancing the oblique sinus catheter 802' through the oblique sinus of the heart to be disposed in a desired position relative to the inferior reflection.

Any of the embodiments described herein can include components that are manufactured, packaged, and sold independently or collectively. For example, in some instances, any of the components in the various embodiments described herein can be manufactured, assembled, and packaged collectively during a manufacturing process. In such instances, the package can be sold and/or otherwise provided as a kit. For example, FIG. 26 is an illustration of a kit 906 according to an embodiment. The kit 906 can include any of the components, devices, and/or apparatus described herein. By way of example, the kit 906 includes a first delivery device 900 and a second delivery device 900', which are each disposed within a package 908. In some embodiments, the first delivery device 900 and the second delivery device 900' are each substantially similar in form and/or function to the delivery device 200 described above with reference to FIGS. 4-7. Specifically, as shown in FIG. 26, the first delivery device 900 includes a handle 910, a first catheter 920, a second catheter 930, a magnetic member 935, a first actuator 950, and a second actuator 960. Similarly, the second delivery device 900' includes a handle 910', a first catheter 920', a second catheter 930', a magnetic member 935', a first actuator 950', and a second actuator 950'.

The package 908 can be any suitable package. For example, in some embodiments, the package 908 can be formed from a fluid impermeable plastic or the like and can be in a substantially sealed configuration prior to a user (e.g., a doctor, surgeon, interventionalist, etc.) opening the package 908 for use. In some embodiments, such an arrangement can allow the package 908 to define a substantially sterile environment within which the delivery devices 900 and 900' are disposed prior to use. For example, in some instances, the kit 906 can be assembled during a manufacturing process occurring within, for example, an environment configured to sterilize the package 908, and the delivery devices 900 and 900' (e.g., ethylene oxide or the like). Therefore, when the package 908 is placed in the sealed configuration, the delivery devices 900 and 900' are maintained in a sterilized environment.

While described above as including the first delivery device 900 and the second delivery device 900', the kit 906 can include any other suitable device and/or component. For example, in some embodiments, the kit 906 can optionally include a first delivery catheter 902 and a second delivery catheter 902', as shown in FIG. 26. In such embodiments, the first delivery catheter 902 and the second delivery catheter 902' can be substantially similar to the delivery catheters described herein (e.g., the delivery catheters 702 and 702'). Thus, in some embodiments, the package 908 can maintain the first delivery device 900, the second delivery device 900', the first delivery catheter 902, and the second delivery catheter 902' within a substantially sterile environment prior to use (e.g., during shipping and/or storage). In some embodiments, the kit 906 can include multiple first delivery catheters 902 and multiple second delivery catheters 902'. In such embodiments, each delivery catheter 902 and/or 902' can have a different bend, shape, length, diameter, etc. In some embodiments, providing various lengths, sizes, and/or shapes of the delivery catheters 902 and/or 902' can allow a surgeon or user to select a desired delivery catheter 902 and/or 902' based at least in part on a patient's cardiac anatomy (and/or for any other suitable reason).

Although not shown in FIG. 26, in some embodiments, the kit 906 can also include, for example, a guidewire, a needle, a sharpened guidewire, and/or the like (e.g., the needle 775 and/or the guidewire 780 described above with reference to FIGS. 14-23). In some embodiments (not shown), the kit 906 can include an ablation catheter as disclosed in the in the '394 publication incorporated by reference herein and presented herewith as Exhibit A. In some embodiments, the kit 906 can include, for example, one or more pajunk needle(s), micropuncture set(s), and/or any other suitable epicardial access device, guidewire, and/or catheter.

While various embodiments have been described above, it should be understood that they have been presented by way of example only, and not limitation. Where schematics and/or embodiments described above indicate certain components arranged in certain orientations or positions, the arrangement of components can be modified. While the embodiments have been particularly shown and described, it will be understood that various changes in form and details can be made. Although various embodiments have been described as having particular features and/or combinations of components, other embodiments are possible having a combination of any features and/or components from any of embodiments as discussed above.

Where methods and/or events described above indicate certain events and/or procedures occurring in certain order, the ordering of certain events and/or procedures can be modified. Additionally, certain events and/or procedures can be performed concurrently in a parallel process when possible, as well as performed sequentially as described above.

What is claimed is:

1. A method, comprising:
   inserting a first device into pericardial tissue of a heart of a subject such that a distal end of the first device is disposed within a pericardial space of the heart and on a first side of a first pericardial reflection, the first device including:
   a first handle;
   a first catheter coupled to the first handle and defining a first longitudinal axis and a first lumen therethrough, the first catheter having a distal end portion terminating in a distal end, the first catheter coupled to a first actuator that is movably coupled to and rotatable relative to the first handle and is configured to deflect the distal end portion of the first catheter;
   a second catheter having an outer diameter and defining a second longitudinal axis and a second lumen therethrough, the second catheter coupled to a second actuator that is coupled to the first handle and is configured to be movable linearly relative to the first handle, wherein at least a portion of the second catheter is configured to slide within the first lumen; and
   a first magnetic member coupled to a distal end of the second catheter and positioned distally of the distal end of the first catheter, the first magnetic member defining a third lumen therethrough, wherein the third lumen is in fluid communication with the second lumen, the first magnetic member having a distal surface having a first shape, the first magnetic member having a diameter greater than the outer diameter, wherein linear movement of the second actuator relative to the first handle varies a spacing between the first magnetic member and the distal end of the first catheter;
   inserting a second device into the pericardia! tissue of the heart such that a distal end of the second device is disposed within the pericardial space on a second side of the first pericardial reflection opposite the first side, the second device including:
   a second handle;
   a fourth catheter coupled to the second handle and defining a fourth longitudinal axis and a fourth lumen therethrough, the fourth catheter having a distal end portion terminating in a distal end, the fourth catheter coupled to a third actuator that is movably coupled to and rotatable relative to the second handle and is configured to deflect the distal end portion of the fourth catheter;
   a fifth catheter having an outer diameter and defining a fifth longitudinal axis and a fifth lumen therethrough, the fifth catheter coupled to a fourth actuator that is coupled to the second handle and is configured to be movable linearly relative to the second handle, wherein at least a portion of the fifth catheter is configured to slide within the fourth lumen; and
   a second magnetic member coupled to a distal end of the fifth catheter, the second magnetic member defining a sixth lumen therethrough, wherein the sixth lumen is in fluid communication with the fifth lumen, the second magnetic member having a distal surface having a second shape that is different than and complimentary to the first shape, and wherein linear movement of the fourth actuator relative to the second handle varies a spacing between the second magnetic member and the distal end of the second catheter;
   actuating the second actuator to advance the first magnetic member relative to the distal end of the first catheter to place the first magnetic member close to the first side of the first pericardial reflection;
   actuating the fourth actuator to advance the second magnetic member relative to the distal end of the fourth catheter to place the second magnetic member close to the second side of the first pericardial reflection such that the first magnetic member couples to the second magnetic member across the first pericardial reflection via a magnetic force when the first magnetic member is close to the first side of the first pericardial reflection and the second magnetic member is close to the second side of the first pericardial reflection, and wherein the first shape of the distal surface of the first magnetic member and the second shape of the distal surface of the second magnetic member are configured to align the third lumen and the sixth lumen when the first and second magnetic members are magnetically coupled;
   creating a first opening in the first pericardial reflection;
   advancing a guide wire through the third lumen and extended into at least a portion of the sixth lumen through the first opening in the first pericardial reflection;
   advancing a portion of the first catheter, the second catheter and the first magnetic member through the first opening and the first pericardial reflection over the guidewire;
   with the first catheter and the second catheter extending through the first opening and the first pericardial reflection, advancing the second catheter and the first magnetic member to a first side of a second pericardial reflection;
   repositioning the fourth catheter and the fifth catheter to place the second magnetic member close to a second side of the second pericardial reflection such that the first magnetic member magnetically couples to the second magnetic member across the second pericardial reflection;
   creating a second opening in the second pericardial reflection; and advancing the guide wire through the third lumen, the second pericardial reflection, and into the sixth lumen through the second opening in the second pericardial reflection.

2. The method of claim 1, further comprising dilating the first opening in the first pericardial reflection.

3. The method of claim 1, comprising advancing a crossing wire through the third lumen to create the first opening in the first pericardial reflection, and further comprising withdrawing the crossing wire from the first pericardial reflection and the third lumen.

4. The method of claim 1, further comprising fluoroscopically imaging the first and second devices disposed within the pericardial space.

5. A method, comprising:
inserting a first device into pericardial tissue of a heart of a subject such that a distal end of the first device is disposed within a pericardial space of the heart and on a first side of a first pericardial reflection, the first device including:
a first handle;
a first catheter coupled to the first handle and defining a first longitudinal axis and a first lumen therethrough, the first catheter having a distal end portion terminating in a distal end, the first catheter coupled to a first actuator that is movably coupled to and rotatable relative to the first handle and is configured to deflect the distal end portion of the first catheter;
a second catheter having an outer diameter and defining a second longitudinal axis and a second lumen therethrough, the second catheter coupled to a second actuator that is coupled to the first handle and is configured to be movable linearly relative to the first handle, wherein at least a portion of the second catheter is configured to slide within the first lumen; and
a first magnetic member coupled to a distal end of the second catheter and positioned distally of the distal end of the first catheter, the first magnetic member defining a third lumen therethrough, wherein the third lumen is in fluid communication with the second lumen, the first magnetic member having a distal surface having a first shape, the first magnetic member having a diameter greater than the outer diameter, wherein linear movement of the second actuator relative to the first handle varies a spacing between the first magnetic member and the distal end of the first catheter;
inserting a second device into the pericardial tissue of the heart such that a distal end of the second device is disposed within the pericardial space on a second side of the first pericardial reflection opposite the first side, the second device including:
a second handle;
a fourth catheter coupled to the second handle and defining a fourth longitudinal axis and a fourth lumen therethrough, the fourth catheter having a distal end portion terminating in a distal end, the fourth catheter coupled to a third actuator that is movably coupled to and rotatable relative to the second handle and is configured to deflect the distal end portion of the fourth catheter;
a fifth catheter having an outer diameter and defining a fifth longitudinal axis and a fifth lumen therethrough, the fifth catheter coupled to a fourth actuator that is coupled to the second handle and is configured to be movable linearly relative to the second handle, wherein at least a portion of the fifth catheter is configured to slide within the fourth lumen; and a second magnetic member coupled to a distal end of the fifth catheter, the second magnetic member defining a sixth lumen therethrough, wherein the sixth lumen is in fluid communication with the fifth lumen, the second magnetic member having a distal surface having a second shape that is different than and complimentary to the first shape, and wherein linear movement of the fourth actuator relative to the second handle varies a spacing between the second magnetic member and the distal end of the fourth catheter;

actuating the second actuator to advance the first magnetic member relative to the distal end of the first catheter to place the first magnetic member close to the first side of the first pericardial reflection;

actuating the fourth actuator to advance the second magnetic member relative to the distal end of the fourth catheter to place the second magnetic member close to the second side of the first pericardial reflection such that the first magnetic member couples to the second magnetic member across the first pericardial reflection via a magnetic force when the first magnetic member is close to the first side of the first pericardial reflection and the second magnetic member is close to the second side of the first pericardial reflection;

advancing a crossing wire through the third lumen, the first pericardial reflection, and at least a portion of the sixth lumen to create an opening in the first pericardial reflection; and delivering a guidewire through the third lumen, the opening in the first pericardial reflection, the opening in the second pericardial reflection, and the sixth lumen;

advancing a portion of the first catheter, the second catheter, and the first magnetic member through the opening and the first pericardial reflection over the guidewire;

advancing the distal end of the first device through the opening in the first pericardial reflection to a first side of a second pericardial reflection;

advancing the distal end of the second device on a second side of the second pericardial reflection;

advancing the first magnetic member to place the first magnetic member close to the first side of the second pericardial reflection;

advancing the second magnetic member to place the second magnetic member close to the second side of the second pericardial reflection such that the first magnetic member couples to the second magnetic member across the second pericardial reflection via a magnetic force when the first magnetic member is close to the first side of the second pericardial reflection and the second magnetic member is close to the second side of the first second reflection, and wherein the first shape of the distal surface of the first magnetic member and the second shape of the distal surface of the second magnetic member are configured to align the third lumen and the sixth lumen when the first and second magnetic members are magnetically coupled;

advancing the crossing wire through the third lumen, the second pericardial reflection, and at least a portion of the sixth lumen to create an opening in the second pericardial reflection;
and
advancing the portion of one of the first and second magnetic members through the opening and the second pericardial reflection.

6. The method of claim 5, further comprising withdrawing the crossing wire from the second pericardial reflection and the third lumen.

7. The method of claim 5, further comprising withdrawing the first and second devices from a body of a subject while leaving the guidewire in place.

8. The method of claim 7, further comprising advancing an ablation device over the guidewire and through the openings in the first and second pericardial reflections.

9. The method of claim 8, further comprising at least partially encircling left and right pulmonary veins with the ablation device.

10. The method of claim 9, wherein the ablation device comprises an ablation catheter.

11. The method of claim 10, further comprising forming a circumferential ablation lesion using the ablation catheter.

12. The method of claim 5, further comprising advancing a guidewire through the first lumen and the second pericardial reflection such that a portion of the guidewire is disposed on the second side of the second pericardial reflection.

13. The method of claim 5, further comprising dilating the opening in the second pericardial reflection.

14. The method of claim 5, wherein inserting the first and second devices into the pericardial tissue includes inserting an introducer catheter into a body of a subject.

15. The method of claim 5, wherein inserting the first device into the pericardial tissue includes advancing the first device along a transverse sinus of the heart.

16. The method of claim 5, wherein inserting the second device into the pericardial tissue includes advancing the second device along an oblique sinus of the heart.

\* \* \* \* \*